US010912653B2

(12) United States Patent
To et al.

(10) Patent No.: US 10,912,653 B2
(45) Date of Patent: Feb. 9, 2021

(54) STABILIZED LATEROVERTICALLY-EXPANDING FUSION CAGE SYSTEMS WITH TENSIONER

(71) Applicant: INTEGRITY IMPLANTS INC., Palm Beach Gardens, FL (US)

(72) Inventors: John To, Newark, CA (US); John J. Flynn, Walnut Creek, CA (US); John Souza, Monroe, NC (US); Andrew Wolf, Jupiter, FL (US)

(73) Assignee: INTEGRITY IMPLANTS INC., Palm Beach Gardens, FL (US)

( * ) Notice: Subject to any disclaimer, the term of this patent is extended or adjusted under 35 U.S.C. 154(b) by 0 days.

(21) Appl. No.: 16/334,486

(22) PCT Filed: Sep. 21, 2017

(86) PCT No.: PCT/US2017/052708
§ 371 (c)(1),
(2) Date: Mar. 19, 2019

(87) PCT Pub. No.: WO2018/057733
PCT Pub. Date: Mar. 29, 2018

(65) Prior Publication Data
US 2019/0209339 A1 Jul. 11, 2019

Related U.S. Application Data

(63) Continuation of application No. 15/271,741, filed on Sep. 21, 2016, now Pat. No. 9,883,953.

(51) Int. Cl.
*A61F 2/44* (2006.01)
*A61F 2/46* (2006.01)
*A61F 2/30* (2006.01)

(52) U.S. Cl.
CPC ............ *A61F 2/4455* (2013.01); *A61F 2/442* (2013.01); *A61F 2/446* (2013.01); *A61F 2/447* (2013.01);
(Continued)

(58) Field of Classification Search
CPC ........ A61F 2/4455; A61F 2/442; A61F 2/446; A61F 2/4465; A61F 2/447; A61F 2/4611;
(Continued)

(56) References Cited

U.S. PATENT DOCUMENTS 4,309,777 A 1/1982 Patil
4,733,665 A 3/1988 Palmaz
(Continued)

FOREIGN PATENT DOCUMENTS

CN 101909548 7/2014
EP 1011503 2/1998
(Continued)

OTHER PUBLICATIONS

U.S. Appl. No. 16/290,428, filed Mar. 1, 2018, Shoshtaev—owned by Applicant.
(Continued)

*Primary Examiner* — Pedro Philogene
(74) *Attorney, Agent, or Firm* — Brian S. Boyer; Syndicated Law, PC.

(57) ABSTRACT

An intervertebral scaffolding system is provided having a laterovertically-expanding frame operable for a reversible collapse from an expanded state into a collapsed state, the laterovertically-expanding frame having a stabilizer, one or more tensioners, or a combination of the stabilizer with one or more tensioners. The stabilizer slidably engages with the distal region of the laterovertically-expanding frame and both the stabilizer and the one or more tensioners are configured for retaining the laterovertically-expanding
(Continued)

frame from a lateral movement that exceeds the expanded state, and the stabilizer can include a locking element that engages with the expansion member to lock the expansion member to the stabilizer when the expansion member is fully inserted into the frame. The expanded state, for example, can be configured to have an open graft distribution window that at least substantially closes upon the reversible collapse.

19 Claims, 41 Drawing Sheets

(52) U.S. Cl.
CPC .......... *A61F 2/4465* (2013.01); *A61F 2/4611* (2013.01); *A61F 2002/30515* (2013.01); *A61F 2002/30556* (2013.01); *A61F 2002/30579* (2013.01); *A61F 2002/30593* (2013.01); *A61F 2002/4627* (2013.01)

(58) Field of Classification Search
CPC .... A61F 2/441; A61F 2/30965; A61F 2/4684; A61F 2002/30515; A61F 2002/30556; A61F 2002/30579; A61F 2002/30593; A61F 2002/4627; A61F 2002/2817; A61F 2002/2835; A61F 2002/30019; A61F 2002/30581; A61F 2002/30598; A61F 2002/30777; A61F 2002/30779; A61F 2002/30785; A61F 2002/4435; A61F 2002/444; A61F 2002/4474; A61F 2310/00011; A61F 2310/00023; A61F 2310/00029; A61F 2310/00047; A61F 2310/00053; A61F 2310/00071; A61F 2310/00179; A61F 2310/00293
USPC ............... 623/17.11–17.16; 606/246–279
See application file for complete search history.

(56) References Cited

U.S. PATENT DOCUMENTS

| | | |
|---|---|---|
| 4,759,766 A | 7/1988 | Buettner-Janz et al. |
| 4,820,305 A | 4/1989 | Harms et al. |
| 4,997,432 A | 3/1991 | Keller |
| 5,192,327 A | 3/1993 | Brantigan |
| 5,221,261 A | 6/1993 | Termin et al. |
| 5,609,635 A | 3/1997 | Michelson |
| 5,658,336 A | 8/1997 | Pisharodi |
| 5,976,187 A | 11/1999 | Richelsoph |
| 5,980,522 A | 11/1999 | Koros |
| 5,980,552 A | 11/1999 | Pinchasik et al. |
| 6,039,761 A | 3/2000 | Li et al. |
| 6,102,950 A | 8/2000 | Vaccaro |
| 6,126,689 A | 10/2000 | Brett |
| 6,176,882 B1 | 1/2001 | Biedermann |
| 6,193,757 B1 | 2/2001 | Foley et al. |
| 6,368,351 B1 | 4/2002 | Glenn et al. |
| 6,375,682 B1 | 4/2002 | Fleischmann et al. |
| 6,395,031 B1 | 5/2002 | Foley et al. |
| 6,409,766 B1 | 6/2002 | Brett |
| 6,419,705 B1 | 7/2002 | Erickson |
| 6,432,107 B1 | 8/2002 | Ferree |
| 6,436,119 B1 | 8/2002 | Erb et al. |
| 6,443,989 B1 | 9/2002 | Jackson |
| 6,482,235 B1 | 11/2002 | Lambrecht et al. |
| 6,488,710 B2 | 12/2002 | Besselink |
| 6,491,724 B1 | 12/2002 | Ferree |
| 6,575,899 B1 | 6/2003 | Foley et al. |
| 6,582,439 B1 | 6/2003 | Sproul |
| 6,582,441 B1 | 6/2003 | He et al. |
| 6,582,467 B1 | 6/2003 | Teitelbaum |
| 6,595,998 B2 | 7/2003 | Johnson et al. |
| 6,666,891 B2 | 12/2003 | Boehm, Jr. et al. |
| 6,821,276 B2 | 11/2004 | Lambrecht et al. |
| 6,821,298 B1 | 11/2004 | Jackson |
| 6,893,464 B2 | 5/2005 | Kiester |
| 7,018,415 B1 | 3/2006 | McKay |
| 7,083,650 B2 | 8/2006 | Moskowitz et al. |
| 7,087,055 B2 | 8/2006 | Lim et al. |
| 7,204,853 B2 | 4/2007 | Gordon et al. |
| 7,214,243 B2 | 5/2007 | Taylor |
| 7,217,293 B2 | 5/2007 | Branch |
| 7,544,208 B1 | 6/2009 | Mueller et al. |
| 7,621,950 B1 | 11/2009 | Globerman et al. |
| 7,643,884 B2 | 1/2010 | Pond et al. |
| 7,655,046 B2 | 2/2010 | Dryer et al. |
| 7,678,148 B2 | 3/2010 | Peterman |
| 7,731,751 B2 | 6/2010 | Butler et al. |
| 7,771,473 B2 | 8/2010 | Thramann |
| 7,819,921 B2 | 10/2010 | Grotz |
| 7,828,845 B2 | 11/2010 | Estes et al. |
| 7,828,849 B2 | 11/2010 | Lim |
| 7,846,206 B2 | 12/2010 | Oglaza et al. |
| 7,850,733 B2 | 12/2010 | Baynham et al. |
| 7,862,618 B2 | 1/2011 | White et al. |
| 7,879,098 B1 | 2/2011 | Simmons, Jr. |
| 7,909,872 B2 | 3/2011 | Zipnick |
| 7,918,888 B2 | 4/2011 | Hamada |
| 8,062,375 B2 | 11/2011 | Glerum et al. |
| 8,070,754 B2 | 12/2011 | Fabian et al. |
| 8,070,813 B2 | 12/2011 | Grotz et al. |
| 8,083,744 B2 | 12/2011 | Dorchak |
| 8,088,163 B1 | 1/2012 | Kleiner |
| 8,105,382 B2 | 1/2012 | Olmos et al. |
| 8,110,004 B2 | 2/2012 | Valdevit et al. |
| 8,118,870 B2 | 2/2012 | Gordon et al. |
| 8,123,810 B2 | 2/2012 | Gordon et al. |
| 8,167,950 B2 | 5/2012 | Aferzon et al. |
| 8,182,538 B2 | 5/2012 | O'Neil et al. |
| 8,187,332 B2 | 5/2012 | McLuen |
| 8,236,058 B2 | 8/2012 | Fabian et al. |
| 8,241,363 B2 | 8/2012 | Sommerich et al. |
| 8,267,939 B2 | 9/2012 | Cipoletti et al. |
| 8,353,961 B2 | 1/2013 | McClintock |
| 8,353,963 B2 | 1/2013 | Glerum |
| 8,398,713 B2 | 3/2013 | Weiman |
| 8,435,298 B2 | 5/2013 | Weiman |
| 8,491,659 B2 | 7/2013 | Weiman et al. |
| 8,518,120 B2 | 8/2013 | Glerum et al. |
| 8,551,173 B2 | 10/2013 | Lechmann et al. |
| 8,556,979 B2 | 10/2013 | Glerum et al. |
| 8,628,578 B2 | 1/2014 | Miller et al. |
| 8,632,595 B2 | 1/2014 | Weiman |
| 8,663,332 B1 | 3/2014 | To |
| 8,685,098 B2 | 4/2014 | Glerum et al. |
| 8,845,731 B2 | 9/2014 | Weiman |
| 8,852,279 B2 | 10/2014 | Weiman et al. |
| 8,926,704 B2 | 1/2015 | Glerum et al. |
| 8,936,641 B2 | 1/2015 | Cain |
| 8,940,048 B2 | 1/2015 | Butler et al. |
| 8,940,052 B2 | 1/2015 | Lechmann et al. |
| 8,986,387 B1 | 3/2015 | To |
| 9,034,041 B2 | 5/2015 | Wolters |
| 9,039,771 B2 | 5/2015 | Glerum et al. |
| 9,044,342 B2 | 6/2015 | Perloff et al. |
| 9,060,876 B1 * | 6/2015 | To ..................... A61F 2/447 |
| 9,138,328 B2 | 9/2015 | Butler et al. |
| 9,155,628 B2 | 10/2015 | Glerum et al. |
| 9,186,259 B2 | 11/2015 | To |
| 9,216,095 B2 | 12/2015 | Glerum et al. |
| 9,241,806 B2 | 1/2016 | Suh |
| 9,278,008 B2 | 3/2016 | Perloff et al. |
| 9,320,610 B2 | 4/2016 | Alheidt et al. |
| 9,333,092 B2 | 5/2016 | To |
| 9,351,848 B2 | 5/2016 | Glerum et al. |
| 9,402,733 B1 | 8/2016 | To |
| 9,402,739 B2 | 8/2016 | Weiman et al. |
| 9,421,110 B2 | 8/2016 | Masson |
| 9,445,918 B1 | 9/2016 | Lin et al. |
| 9,463,052 B2 | 10/2016 | Geist |
| 9,474,625 B2 | 10/2016 | Weiman |

(56) References Cited

U.S. PATENT DOCUMENTS

| | | |
|---|---|---|
| 9,480,574 B2 | 11/2016 | Lee et al. |
| 9,480,576 B2 | 11/2016 | Pepper et al. |
| 9,545,316 B2 | 1/2017 | Ashley et al. |
| 9,561,116 B2 | 2/2017 | Weiman et al. |
| 9,566,168 B2 | 2/2017 | Glerum et al. |
| 9,636,154 B2 | 5/2017 | Overes et al. |
| 9,655,744 B1 | 5/2017 | Pimenta |
| 9,675,469 B2 | 6/2017 | Landry et al. |
| 9,717,601 B2 | 8/2017 | Miller |
| 9,737,411 B2 | 8/2017 | Loebl et al. |
| 9,795,493 B1 | 10/2017 | Bannigan |
| 9,801,640 B2 | 10/2017 | O'Neil et al. |
| 9,801,733 B2 | 10/2017 | Wolters et al. |
| 9,801,734 B1 | 10/2017 | Stein et al. |
| 9,883,953 B1 | 2/2018 | To |
| 9,889,019 B2 | 2/2018 | Rogers et al. |
| 9,907,673 B2 | 3/2018 | Weiman et al. |
| 9,913,727 B2 | 3/2018 | Thommen et al. |
| 9,913,736 B2 | 3/2018 | To |
| 9,987,143 B2 | 6/2018 | Robinson et al. |
| 9,999,517 B2 | 6/2018 | To |
| 10,052,215 B2 | 8/2018 | Hessler et al. |
| 10,058,350 B2 | 8/2018 | Geist |
| 10,080,592 B2 | 9/2018 | Geist |
| 10,085,849 B2 | 10/2018 | Weiman et al. |
| 10,098,757 B2 | 10/2018 | Logan et al. |
| 10,105,238 B2 | 10/2018 | Koch et al. |
| 10,143,569 B2 | 12/2018 | Weiman et al. |
| 10,149,773 B2 | 12/2018 | To |
| 10,154,911 B2 | 12/2018 | Predick et al. |
| 10,426,634 B1 | 2/2019 | Al-Jazaeri et al. |
| 10,226,356 B2 | 3/2019 | Grotz |
| 10,226,360 B2 | 3/2019 | Baynham |
| 10,238,503 B2 | 3/2019 | Kuyler et al. |
| 10,251,759 B2 | 4/2019 | Butler et al. |
| 10,265,192 B2 | 4/2019 | Eastlack et al. |
| 10,322,014 B2 | 6/2019 | To |
| 10,342,675 B2 | 7/2019 | Alheidt |
| 10,413,419 B2 | 9/2019 | Thibodeau |
| 10,441,430 B2 | 10/2019 | Ludwig et al. |
| 10,470,891 B2 | 11/2019 | Sharifi-Mehr et al. |
| 10,470,894 B2 | 11/2019 | Foley et al. |
| 10,485,675 B2 | 11/2019 | Sharifi-Mehr et al. |
| 10,531,964 B2 | 1/2020 | Miller et al. |
| 10,624,756 B2 | 4/2020 | Bernard et al. |
| 10,631,996 B2 | 4/2020 | Bernard et al. |
| 2002/0040243 A1 | 4/2002 | Attali |
| 2003/0074075 A1 | 4/2003 | Thomas et al. |
| 2003/0083746 A1 | 5/2003 | Kuslichi |
| 2004/0010315 A1 | 1/2004 | Song |
| 2004/0024463 A1 | 2/2004 | Thomas et al. |
| 2005/0256576 A1 | 11/2005 | Moskowitz et al. |
| 2006/0100706 A1 | 5/2006 | Shadduck |
| 2006/0122701 A1 | 6/2006 | Kiester |
| 2006/0167547 A1 | 7/2006 | Suddaby |
| 2006/0287729 A1 | 12/2006 | Segal et al. |
| 2007/0118222 A1 | 5/2007 | Lang |
| 2007/0173939 A1 | 7/2007 | Kim et al. |
| 2007/0219634 A1 | 9/2007 | Greenhalgh |
| 2008/0009876 A1 | 1/2008 | Sankaran et al. |
| 2008/0021556 A1 | 1/2008 | Edie |
| 2008/0021559 A1 | 1/2008 | Thramann |
| 2008/0147193 A1 | 6/2008 | Matthis |
| 2008/0234687 A1 | 9/2008 | Schaller |
| 2008/0281346 A1 | 11/2008 | Greenhalgh |
| 2008/0281424 A1 | 11/2008 | Parry et al. |
| 2009/0018524 A1 | 1/2009 | Greenhalgh |
| 2009/0076607 A1 | 3/2009 | Aalsma et al. |
| 2009/0138083 A1 | 5/2009 | Biyani |
| 2009/0281551 A1 | 5/2009 | Frey |
| 2009/0222043 A1 | 9/2009 | Altarac |
| 2009/0234389 A1 | 9/2009 | Chuang |
| 2010/0010542 A1 | 1/2010 | Jackson |
| 2010/0010633 A1 | 1/2010 | Kohm |
| 2010/0042218 A1 | 2/2010 | Nebosky et al. |
| 2010/0198352 A1 | 8/2010 | Edie |
| 2010/0217325 A1 | 8/2010 | Hochschuler |
| 2010/0222884 A1 | 9/2010 | Greenhalgh |
| 2010/0234956 A1 | 9/2010 | Attia |
| 2010/0286783 A1 | 11/2010 | Lechmann et al. |
| 2010/0292796 A1 | 11/2010 | Greenhalgh |
| 2011/0022090 A1 | 1/2011 | Gordon |
| 2011/0029082 A1 | 2/2011 | Hall |
| 2011/0046748 A1 | 2/2011 | Martin |
| 2011/0130835 A1 | 6/2011 | Ashley |
| 2011/0172774 A1 | 7/2011 | Varela |
| 2011/0190816 A1 | 8/2011 | Sheffer |
| 2011/0282453 A1 | 11/2011 | Greenhalgh |
| 2011/0301712 A1 | 12/2011 | Palmatier |
| 2011/0319997 A1* | 12/2011 | Glerum .................. A61F 2/442 623/17.15 |
| 2012/0029636 A1 | 2/2012 | Ragab |
| 2012/0035729 A1 | 2/2012 | Glerum et al. |
| 2012/0046748 A1 | 2/2012 | Weiman |
| 2012/0083889 A1 | 4/2012 | Purcell |
| 2012/0089185 A1 | 4/2012 | Gabelberger |
| 2012/0109319 A1 | 5/2012 | Perisic |
| 2012/0209386 A1 | 8/2012 | Triplett et al. |
| 2012/0271396 A1 | 10/2012 | Zheng |
| 2012/0290090 A1 | 11/2012 | Glerum et al. |
| 2012/0303126 A1 | 11/2012 | Kirschman |
| 2013/0023996 A1 | 1/2013 | McCormack |
| 2013/0184822 A1 | 7/2013 | Kleiner |
| 2014/0039625 A1 | 2/2014 | To |
| 2014/0243981 A1 | 8/2014 | Davenport et al. |
| 2015/0100128 A1 | 4/2015 | Glerum et al. |
| 2015/0148908 A1* | 5/2015 | Marino ............... A61F 2/30771 623/17.16 |
| 2015/0190242 A1 | 7/2015 | Blain et al. |
| 2015/0374508 A1 | 12/2015 | Sandul |
| 2016/0015530 A1 | 1/2016 | To |
| 2016/0256291 A1 | 9/2016 | Miller |
| 2016/0317315 A1 | 11/2016 | Weiman |
| 2016/0338854 A1 | 11/2016 | Serhan et al. |
| 2017/0119540 A1 | 5/2017 | Greenhalgh |
| 2017/0209282 A1 | 7/2017 | Aghayev et al. |
| 2017/0224504 A1 | 8/2017 | Butler et al. |
| 2017/0224505 A1 | 8/2017 | Butler et al. |
| 2017/0231780 A1 | 8/2017 | D'urso |
| 2017/0239063 A1 | 8/2017 | Predick |
| 2017/0281358 A1 | 10/2017 | Wagner et al. |
| 2017/0333198 A1 | 11/2017 | Robinson |
| 2017/0333203 A1 | 11/2017 | Glerum |
| 2017/0354512 A1 | 12/2017 | Weiman et al. |
| 2018/0042735 A1 | 2/2018 | Schell et al. |
| 2018/0214221 A1 | 3/2018 | Crawford et al. |
| 2018/0098860 A1 | 4/2018 | To |
| 2018/0185163 A1* | 7/2018 | Weiman ............... A61F 2/4611 |
| 2018/0193164 A1 | 7/2018 | Shoshtaev |
| 2018/0256357 A1 | 9/2018 | To |
| 2018/0296361 A1 | 10/2018 | Butler et al. |
| 2018/0360489 A1 | 12/2018 | Geist |
| 2018/0360617 A1 | 12/2018 | Fabian et al. |
| 2019/0053913 A1 | 2/2019 | To |
| 2019/0060085 A1 | 2/2019 | Geist |
| 2019/0076263 A1 | 3/2019 | Emstad |
| 2019/0091033 A1 | 3/2019 | Dewey et al. |
| 2019/0201209 A1 | 3/2019 | Branch et al. |
| 2019/0099278 A1 | 4/2019 | Farris et al. |
| 2019/0110900 A1 | 4/2019 | Suddaby |
| 2019/0110902 A1 | 4/2019 | Vigliotti et al. |
| 2019/0117409 A1 | 4/2019 | Shoshtaev |
| 2019/0117827 A1 | 4/2019 | Roth |
| 2019/0290448 A1 | 6/2019 | Predick et al. |
| 2019/0240039 A1 | 8/2019 | Walker et al. |
| 2019/0254836 A1 | 8/2019 | Cowan et al. |
| 2019/0307573 A1 | 10/2019 | Sicotte et al. |
| 2019/0336299 A1 | 11/2019 | Bernard et al. |
| 2020/0015985 A1 | 1/2020 | Rogers et al. |
| 2020/0030110 A1 | 1/2020 | Sharabani et al. |
| 2020/0046515 A1 | 2/2020 | To |

(56) References Cited

U.S. PATENT DOCUMENTS

| | | | |
|---|---|---|---|
| 2020/0093609 | A1 | 3/2020 | Shoshtaev |
| 2020/0229939 | A1 | 7/2020 | To |

FOREIGN PATENT DOCUMENTS

| | | |
|---|---|---|
| EP | 1233732 | 2/2001 |
| EP | 2327377 | 3/2002 |
| EP | 1532949 | 11/2003 |
| EP | 2237748 | 1/2009 |
| JP | 2009/505686 | 7/2005 |
| WO | WO 1996/040015 | 6/1996 |
| WO | WO 2000/044319 | 1/2000 |
| WO | WO 2001/066047 | 7/2001 |
| WO | WO 2008/005627 | 5/2007 |
| WO | WO 2007/076374 | 7/2007 |
| WO | WO 2008/035849 | 7/2007 |
| WO | WO 2008/033457 | 3/2008 |
| WO | WO 2008/089252 | 7/2008 |
| WO | WO 2008/121162 | 10/2008 |
| WO | WO 2010/077359 | 7/2010 |
| WO | WO 2012/135764 | 10/2012 |

OTHER PUBLICATIONS

U.S. Appl. No. 16/403,576, filed Sep. 9, 2013, To—owned by Applicant.
U.S. Appl. No. 16/444,888, filed Dec. 13, 2012, To—owned by Applicant.
U.S. Appl. No. 60/666,945 (priority for U.S. Pat. No. 7,731,751, cited herein), filed Mar. 31, 2005, Butler, et al.
U.S. Appl. No. 61/585,724 (priority for U.S. Pat. No. 9,463,052, cited herein), filed Jan. 12, 2012, Geist—owned by Applicant.
U.S. Appl. No. 61/737,054, filed Dec. 15, 2013, To—owned by Applicant.
U.S. Appl. No. 61/875,688, filed Oct. 4, 2013, To—owned by Applicant.
U.S. Appl. No. 62/232,021 (priority for U.S. Pat. No. 10,058,350, cited herein), filed Sep. 24, 2015, Geist—owned by Applicant.
U.S. Appl. No. 62/444,663 (priority for U.S. 2018/0193164, cited herein), filed Jan. 20, 2017, Shoshtaev—owned by Applicant.
U.S. Appl. No. 62/471,206 (priority for U.S. 2018/0193164, cited herein), filed Jan. 10, 2017, Shoshtaev—owned by Applicant.
U.S. Appl. No. 62/481,565 (priority for U.S. 2018/0193164, cited herein), filed Jan. 10, 2017, Shoshtaev—owned by Applicant.
U.S. Appl. No. 62/536,335 (priority for PCT/US2018/43517, cited herein), filed Jul. 24, 2017, To—owned by Applicant.
U.S. Appl. No. 62/550,557 (priority for U.S. Appl. No. 16/113,040, cited herein), filed Aug. 25, 2017, Geist—owned by Applicant.
PCT/US2013/052799, To—owned by Applicant, Jul. 31, 2012.
Written opinion and search report for PCT/US2013/052799, To—owned by Applicant, dated Dec. 2, 2012.
PCT/US2013/073435 Published as WO 2014/093136, To—owned by Applicant, Dec. 5, 2013.
Written opinion and search report for PCT/US2013/073435, To—owned by Applicant, dated Apr. 30, 2012.
PCT/US2014/054437, To—owned by Applicant, Feb. 26, 2014.
Written opinion and search report for PCT/US2014/054437, To—owned by Applicant, dated Jan. 6, 2015.
PCT/US2016/014100, To—owned by Applicant, Dec. 17, 2015.
Written opinion and search report for PCT/US2016/014100, To—owned by Applicant, dated Jan. 6, 2015.
PCT/US2017/52708, To—owned by Applicant, Sep. 21, 2017.
Written opinion and search report for PCT/US2017/52708, To—owned by Applicant, dated Sep. 21, 2017.
PCT/US2016/053467 Published as WO 2017/053813, Geist—owned by Applicant, Sep. 24, 2015.
Written opinion and search report for PCT/US2016/053467, Geist—owned by Applicant, dated Sep. 24, 2015.
PCT/US2018/13207 Published as WO 2018/132502, Shoshtaev—owned by Applicant, Jan. 10, 2018.

Written opinion and search report for PCT/US2018/13207, Shoshtaev—owned by Applicant, dated Jan. 10, 2018.
PCT/US2018/43517, To—owned by Applicant, Jul. 24, 2018.
Written opinion and search report for PCT/US2018/43517, To—owned by Applicant, dated Jul. 24, 2018.
PCT/US2019/20354, Shoshtaev—owned by Applicant, Mar. 1, 2018.
Written opinion and search report for PCT/US2019/20354, Shoshtaev—owned by Applicant, dated Mar. 1, 2018.
European search report for EP 13862126, dated Dec. 5, 2013, To—owned by Applicant.
European search report for EP 14842880, dated Jun. 22, 2016, To—owned by Applicant.
European search report for EP 16740662, dated Nov. 29, 2017, To—owned by Applicant.
Basho, R. et al. Lateral interbody fusion: Indications and techniques. Operative techniques in orthopaedics 21(3): 204-207 (Sep. 2011).
Caliber. www.globusmedical.com [online] URL: http://www.globusmedical.com/mis/166-caliber [retrieved on Jul. 27, 2012].
Cole, D. et al. Comparison of low back fusion techniques: transforaminal lumbar interbody fusio (TLIF) or posterior lumbar interbody fusion (PLIF) approaches. Curr rev Musculoskelet med 2(2): 118-126 published online Apr. 29, 2009 Doi: 1007/s12178-009-9053-B10 [retrieved Jun. 2009].
CAPSTONE® PEEK spinal system PLIF anf TLIF surgical technique. Medtronic Sofamor Danek 1-36 (2009).
Coalign. Introducing AccuLIF expandable lumbar interbody fusion technology. [online] URL: http://www.coalign.com [retrieved on Jul. 27, 2012].
Chapman, C. A. Design of an expandable intervertebral cage utilizing shape memory alloys. University of Toledo and OhioLINK, 2011. [online] URL: http://etd.ohiolink.edu/view.cgi?acc_num=toledo1302226375 [retrieved Feb. 13, 2013].
Dorso-Lumbar Vertebral Body Cages DSC, Sintea Plustek. [online] URL: http://www.sinteaplustek.com/spine_dsc_eng.html [retrieved on Feb. 13, 2013].
"Integrity Implants" (Integrity Implants) URL: http://www.integrityimplants.com/ [retrieved from internet Sep. 17, 2018].
"Integrity Implants v3" (Integrity Implants) URL: https://vimeo.com/232697959 ; [retrieved from the internet Nov. 16, 2017].
Interbody Fusion Cage (Neo IC) Source, www.tradekorea.com [online] URL: http://www.tradekorea.com/product-detail/P00015150/Interbody_Fusion_Cage_Neo_IC_.html [retrieved Feb. 13, 2013].
Kaech, D.L. et al. Spinal restabilization procedures, diagnostic and therapeutic aspects of intervertebral fusion cages, artificial discs and mobile implants. Elsevier Science B.V. Part II: 121-204(2002).
Kiapour, A. et al. A biomechanical finite element study of subsidence and migration tendencies in stand-alone fusion procedures—comparison of an in situ expandable device with a rigid device. J Spine 1(4): 5 pages (2012).
Le Huec, J.C. et al. Endoscope surgery of the spine, a review of 4 years? Practice, maltrise orthopaedique. Jan. 1999 [online] URL: http://www.maitrise-orthop.com/viewPage_us.do?id=435 [retrieved on Feb. 5, 2013].
Powerbuilt. Powerbuilt 940378 medium tailpipe expander set. [online] URL: http://www.amazon.com/Powerbuilt-940377-Tailpipi-Expander-Series/dp/B004KED6A [retrieved on Feb. 17, 2013].
PR Newswire. Benvenue Medical starts enrolling patients in the post-market lift study on the luna interbody spacer system for degenerative disc disease. Mar. 20, 2012, [online] URL: http://www.prnewswire.com/news-releases/benvenue-medical-starts-enrolling-patients-in-the-post-market-lift-study-on-the-luna-interbody-spacer-system-for-degenerative-disc-disease-143441246.html [retrieved on Jan. 27, 2013].
Sasani, M. et al. Single-stage posterior corpectomy and expandable cage placement for treatment of thoracic or lumbar burst fractures. Spine 34(1): E33-E40 (Jan. 1, 2009).
Spineology. OptiMesh 1500E deploying grafting system. [online] URL: http://www.spineology.com/fb/intl/products/products/optimesh 1500e.html (retrieved Jun. 3, 2013).
STAXX XD, www.spinewave.com. [online] URL: http://www.spinewave.com/products/xd_us.html [retrieved on Jan. 27, 2013].

(56) References Cited

OTHER PUBLICATIONS

SynFix-LR System. Instruments and implants for stand-alone anterior lumbar interbody fusion (ALIF). Synthes SynFix-LR system technique guide 52 pages (2010).

Transforaminal Lumbar Interbody Fusion (TLIF). Virgina spine institute, Reston Virgina. [online] URL: http://www.spinemd.com/operative-treatments/tlif-transforaminal-lumbat-interbody-fusion.com 1-6 (2013). [retrieved on Jun. 16, 2013].

Uchida, K. et al. Anterior expandable strut cage replacement for osteoporotic thoracolumbar vertebral collapse. J Neurosurg Spine 4(6): 454-462 (Jun. 2006).

XENOS. Cage mesh system for spine. Biotek Chetan Meditech Pvt. Ltd. [online] URL: http://www.biotekortho.net/spine-treatment.html [retrieved on Feb. 13, 2013].

ZEUS-O, [online] URL: http://www.amendia.com/zeuso.html [retrieved on Jan. 27, 2013].

U.S. Appl. No. 16/932,064, filed Jan. 20, 2015, To—owned by Applicant.

European search report for EP 17853887.2, dated Jul. 31, 2019, To—owned by Applicant.

European search report for EP 19162909.6, dated Dec. 5, 2013, To—owned by Applicant.

\* cited by examiner

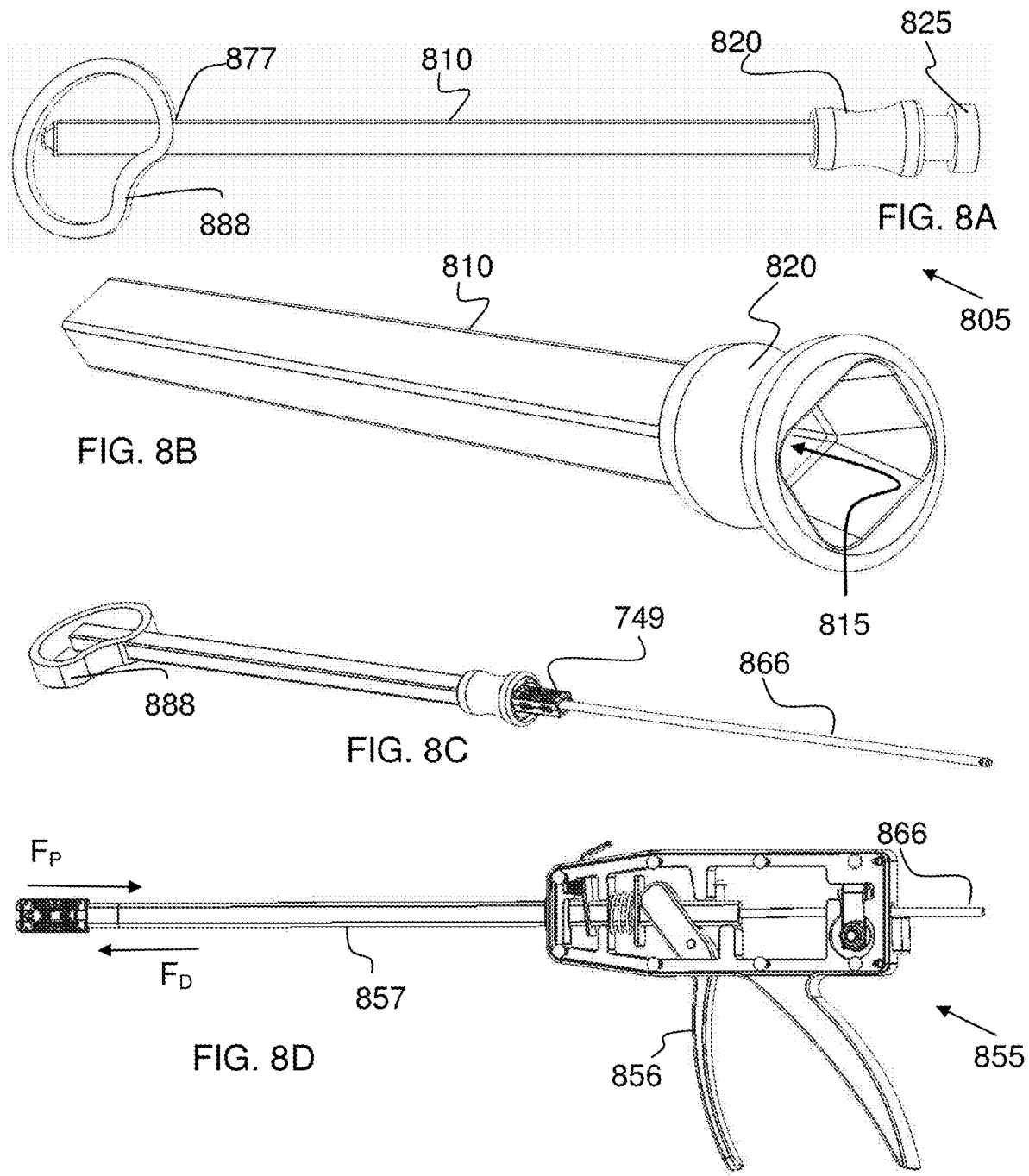

FIG. 10A
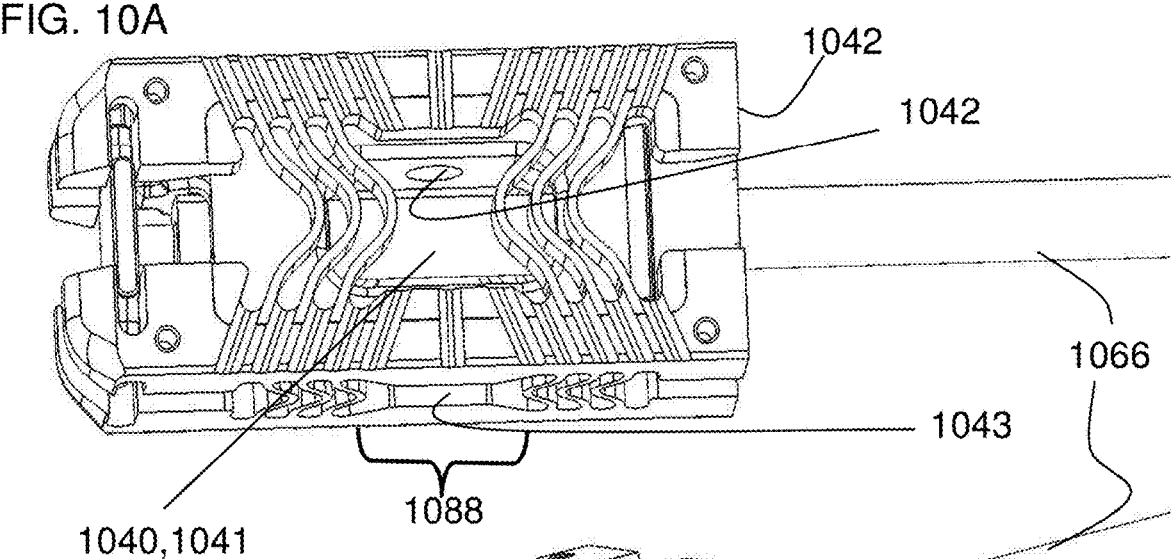
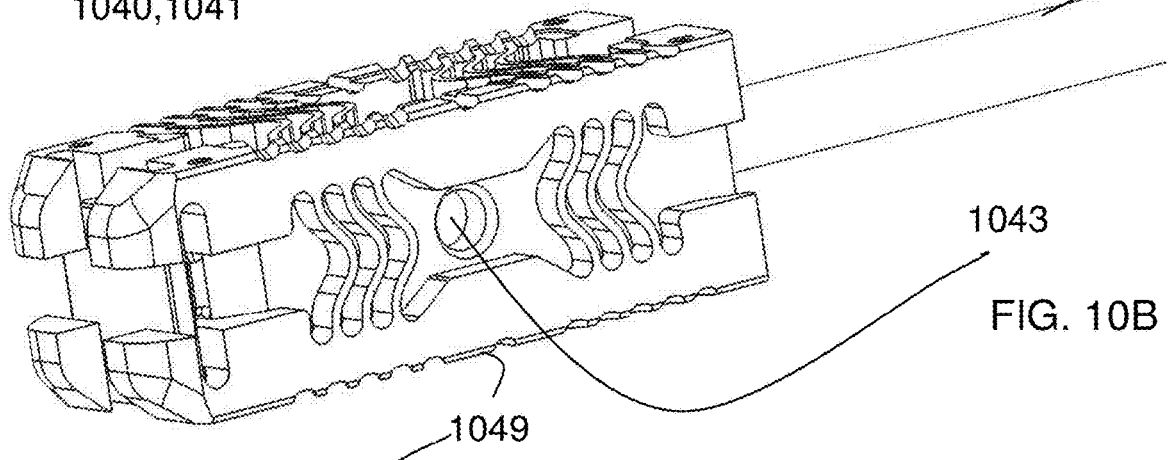
FIG. 10B
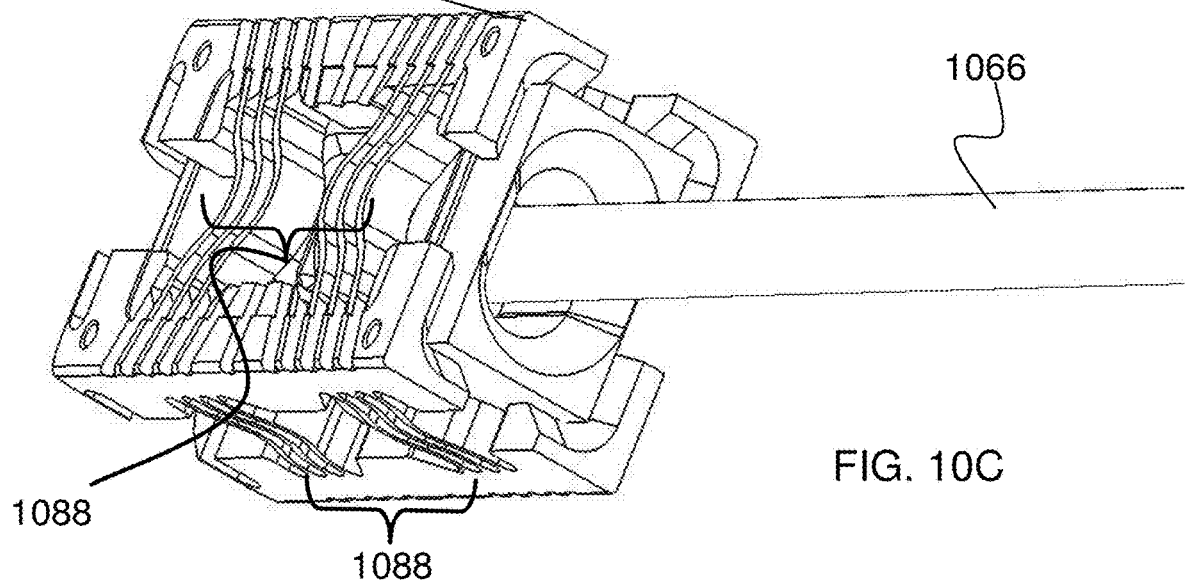
FIG. 10C

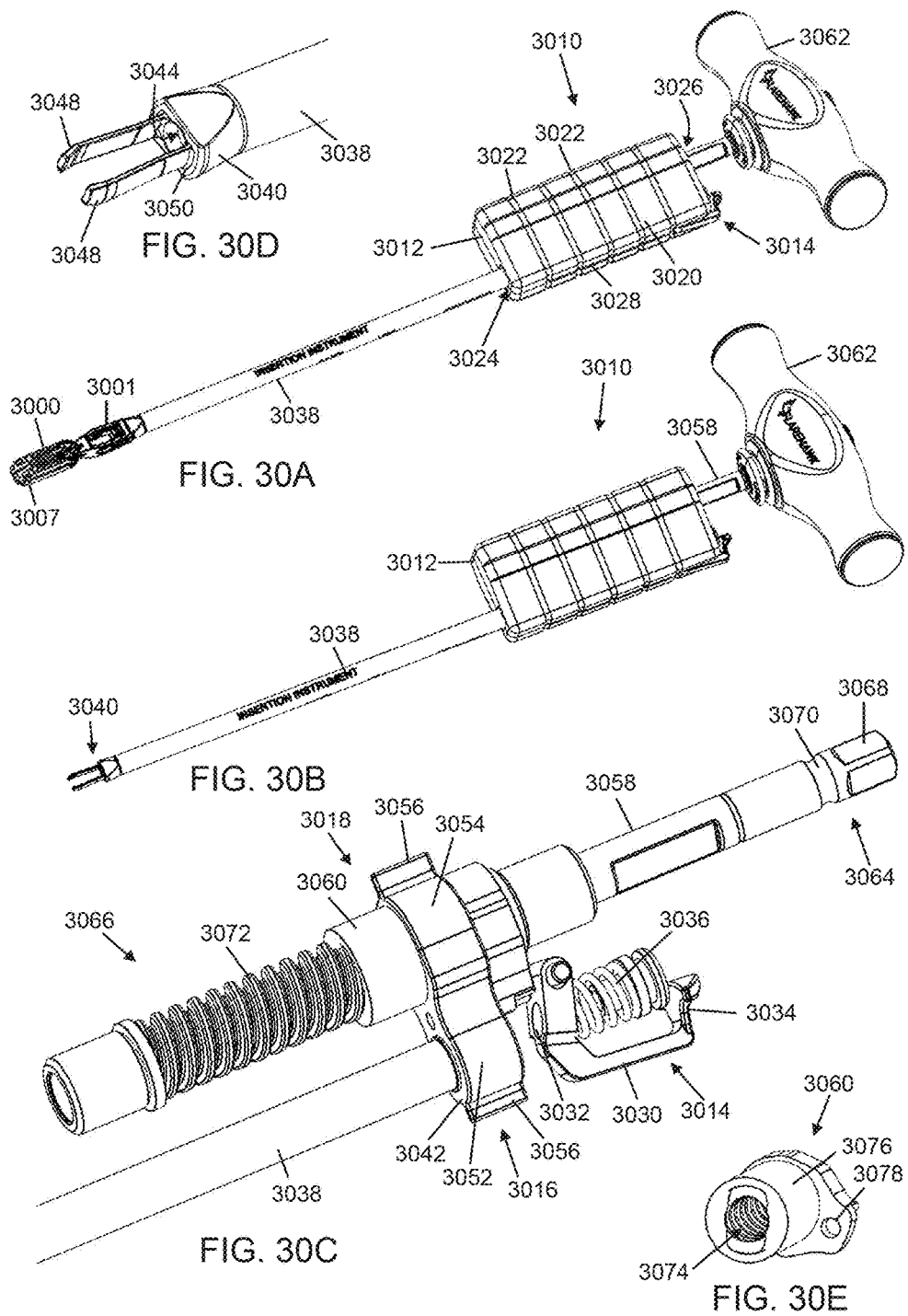

STABILIZED LATEROVERTICALLY-EXPANDING FUSION CAGE SYSTEMS WITH TENSIONER

CROSS-REFERENCE TO RELATED APPLICATIONS

This application is a national stage entry from International Application No. PCT/US17/52708, filed Sep. 21, 2017, which claims priority to U.S. application Ser. No. 15/271,741, filed Sep. 21, 2016, now U.S. Pat. No. 9,883,953, each of which is hereby incorporated herein by reference in its entirety.

BACKGROUND

Field of the Invention

The teachings herein are directed to intervertebral scaffolding systems having a combination of a stabilizer and a tensioner for stabilizing and/or retaining support beams upon expansion of the scaffolding in an intervertebral disc space.

Description of the Related Art

Bone grafts are used in spinal fusion, for example, which is a technique used to stabilize the spinal bones, or vertebrae, and a goal is to create a solid bridge of bone between two or more vertebrae. The fusion process includes "arthrodesis", which can be thought of as the mending or welding together of two bones in a spinal joint space, much like a broken arm or leg healing in a cast. Spinal fusion may be recommended for a variety of conditions that might include, for example, a spondylolisthesis, a degenerative disc disease, a recurrent disc herniation, or perhaps to correct a prior surgery.

Bone graft material is introduced for fusion and a fusion cage can be inserted to help support the disc space during the fusion process. In fact, fusion cages are frequently used in such procedures to support and stabilize the disc space until bone graft unites the bone of the opposing vertebral endplates in the disc space. A transforaminal lumbar interbody fusion (TLIF), for example, involves placement of posterior instrumentation (screws and rods) into the spine, and the fusion cage loaded with bone graft can be inserted into the disc space. Bone graft material can be pre-packed in the disc space or packed after the cage is inserted. TLIF can be used to facilitate stability in the front and back parts of the lumbar spine promoting interbody fusion in the anterior portion of the spine. Fusion in this region can be beneficial, because the anterior interbody space includes an increased area for bone to heal, as well as to handle increased forces that are distributed through this area.

Unfortunately, therein lies a problem solved by the teachings provided herein. Currently available systems can be problematic in that the methods of introducing the fusion cage and bone graft material leaves pockets in regions of the intervertebral space that are not filled with bone graft material, regions in which fusion is desired for structural support. These pockets can create a premature failure of the fused intervertebral space due to forces that are distributed through the regions containing the pockets, for example, when the patient stands and walks.

Traditional fusion cages, such as the Medtronic CAPSTONE cage, are designed to be oversized relative to the disc space to distract the disc space as the entire cage is inserted. However, this makes it difficult to insert and position properly. In response to the problem, the art has developed a number of new fusion cages, such as the Globus CALIBER cage which can be inserted at a low height and expanded vertically to distract the disc space. Unfortunately, these types of devices have the typical graft distribution problem discussed above, in that they do not provide a path for bone graft to be inserted and fill in the space surrounding the cage or within the cage. They have other problems as well, including that the annulotomy must be large to accommodate a large enough cage for stability, and this large opening necessitates more trauma to the patient. Moreover, they can also create the additional problem of "backout", in that they cannot expand laterally beyond the annulotomy to increase the lateral footprint of the cage relative to lateral dimension of the annulotomy. Since it takes several months for the fusion to occur to completion in a patient, the devices have plenty of time to work their way out of the space through the large annulotomy.

Scaffolding systems may also suffer a lack of stability and/and or a lack of a retention of structural components in a desired expansion configuration in the intervertebral space. As such, a multi-component scaffolding system, for example, can benefit from an improved design that adds stability through, for example, (i) enhancing the amount of contact between the scaffolding components upon expansion; and/or (ii) limiting the amount of expansion, or relative movement, that can occur between components upon expansion, or after expansion, in the intervertebral space. Such design considerations can, for example, address the problems of overexpansion of one component relative to another due to, for example, variable stresses that might occur in the intervertebral space upon expansion or after expansion, stresses which can result in at least partial failure of the scaffolding system in the intervertebral space.

Accordingly, and for at least the above reasons, those of skill in the art will appreciate bone graft distribution systems that facilitate an improved distribution of graft material throughout the intervertebral space. Such systems are provided herein, the systems configured to (i) effectively distribute bone graft material both from the system, and around the system, to improve the strength and integrity of a fusion; (ii) reduce or eliminate the problem of failures resulting from a poor bone graft distribution; (iii) have a small maximum dimension in a collapsed state for a low-profile insertion into the annulus in a minimally-invasive manner, whether using only a unilateral approach or a bilateral approach; (iv) laterally expand within the intervertebral space to avoid backout of the system through the annulotomy; (v) vertically expand for distraction of the intervertebral space; (vi) provide an expansion in the intervertebral space without contracting the system in length to maintain a large footprint and an anterior position adjacent to the inner, anterior annulus wall, distributing load over a larger area, anteriorly, against the endplates; (vii) and, incorporate a stabilizer for stabilizing and/or retaining support beams upon expansion of the scaffolding in an intervertebral disc space.

SUMMARY

The teachings herein are directed to intervertebral scaffolding systems having a combination of a stabilizer and/or one or more tensioners for stabilizing and/or retaining support beams upon expansion of the scaffolding in an intervertebral disc space. As such, the teachings herein are generally directed to an intervertebral scaffolding system.

The systems provided herein can comprise, for example, a central beam having a central beam axis; a proximal portion and a distal portion; a top surface with a first top-lateral surface and a second top-lateral surface; a bottom surface with a first bottom-lateral surface and a second bottom-lateral surface; a first side surface with a first top-side surface and a first bottom-side surface; and, a second side surface with a second top-side surface and a second bottom-side surface. The systems can also comprise a laterovertically-expanding frame configured for operably contacting the central beam to create an intervertebral scaffolding system in vivo. The frame can have a collapsed state and an expanded state, the expanded state operably contacting with the central beam in the intervertebral space; a proximal portion having an end, a distal portion having an end, and a central frame axis of the expanded state.

In some embodiments, the frame can be constructed to have a first top beam including a proximal portion having an end and a distal portion having an end, the first top beam configured for contacting the first top-lateral surface of the central beam and the first top-side surface of the central beam in the expanded state, a central axis of the first top beam at least substantially on (i) a top plane containing the central axis of the first top beam and a central axis of a second top beam and (ii) a first side plane containing the central axis of the first top beam and a central axis of a first bottom beam; the second top beam including a proximal portion having an end and a distal portion having an end, the second top beam configured for contacting the second top-lateral surface of the central beam and the second top-side surface of the central beam in the expanded state, the central axis of the second top beam at least substantially on (i) the top plane and (ii) a second side plane containing the central axis of the second top beam and a central axis of a second bottom beam; the first bottom beam including a proximal portion having an end and a distal portion having an end, the first bottom beam configured for contacting the first bottom-lateral surface of the central beam and the first bottom-side surface of the central beam in the expanded state, the central axis of the first bottom beam at least substantially on (i) a bottom plane containing the central axis of the first bottom beam and the central axis of the second top beam and (ii) the first side plane; the second bottom beam including a proximal portion having an end and a distal region having an end, the second bottom beam configured for contacting the second bottom-lateral surface of the central beam and the second bottom-side surface of the central beam in the expanded state, the central axis of the second bottom beam being at least substantially on (i) the bottom plane and (ii) a second side plane containing the central axis of the second bottom beam and the central axis of the second top beam.

The frame can also be constructed, for example, to have a plurality of top connector elements configured to expandably connect the first top beam to the second top beam, the expanding consisting of a flexing at least substantially on the top plane; a plurality of bottom connector elements configured to expandably connect the first bottom beam to the second bottom beam, the expanding consisting of a flexing at least substantially on the bottom plane; a plurality of first side connector elements configured to expandably connect the first top beam to the first bottom beam, the expanding consisting of a flexing at least substantially on the first side plane; and, a plurality of second side connector elements configured to expandably connect the second top beam to the second bottom beam, the expanding consisting of a flexing at least substantially on the second side plane In some embodiments, the systems include a stabilizer that slidably engages with the distal region of the first top beam, the first bottom beam, the second top beam, the second bottom beam, or a combination thereof. The stabilizer can be configured for retaining the first top beam, the first bottom beam, the second top beam, the second bottom beam, or the combination thereof, from a lateral movement that exceeds the expanded state.

In some embodiments, the framing can be configured to include one or more tensioners, for example, a top tensioner operably attaching the first top beam to the second top beam; and, a bottom tensioner operably attaching the first bottom beam to the second bottom beam. The one or more tensioners can be used in combination with the stabilizer.

And, in some embodiments, the framing can be configured for engaging with the central beam in vivo to support the framing in the expanded state. Moreover, the connector elements can be struts configured to have a cross-sectional aspect ratio of longitudinal thickness to transverse thickness ranging from 1:2 to 1:8, adapted to maintain structural stiffness in the laterovertically expanding frame in a direction perpendicular to the central frame axis of the expanded state of the frame.

The stabilizer can be in an X-configuration. In some embodiments, the X-configuration can have a first top leg for slidably-engaging with the first top beam at an angle $\theta_{1T}$ with the lateral movement of the first top beam, first bottom leg for slidably engaging with the first bottom beam at an angle $\theta_{1B}$ with the lateral movement of the first bottom beam, a second top leg for slidably engaging with the second top beam at an angle $\theta_{2T}$ with the lateral movement of the second top beam, and a second bottom leg for slidably engaging with the second bottom beam at an angle $\theta_{2B}$ with the lateral movement of the second bottom beam. In some embodiments, each of the angles $\theta_{1T}$, $\theta_{1B}$, $\theta_{2T}$, $\theta_{2B}$, respectively, provide a tensile force for resisting the first top beam, the first bottom beam, the second top beam, and the second bottom beam from the lateral movement that exceeds the expanded state. In some embodiments, the stabilizer further comprises a point of attachment for releasably attaching a guidewire for guiding the central beam into the laterovertically expanding frame. And, in some embodiments, the first top leg, the first bottom leg, the second top leg, and the second bottom leg converge to form a hub having a point of attachment for releasably attaching a guidewire for guiding the central beam into the laterovertically expanding frame.

The stabilizer can be in an H-configuration. The H-configuration can have a first vertical leg, a second vertical leg, and a cross-member that connects the first vertical leg at least substantially parallel to the second vertical leg, the first vertical leg including a retaining surface for engaging with the first top beam and the first bottom beam, the second vertical leg including a retaining surface for engaging with the second top beam and the second bottom beam, and the cross-member providing a tensile force for resisting the first top beam, the first bottom beam, the second top beam, and the second bottom beam from the lateral movement that exceeds the expanded state. In some embodiments, the central beam has a horizontal groove configured complementary to the cross-member of the stabilizer, and the horizontal groove of the central beam slidably connects with the cross-member in the expanded state. In some embodiments, the cross-member further comprises a vertical support member and the central beam has a vertical groove configured complementary to the vertical support member of the stabilizer, and the vertical groove of the central beam slidably connects with the vertical support member in the expanded state. In some embodiments, the stabilizer further comprises a point of attachment for releasably attaching a guidewire adapted for guiding the central beam into the laterovertically expanding frame. And, in some embodiments, cross-member includes a first pillar and a second pillar that operably connect at a hub that has a point of attachment for releasably attaching a guidewire for guiding the central beam into the laterovertically expanding frame.

In some embodiments, the systems are bone graft distribution systems. In these embodiments, the central beam can further comprise a grafting port. Likewise the expanding frame can open bone graft distribution windows on the top, the bottom, the sides, or a combination thereof, upon expansion.

In some embodiments, the frame can be formed monolithically. In these embodiments, each plurality connector elements can be struts; wherein, the top struts are configured monolithically integral to the first top beam and the second top beam; and, the bottom struts are configured monolithically integral to the first bottom beam and the second bottom beam. The top struts and the bottom struts of the laterovertically-expanding frame can each be configured to open a graft distribution window upon expansion, expanding from the first top beam to the second top beam, the first top beam to the first bottom beam, the second top beam to the second bottom beam, or the first bottom beam to the second bottom beam. Likewise, in some embodiments, the top connector struts are configured monolithically integral to the first top beam and the second top beam; and, the bottom struts are configured monolithically integral to the first bottom beam and the second bottom beam; the first side struts are configured monolithically integral to the first top beam and the first bottom beam; and, the second side struts are configured monolithically integral to the second top beam and the second bottom beam. It should be appreciated that, in such embodiments, the top, bottom, first side, and second side of the laterovertically-expanding frame cam form a monolithically integral frame.

In fact, in some embodiments, the stabilizer can include a locking element that engages with the expansion member to lock the expansion member to the stabilizer when the expansion member is fully inserted into the frame. As such, an intervertebral scaffolding system can comprise a laterovertically-expanding frame configured to create an intervertebral scaffolding system in vivo, the frame having a collapsed state and an expanded state, the expanded state operably contacting the intervertebral space; a stabilizer that slideably engages with the distal region of the frame, and is configured for retaining the frame from lateral movement that exceeds the expanded state; and an expansion member configured for in vivo introduction into the frame when the frame is in a collapsed state and thereafter expanding the frame to an expanded state; wherein the stabilizer includes a locking element that engages with the expansion member to lock the expansion member to the stabilizer when the expansion member is fully inserted into the frame.

Moreover, the stabilizer can have an H-configuration having a first vertical leg, a second vertical leg, a cross-member that connects the first vertical leg at least substantially parallel to the second vertical leg, the cross-member having a vertical support member extending at least substantially parallel to the first vertical leg and second vertical leg, and the expansion member includes a vertical slot extending completely through a distal end thereof and dividing the distal end of the expansion member into a first portion and a second portion, the first portion being separated from the second portion by the vertical slot, the vertical slot configured complimentary to the vertical support member. In some embodiments, the first portion and second portion are laterally displaceable relative to one another. In some embodiments, the laterally displacing of the first portion and second portion relative to one another disengages the expansion member from the locking element.

Likewise, in some embodiments, an intervertebral scaffolding system can comprise a laterovertically-expanding frame configured to create an intervertebral scaffolding system in vivo, the frame having a collapsed state and an expanded state, the expanded state operably contacting the intervertebral space; a proximal portion having an end, a distal portion having an end, and a central frame axis of the expanded state; a first top beam including a proximal portion having an end and a distal portion having an end, the central axis of the first top beam at least substantially on (i) a top plane containing the central axis of the first top beam and a central axis of a second top beam and (ii) a first side plane containing the central axis of the first top beam and a central axis of a first bottom beam; the second top beam including a proximal portion having an end and a distal portion having an end, the central axis of the second top beam at least substantially on (i) the top plane and (ii) a second side plane containing the central axis of the second top beam and a central axis of a second bottom beam; the first bottom beam including a proximal portion having an end and a distal portion having an end, the central axis of the first bottom beam at least substantially on (i) a bottom plane containing the central axis of the first bottom beam and the central axis of the second top beam and (ii) the first side plane; the second bottom beam including a proximal portion having an end and a distal region having an end, the central axis of the second bottom beam being at least substantially on (i) the bottom plane and (ii) a second side plane containing the central axis of the second bottom beam and the central axis of the second top beam; a plurality of top connector elements configured to expandably connect the first top beam to the second top beam, the expanding consisting of a flexing at least substantially on the top plane; a plurality of bottom connector elements configured to expandably connect the first bottom beam to the second bottom beam, the expanding consisting of a flexing at least substantially on the bottom plane; a plurality of first side connector elements configured to expandably connect the first top beam to the first bottom beam, the expanding consisting of a flexing at least substantially on the first side plane; a plurality of second side connector elements configured to expandably connect the second top beam to the second bottom beam, the expanding consisting of a flexing at least substantially on the second side plane; an expansion member configured for in vivo introduction into the frame when the frame is in a collapsed state and thereafter expanding the frame to an expanded state; and a stabilizer that slidably engages with the distal region of the first top beam, the first bottom beam, the second top beam, the second bottom beam, or a combination thereof, and is configured for retaining the first top beam, the first bottom beam, the second top beam, the second bottom beam, or the combination thereof, from a lateral movement that exceeds the expanded state; wherein the stabilizer includes a locking element that engages with the expansion member to lock the expansion member to the stabilizer when the expansion member is fully inserted into the frame.

Furthermore, the stabilizer can have an H-configuration having a first vertical leg, a second vertical leg, and a cross-member that connects the first vertical leg at least substantially parallel to the second vertical leg, the first vertical leg including a retaining surface for engaging with the first top beam and the first bottom beam, the second vertical leg including a retaining surface for engaging with the second top beam and the second bottom beam, and the cross-member providing a tensile force for resisting the first top beam, the first bottom beam, the second top beam, and the second bottom beam from the lateral movement that exceeds the expanded state.

In some embodiments, the expansion member further includes a horizontal groove configured complementary to the cross-member of the stabilizer, and the horizontal groove of the expansion member slidably connects with the cross-member in the expanded state. In some embodiments, the cross-member further comprises a vertical support member, the expansion member having vertical slot extending completely through a distal end thereof and dividing the distal end of the expansion member into a first portion and a second portion, the first portion being separated from the second portion by the vertical slot, the vertical slot configured complimentary to the vertical support member, and the vertical slot of the expansion member slidably connects with the vertical support member in the expanded state. In some embodiments, the first portion and second portion of the expansion member are laterally displaceable relative to one another. In some embodiments, the laterally displacing of the first portion and second portion relative to one another disengages the expansion member from the locking element. In some embodiments, the stabilizer further comprises a point of attachment for releasably attaching a guidewire adapted for guiding the expansion member into the laterovertically expanding frame. And, in some embodiments, the cross-member includes a first pillar and a second pillar that operably connect at a hub that has a point of attachment for releasably attaching a guidewire for guiding the expansion member into the laterovertically expanding frame.

In some embodiments, the scaffolding system can further comprise a grafting port. In some embodiments, the scaffolding system can further include a top tensioner operably attaching the first top beam to the second top beam and a bottom tensioner operably attaching the first bottom beam to the second bottom beam, wherein each plurality connector elements are struts; and, wherein, the top struts are configured monolithically integral to the first top beam and the second top beam; the bottom struts are configured monolithically integral to the first bottom beam and the second bottom beam; the top tensioner is configured monolithically integral to the first top beam and the second top beam; and, the bottom tensioner is configured monolithically integral to the first bottom beam and the second bottom beam; wherein, the top struts and bottom struts of the laterovertically-expanding frame are each configured to open a graft distribution window upon expansion, expanding from the first top beam to the second top beam, the first top beam to the first bottom beam, the second top beam to the second bottom beam, or the first bottom beam to the second bottom beam.

Likewise, the scaffolding system can further include a top tensioner operably attaching the first top beam to the second top beam and a bottom tensioner operably attaching the first bottom beam to the second bottom beam, and wherein, the top connector struts are configured monolithically integral to the first top beam and the second top beam; and, the bottom struts are configured monolithically integral to the first bottom beam and the second bottom beam; the first side struts are configured monolithically integral to the first top beam and the first bottom beam; the second side struts are configured monolithically integral to the second top beam and the second bottom beam; the top tensioner is configured monolithically integral to the first top beam and the second top beam; and, the bottom tensioner is configured monolithically integral to the first bottom beam and the second bottom beam; wherein, the top, bottom, first side, and second side of the laterovertically-expanding frame form a monolithically integral frame.

The teachings are also directed to a method of fusing an intervertebral space. The methods can use the scaffolding systems taught herein. For example, the methods can include creating a point of entry into an intervertebral disc, the intervertebral disc having a nucleus pulposus surrounded by an annulus fibrosis; removing the nucleus pulposus from within the intervertebral disc through the point of entry, leaving the intervertebral space for expansion of a scaffolding system taught herein within the annulus fibrosis, the intervertebral space having a top vertebral plate and a bottom vertebral plate; inserting the laterovertically expanding frame in the collapsed state through the point of entry into the intervertebral space; inserting the central beam into the frame to form the scaffolding system; and, adding a grafting material to the intervertebral space.

The step of creating the point of entry can comprise creating a lateral dimension of the point of entry ranging from about 5 mm to about 15 mm, and the amount of lateral expansion can be selected to exceed the lateral dimension of the point of entry. The step of expanding can include expanding the laterovertically expanding frame laterally to a width that exceeds the width of the point of entry; and, inserting the central beam to expand the laterovertically expanding frame vertically to support the frame in the expanded state. The step of inserting the central beam into the laterovertically expanding frame includes engaging a means for preventing the central beam from backing out of the laterovertically-expanding frame after the expanding.

The teachings are also directed to a kit comprising a scaffolding system taught herein. The systems can include a cannula for inserting the scaffolding system into the intervertebral space; and, a guidewire adapted for guiding the central beam into the laterovertically expanding frame.

BRIEF DESCRIPTION OF THE FIGURES

FIGS. 8A-8D illustrate components of a graft distribution kit, according to some embodiments.

FIGS. 10A-10C illustrate profiles of an expanded graft distribution system to highlight the exit ports and bone graft windows, according to some embodiments.

FIGS. 30A-30E illustrate components of another insertion tool for use with a system having a cage with a stabilizer and central beam configured for expanding the cage, according to some embodiments.

DETAILED DESCRIPTION OF THE INVENTION

Figure 1A:
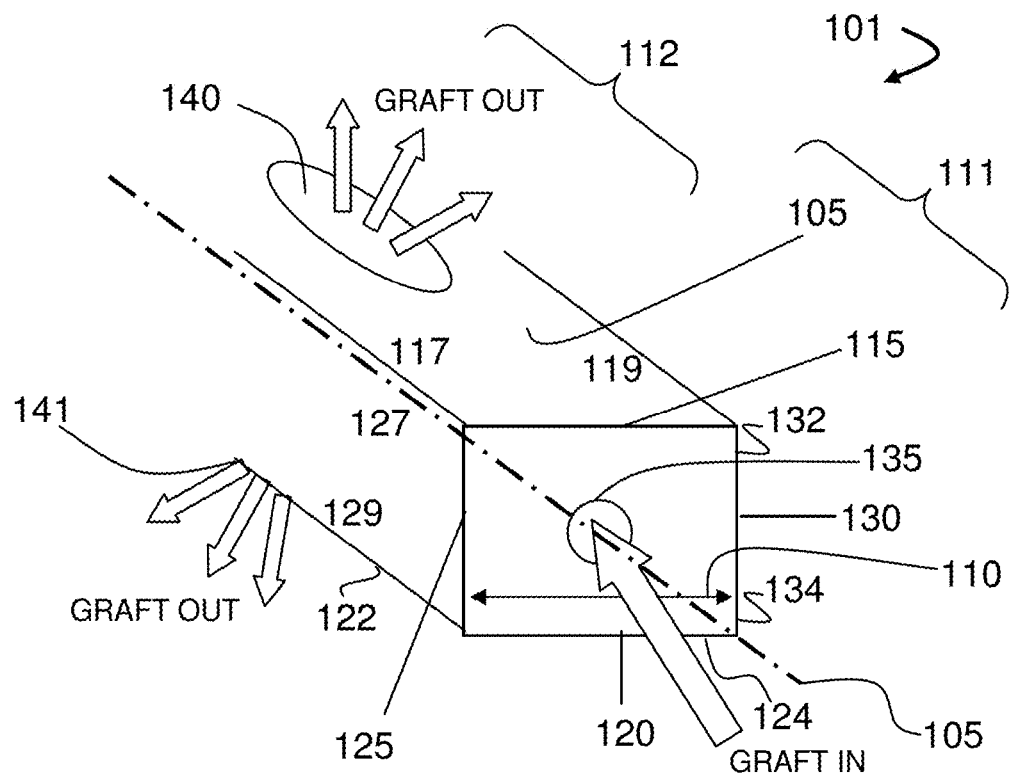
FIGS. 1A-1I illustrate components of the graft distribution system, according to some embodiments.

The teachings herein are directed to intervertebral scaffolding systems having a stabilizer for stabilizing and/or retaining support beams upon expansion of the scaffolding in an intervertebral disc space. The systems can have, for example, a central beam having a proximal portion having an end, a grafting portion having a top and a bottom, a distal portion having a end, a central beam axis, a graft distribution channel having an entry port at the end of the proximal portion, a top exit port at the top of the grafting portion, and a bottom exit port at the bottom of the grafting portion. These systems can also include a laterovertically-expanding frame having a lumen, a first top beam, a second top beam, a first bottom beam, and a second bottom beam, each having a proximal portion and a distal portion, and each operably connected to each other at their respective proximal portions and distal portions with connector elements to form the laterovertically-expanding frame that is operable for a reversible collapse from an expanded state into a collapsed state. The expanded state, for example, can be configured to have an open graft distribution window that at least substantially closes upon the reversible collapse. In these embodiments, the laterovertically-expanding frame is adapted for receiving an insertion of the central beam to form the graft distribution system.

In some embodiments, the systems can also include a laterovertically-expanding frame having a first top beam, a second top beam, a first bottom beam, and a second bottom beam; wherein, the beams are in an at least substantially parallel arrangement with each other, each having a proximal portion, a grafting portion, and a distal portion, and each operably connected to each other at their respective proximal portions and distal portions to form the laterovertically-expanding frame in a square, cylindrical shape that is operable for a reversible collapse from an expanded state into a collapsed state. The expanded state, for example, can be configured to have an open graft distribution window that at least substantially closes upon the reversible collapse. In these embodiments, the laterovertically-expanding frame is adapted for receiving an insertion of the central beam to form the graft distribution system.

The term "subject" and "patient" can be used interchangeably in some embodiments and refer to an animal such as a mammal including, but not limited to, non-primates such as, for example, a cow, pig, horse, cat, dog; and primates such as, for example, a monkey or a human. As such, the terms "subject" and "patient" can also be applied to non-human biologic applications including, but not limited to, veterinary, companion animals, commercial livestock, and the like. Moreover, terms of degree are used herein to provide relative relationships between the position and/or movements of components of the systems taught herein. For example, the phrase "at least substantially parallel" is used to refer to a position of one component relative to another. An axis that is at least substantially parallel to another axis refers to an orientation that is intended, for all practical purposes to be parallel, but it is understood that this is just a convenient reference and that there can be variations due to stresses internal to the system and imperfections in the devices and systems. Likewise, the phrase "at least substantially on a . . . plane" refers to an orientation or movement that is intended, for all practical purposes to be on or near the plane as a convenient measure of the orientation or movement, but it is understood that this is just a convenient reference and that there can be variations due to stresses internal to the system and imperfections in the devices and systems. Likewise, the phrase "at least substantially coincident" refers to an orientation or movement that is intended, for all practical purposes to be on or near, for example, an axis or a plane as a convenient measure of the orientation or movement, but it is understood that this is just a convenient reference and that there can be variations due to stresses internal to the system and imperfections in the devices and systems.

FIGS. 1A-1I illustrate components of the system, according to some embodiments. As shown in FIG. 1A, the graft distribution systems 100 can have a central beam 101 with a central beam axis 105, a graft distribution channel with an entry port 135 in fluid communication with a top exit port 140, and a bottom exit port 141. The central beam 101 can also have a proximal portion 111 having and end with the entry port 135, a grafting portion 112 having the top exit port 140 and the bottom exit port 141, and a distal portion (not shown). The central beam 101 can also be sized to have a transverse cross-section 110 having a maximum dimension ranging from 5 mm to 15 mm for placing the central beam 101 into an intervertebral space through an annular opening having a maximum lateral dimension ranging from 5 mm to 15 mm, the intervertebral space having a top vertebral plate and a bottom vertebral plate. The central beam 101 can also have a top surface 115 with a first top-lateral surface 117 and a second top-lateral surface 119, a bottom surface 120 with a first bottom-lateral surface 122 and a second bottom-lateral surface 124, a first side surface 125 with a first top-side surface 127 and a first bottom-side surface 129, and a second side surface 130 with a second top-side surface 132 and a second bottom-side surface 134.

In some embodiments, the central beam can have transverse cross-sectional lateral dimension ranging from about 5 mm to about 15 mm. In some embodiments, the vertical dimension of the central beam can range from about 4 mm to about 12 mm, about 5 mm to about 11 mm, about 6 mm to about 10 mm, and about 7 mm to about 9 mm, about 6 mm to about 8 mm, about 6 mm to about 8 mm, about 6 mm, or any range or amount therein in increments of 1 mm. In some embodiments, the lateral dimension of the central beam can range from about 5 mm to about 15 mm, about 6 mm to about 14 mm, about 7 mm to about 13 mm, about 8 mm to about 12 mm, about 10 mm, or any range or amount therein in increments of 1 mm. In some embodiments, transverse cross-section of the central beam has an area with an effective diameter ranging from about 2 mm to about 20 mm, from about 3 mm to about 18 mm, from about 4 mm to about 16 mm, from about 5 mm to about 14 mm, from about 6 mm to about 12 mm, from about 7 mm to about 10 mm, or any range therein. In some embodiments, the low profile has an area with a diameter of 2 mm, 4 mm, 6 mm, 8 mm, 10 mm, 12 mm, 14 mm, 16 mm, 18 mm, or any range therein, including any increment of 1 mm in any such diameter or range therein. In some embodiments, the width (mm)×height (mm) of the central beam can be 9.0×5.0, 9.0×6.0, 9.0×7.0, 9.0×8.0, 9.0×9.0, and 9.0×10.0, or any deviation in dimension therein in increments of +/−0.1 mm. And, in some embodiments, the central beam can have a transverse cross-sectional lateral or vertical dimension that ranges from 6.5 mm to 14.0 mm.

Figure 1B:
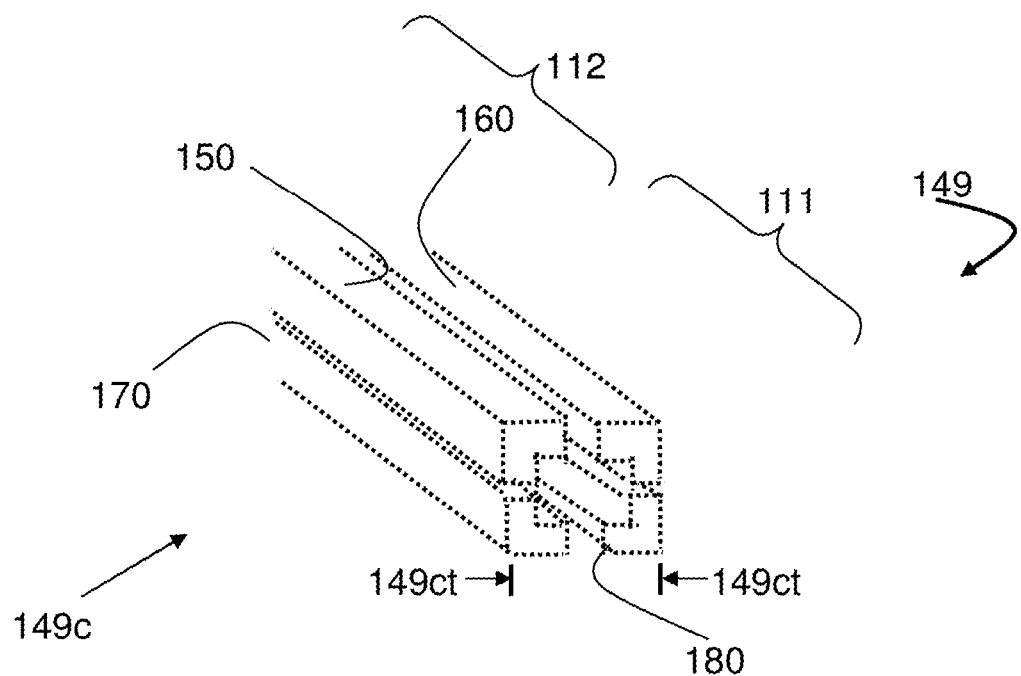
Figure 1C:
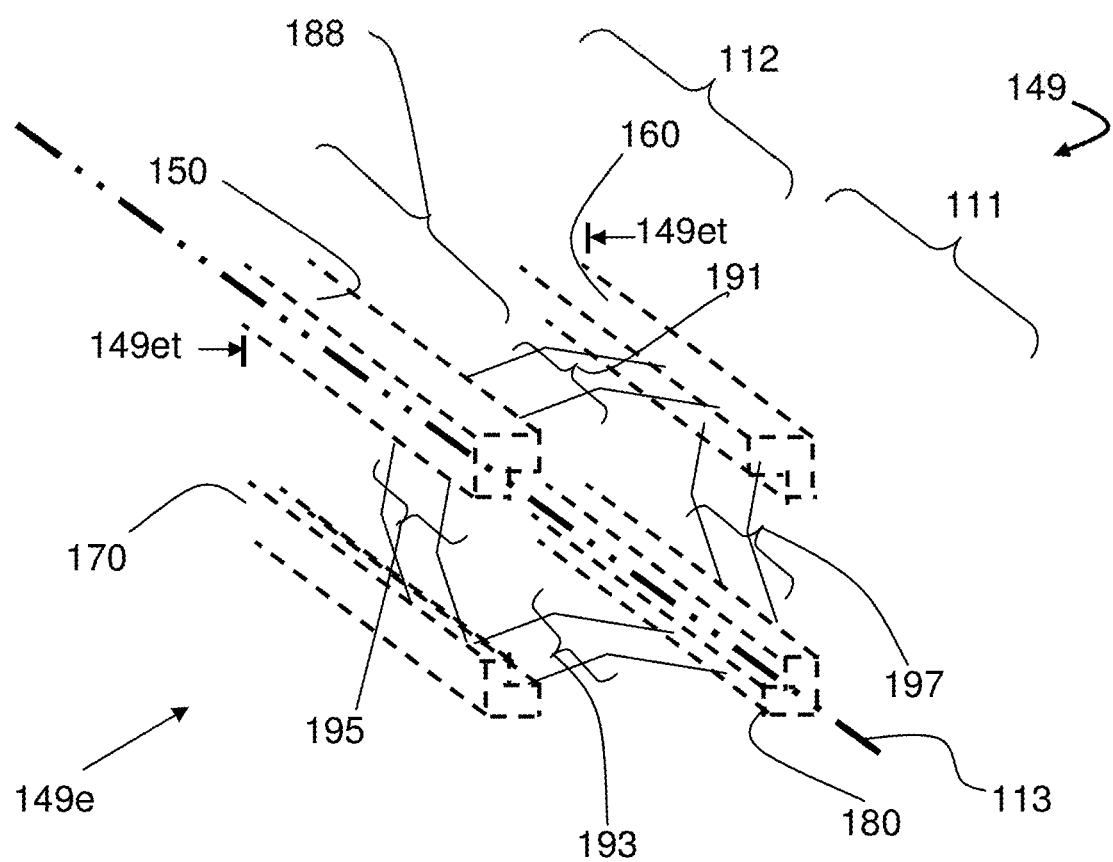

As shown in FIGS. 1B and 10, the system 100 can also comprise a laterovertically-expanding frame 149 configured for operably contacting the central beam 101 to create a graft distribution system 100 in vivo, the frame 149 having a collapsed state 149c with a transverse cross section 149ct having a maximum dimension ranging from 5 mm to 15 mm for placing the frame 149 in the intervertebral space through the annular opening for expansion. Likewise, the frame 149 can also have an expanded state 149e with a transverse cross section 149et having a maximum dimension ranging from 6.5 mm to 18 mm for retaining the frame 149 in the intervertebral space, the expanded state operably contacting with the central beam 101 in the intervertebral space. The frame 149 can be defined as including a proximal portion 111 having an end, a grafting portion 112, a distal portion (not shown) having an end, and a central frame axis 113 of the expanded state 149e.

In some embodiments, the frame can have transverse cross-sectional lateral dimension in the collapsed state ranging from about 5 mm to about 15 mm. In some embodiments, the vertical dimension of the frame in the collapsed state can range from about 4 mm to about 12 mm, about 5 mm to about 11 mm, about 6 mm to about 10 mm, and about 7 mm to about 9 mm, about 6 mm to about 8 mm, about 6 mm, or any range or amount therein in increments of 1 mm. In some embodiments, the lateral dimension of the frame in the collapsed state can range from about 5 mm to about 15 mm, about 6 mm to about 14 mm, about 7 mm to about 13 mm, about 8 mm to about 12 mm, about 10 mm, or any range or amount therein in increments of 1 mm. In some embodiments, transverse cross-section of the frame in the collapsed state has an area with an effective diameter ranging from about 2 mm to about 20 mm, from about 3 mm to about 18 mm, from about 4 mm to about 16 mm, from about 5 mm to about 14 mm, from about 6 mm to about 12 mm, from about 7 mm to about 10 mm, or any range therein. In some embodiments, the low profile has an area with a diameter of 2 mm, 4 mm, 6 mm, 8 mm, 10 mm, 12 mm, 14 mm, 16 mm, 18 mm, or any range therein, including any increment of 1 mm in any such diameter or range therein. In some embodiments, the width (mm)×height (mm) of the frame in the collapsed state can be 9.0×5.0, 9.0×6.0, 9.0×7.0, 9.0×8.0, 9.0×9.0, and 9.0×10.0, or any deviation in dimension therein in increments of +/−0.1 mm. In some embodiments, the frame can have a transverse cross-sectional dimension, lateral or vertical in the expanded state ranging from 4.0 mm to 18 mm, from 5.0 mm to 19.0 mm, from 6.0 mm to 17.5 mm, from 7.0 mm to 17.0 mm, from 8.0 mm to 16.5 mm, from 9.0 mm to 16.0 mm, from 9.0 mm to 15.5 mm, from 6.5 mm to 15.5 mm, or any range or amount therein in increments of +/−0.1 mm.

The term "collapsed state" can be used to refer to a configuration of the frame in which the transverse cross-sectional area, or profile, is at least substantially at it's minimum, and the term "expanded state" can be used to refer to a configuration of the frame that is expanded at least substantially beyond the collapsed state. In this context, a frame is expanded at least "substantially" beyond the collapsed state when a bone graft window of the frame has opened from the closed configuration by at least a 20% increase area of the bone graft window from the collapsed state. In some embodiments, the frame is expanded at least "substantially" beyond the collapsed state when a bone graft window of the frame has opened by at least a 15%, 20%, 25%, 30%, 35%, 40%, 45%, 50%, 60%, 70%, 80%, 90%, 100%, 150%, 200%, 250%, 300%, or more when compared to the bone graft window from the collapsed state. In some embodiments, the frame is expanded at least "substantially" beyond the collapsed state when a bone graft window of the frame has opened by at least 2×, 3×, 5×, 10×, 15×, 20×, or more when compared to the bone graft window from the collapsed state.

In some embodiments, the laterovertically expandable frames are created in an expanded state. And the expanded state can include a state that is at least 30%, at least 40%, at least 50%, at least 60%, at least 70%, at least 80%, at least 90%, or at least 95% of the full expansion. The term "full expansion" can be used to refer to an extent of expansion upon which a connector element begins to fatigue, fail, or crack; or, in some embodiments, strain beyond 10%, 20%, or 30%.

The frame 149 can be configured to have a first top beam 150 including a proximal portion 111 having an end, a grafting portion 112, and a distal portion (not shown) having an end, the first top beam 150 configured for contacting the first top-lateral surface 117 of the central beam and the first top-side surface 127 of the central beam 101 in the expanded state 149e, the central axis of the first top beam at least substantially on (i) a top plane containing the central axis of the first top beam and the central axis of a second top beam and (ii) a first side plane containing the central axis of the first top beam and the central axis of a first bottom beam. Likewise the frame 149 can be configured to have a second top beam 160 including a proximal portion 111 having an end, a grafting portion 112 having an end, and a distal portion (not shown) having an end, the second top beam 160 configured for contacting the second top-lateral surface 119 of the central beam 101 and the second top-side surface 132 of the central beam 101 in the expanded state 149e, the central axis of the second top beam at least substantially on (i) the top plane and (ii) a second side plane containing the central axis of the second top beam and the central axis of a second bottom beam. Likewise the frame 149 can be configured to have a first bottom beam 170 including a proximal portion 111 having an end, a grafting portion 112, and a distal portion (not shown) having an end, the first bottom beam 170 configured for contacting the first bottom-lateral surface 122 of the central beam 101 and the first bottom-side surface 129 of the central beam 101 in the expanded state 149e, the central axis of the first bottom beam at least substantially on (i) a bottom plane containing the central axis of the first bottom beam and the central axis of a second top beam and (ii) the first side plane. Likewise the frame 149 can be configured to have a second bottom beam 180 including a proximal portion 111 having an end, a grafting portion 112 having an end, and a distal region (not shown) having an end, the second bottom beam 160 configured for contacting the second bottom-lateral surface 124 of the central beam 101 and the second bottom-side surface 134 of the central beam 101 in the expanded state 149e, the central axis of the second bottom beam being at least substantially on (i) the bottom plane and (ii) a second side plane containing the central axis of the second bottom beam and the second top beam.

In some embodiments, the central axis of the first top beam 150 can be at least substantially parallel to the central beam axis 105. Likewise the frame 149 can be configured to have a second top beam 160 including a proximal portion 111 having an end, a grafting portion 112 having an end, and a distal portion (not shown) having an end, the second top beam 160 configured for contacting the second top-lateral surface 119 of the central beam 101 and the second top-side surface 132 of the central beam 101 in the expanded state 149e, the central axis of the second top beam 160 being at least substantially parallel to the central beam axis 105. Likewise the frame 149 can be configured to have a first bottom beam 170 including a proximal portion 111 having an end, a grafting portion 112, and a distal portion (not shown) having an end, the first bottom beam 170 configured for contacting the first bottom-lateral surface 122 of the central beam 101 and the first bottom-side surface 129 of the central beam 101 in the expanded state 149e, the central axis of the first bottom beam 170 being at least substantially parallel to the central beam axis 105. Likewise the frame 149 can be configured to have a second bottom beam 180 including a proximal portion 111 having an end, a grafting portion 112 having an end, and a distal region (not shown) having an end, the second bottom beam 160 configured for contacting the second bottom-lateral surface 124 of the central beam 101 and the second bottom-side surface 134 of the central beam 101 in the expanded state 149e, the central axis of the second bottom beam 180 being at least substantially parallel to the central beam axis 105.

Figure 1D:
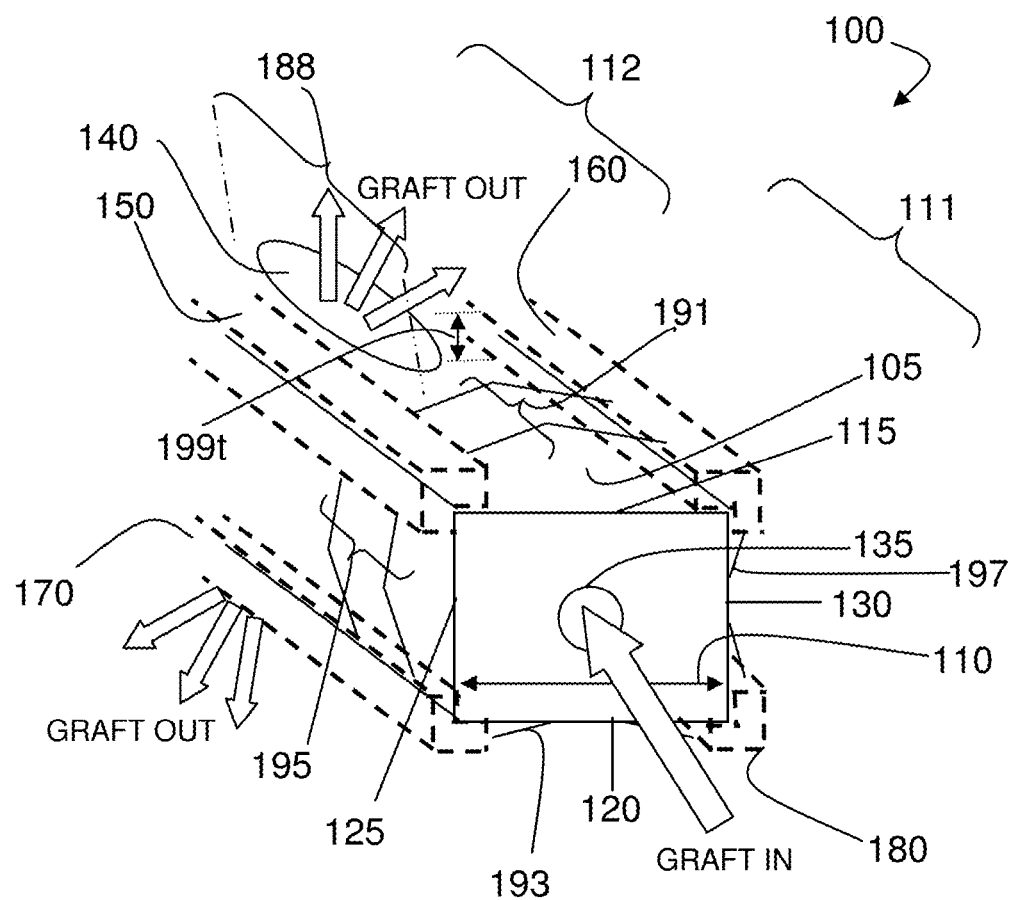

As shown in FIG. 1D, the systems provided herein have the layered effect from the frame on the central beam that provides an additive dimension, both laterally and vertically. The added dimension allows for a low profile entry of the system into the intervertebral disc space, a wide lateral profile after expansion in vivo to avoid backout, as well as a sleeve for safe insertion of the central beam between the top endplate and bottom endplate in the intervertebral space. In some embodiments, the first top beam, second top beam, first bottom beam, and second bottom beam can each have a transverse cross-sectional wall thickness adding to the respective central beam dimension, the thickness ranging from about 0.5 mm to about 5.0 mm, from about 0.75 mm to about 4.75 mm, from about 1.0 mm to about 4.5 mm, from about 1.25 mm to about 4.25 mm, from about 1.5 mm to about 4.0 mm, from about 1.75 mm to about 3.75 mm, from about 2.0 mm to about 3.5 mm, from about 2.25 mm to about 3.25 mm, or any range therein in increments of 0.05 mm. In some embodiments, the first top beam, second top beam, first bottom beam, and second bottom beam can each have a transverse cross-sectional wall thickness adding to the respective central beam dimension, the thickness ranging from about 1.5 mm to about 2.5 mm, including 1.5, 1.75, 2.0, 2.25, 2.5, or an amount therein in increments of 0.05 mm.

The beams of the laterovertically-expanding frame 149 can be operably connected through connector elements. As such, the frame 149 can include a plurality of proximal top connector elements 191 configured to expandably connect the proximal portion 111 of the first top beam 150 to the proximal portion 111 of the second top beam 160, the expanding consisting of a flexing at least substantially on a top plane containing the central axis of the first top beam 150 and the central axis of the second top beam 160. Likewise the frame 149 can be configured to have a plurality of distal top connector elements (not shown) configured to expandably connect the distal portion of the first top beam 150 to the distal portion of the second top beam 160, the expanding consisting of a flexing at least substantially on the top plane.

Likewise the frame 149 can be configured to have a plurality of proximal bottom connector elements 193 configured to expandably connect the proximal portion 111 of the first bottom beam 170 to the proximal portion 111 of the second bottom beam 180, the expanding consisting of a flexing at least substantially on a bottom plane containing the central axis of the first bottom beam 170 and the central axis of the second bottom beam 180. Likewise the frame 149 can be configured to have a plurality of distal bottom connector elements (not shown) configured to expandably connect the distal portion of the first bottom beam 170 to the distal portion of the second bottom beam 180, the expanding consisting of a flexing at least substantially on the bottom plane.

Likewise the frame 149 can be configured to have a plurality of proximal first side connector elements 195 configured to expandably connect the proximal portion 111 of the first top beam 150 to the proximal portion 111 of the first bottom beam 170, the expanding consisting of a flexing at least substantially on a first side plane containing the central axis of the first top beam 150 and the central axis of the first bottom beam 170; a plurality of distal first side connector elements (not shown) configured to expandably connect the distal portion of the first top beam 150 to the distal portion of the first bottom beam 170, the expanding consisting of a flexing at least substantially on the first side plane. Likewise the frame 149 can be configured to have a plurality of proximal second side connector elements 197 configured to expandably connect the proximal portion 111 of the second top beam 160 to the proximal portion 111 of the second bottom beam 170, the expanding consisting of a flexing at least substantially on a second side plane containing the central axis of the second top beam 160 and the central axis of the second bottom beam 180; a plurality of distal second side connector elements (not shown) configured to expandably connect the distal portion of the second top beam 160 to the distal portion of the second bottom beam 180, the expanding consisting of a flexing at least substantially on the second side plane.

In some embodiments, each plurality of proximal connector elements can be configured as proximal struts in an at least substantially parallel alignment in the expanded state and the collapsed state; and, each plurality distal connector elements are distal struts can be configured in an at least substantially parallel alignment in the expanded state and the collapsed state. As such, the proximal top struts can be configured monolithically integral to the first top beam and the second top beam and adapted to flex toward the distal top struts during collapse; and, the distal top struts can be configured monolithically integral to the first top beam and the second top beam and adapted to flex toward the proximal top struts during collapse. Likewise, the proximal bottom struts can be configured monolithically integral to the first bottom beam and the second bottom beam and adapted to flex toward the distal bottom struts during collapse; and, the distal bottom struts can be configured monolithically integral to the first bottom beam and the second bottom beam and adapted to flex toward the proximal bottom struts during collapse. Likewise, the proximal first side struts can be configured monolithically integral to the first top beam and the first bottom beam and adapted to flex toward the distal first side struts during collapse; and, the distal first side struts can be configured monolithically integral to the first top beam and the first bottom beam and adapted to flex toward the proximal first side struts during collapse. Likewise, the proximal second side struts can be configured monolithically integral to the second top beam and the second bottom beam and adapted to flex toward the distal second side struts during collapse; and, the distal second side struts can be configured monolithically integral to the second top beam and the second bottom beam and adapted to flex toward the proximal second side struts during collapse.

As shown in FIG. 1D, the frame 149 can be configured for slidably engaging with the central beam 101 in vivo following placement of the central beam 101 in the intervertebral space through the annular opening, the slidably engaging including translating the central beam 101 into the frame 149 from the proximal end 11 of the frame 149 toward the distal end of the frame 149 in vivo; the translating including keeping the central beam axis 105 at least substantially coincident with the central frame axis 113 during the translating to create the graft distribution system 100 in vivo through the annular opening. The system 100 can also be configured to form a top graft-slab depth 199$t$ between the top surface 115 of the central beam 101 and the top vertebral endplate; and, a bottom graft-slab depth 199$b$ (not shown) between the bottom surface 120 of the central beam 101 and the bottom vertebral endplate in vivo. And, in some embodiments, the transverse cross-section 110 of the system 100 in vivo is greater than the maximum lateral dimension of the annular opening to avoid backout.

Figure 1E:
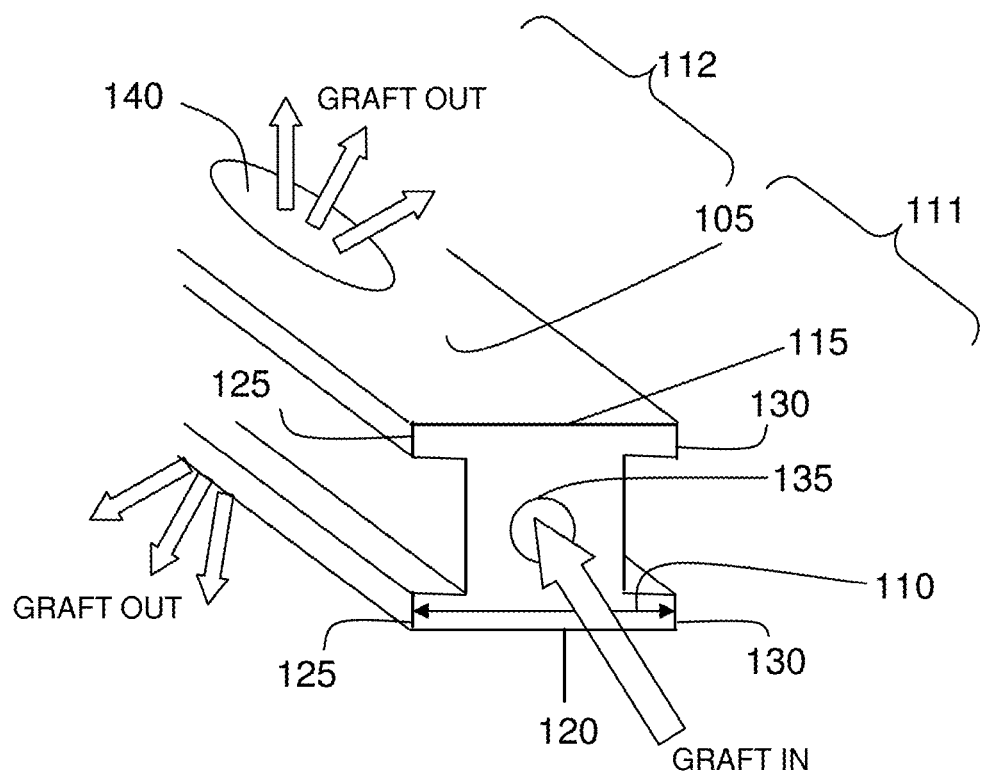
Figure 1F:
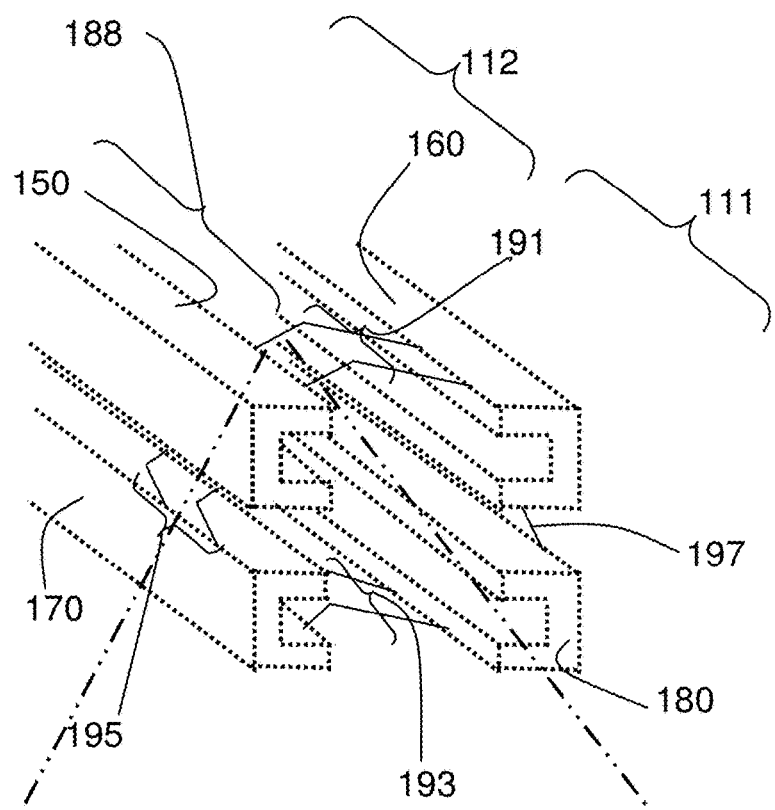

One of skill will appreciate that the central beam can have any configuration that would be operable with the teachings provided herein. In some embodiments, criteria for a suitable central beam may include a combination of a material and configuration that provides a suitable stiffness. In some embodiments, the central beam can comprise an I-beam. An example of an I-beam configuration and a complementary laterovertically expandable cage are shown in FIGS. 1E and 1F.

One of skill will further appreciate that the central beam can have any one or any combination of graft port configurations that would be operable with the teachings provided herein. In some embodiments, criteria for a suitable graft port configuration may include a combination of port size, number of ports, and placement of ports. In some embodiments, the central beam can comprise a side graft port.

Figure 1G:
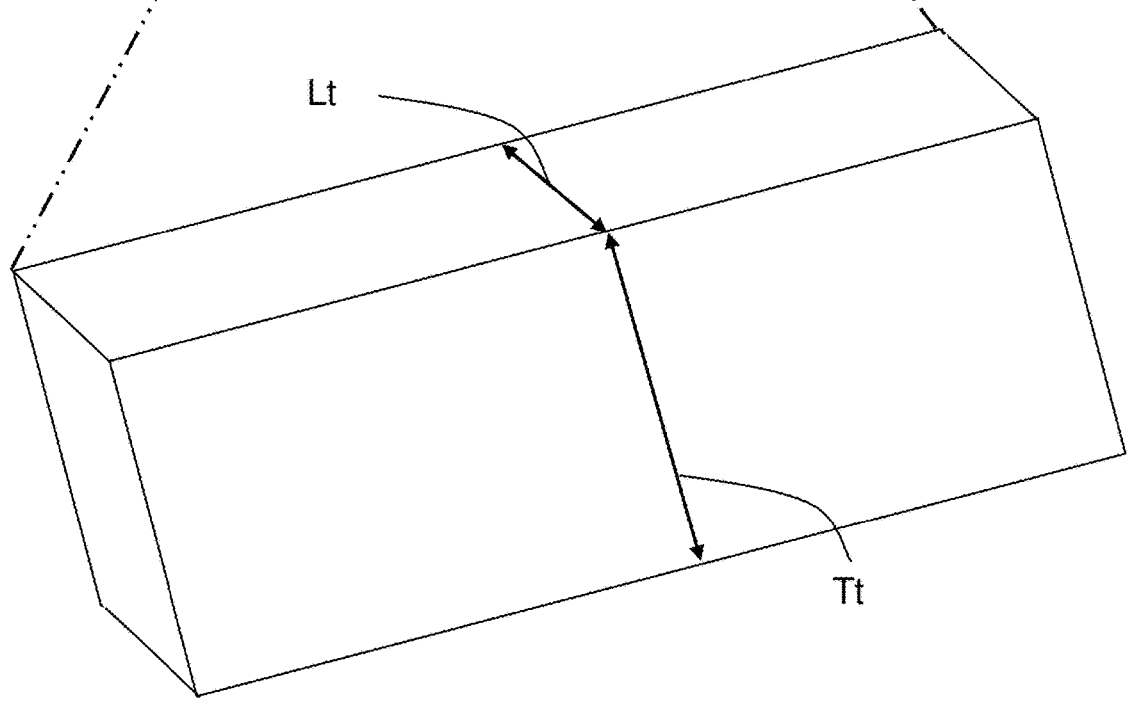
Figure 1H:
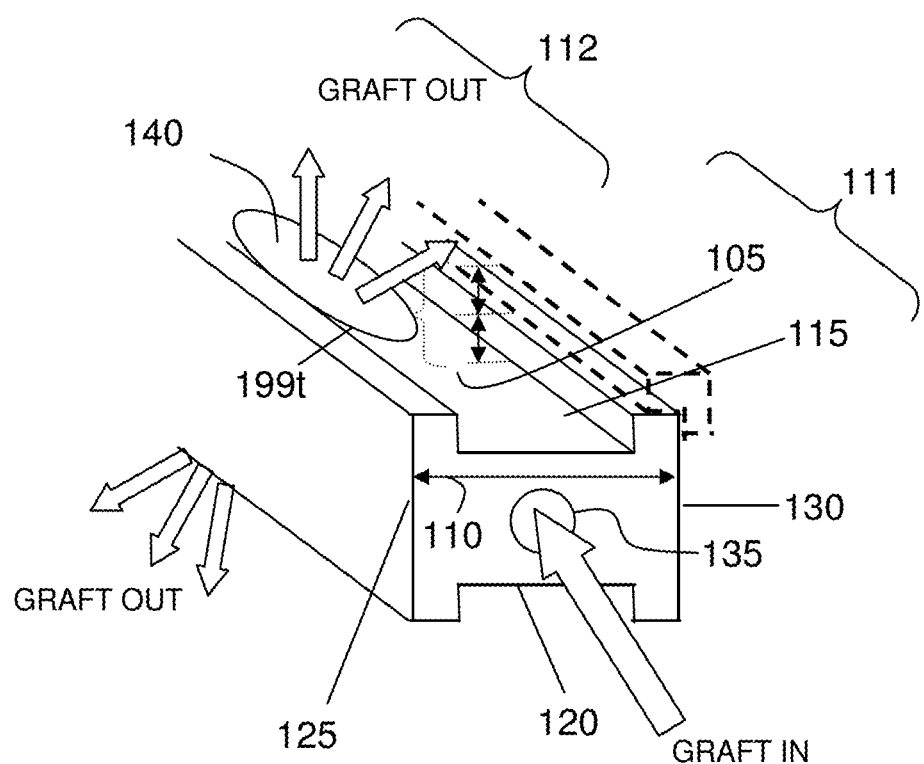
Figure 1I:
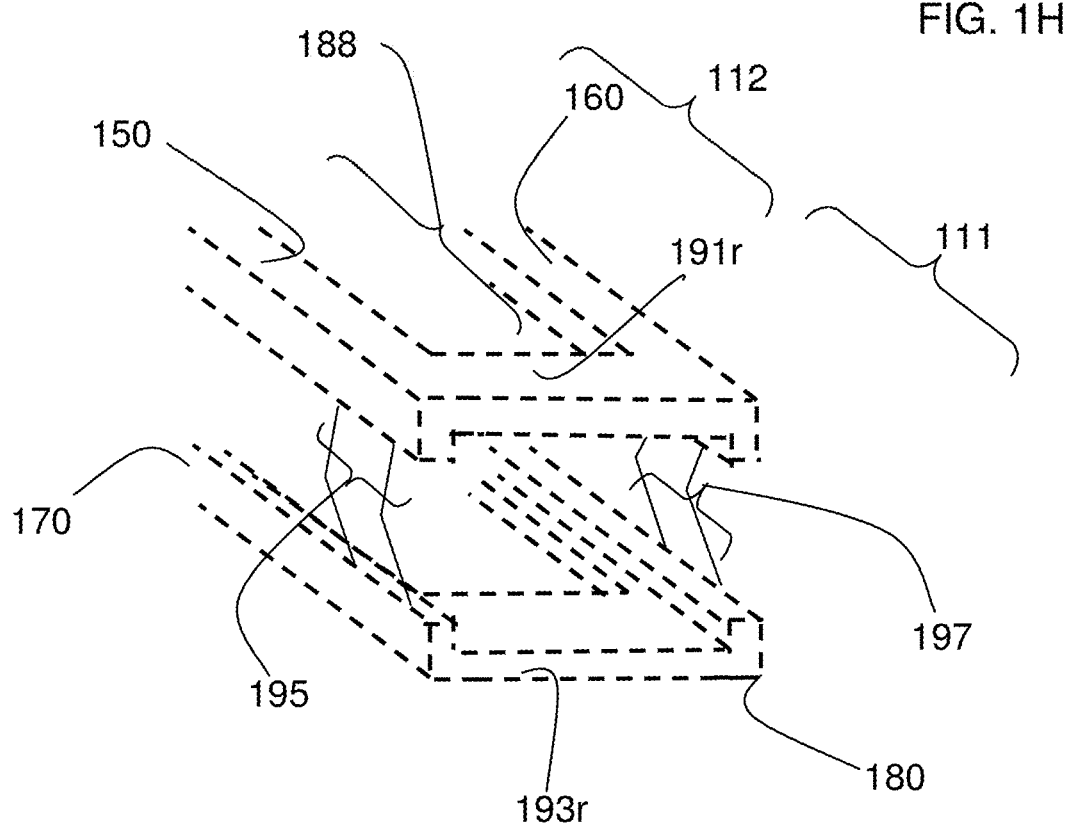

One of skill will further appreciate that the connector elements can vary in design but should meet the constraints as taught herein. In some embodiments, for example each of the connector elements 191,193,195,197 can have a cross-sectional aspect ratio of longitudinal thickness to transverse thickness ranging from 1:2 to 1:8. A section of a connector element is shown in FIG. 1G.

As such, the systems can also include an improved, low-profile, intervertebral disc cage that expands bidirectionally. Consistent with the teachings herein, the cages offer several improvements to the art that include, for example, preventing the cage from backing out of the annulus fibrosis after expansion in an intervertebral disc space. As such, the terms "cage," "scaffold" and "scaffolding", for example, can be used interchangeably with "laterovertically expandable frame", "expandable frame", or "frame", in some embodiments. The cages have the ability to at least (i) laterally expand within the intervertebral space to avoid backout of the device through the annulotomy, (ii) vertically expand for distraction of the intervertebral space, (iii) provide additional space within the device in the annulus for the introduction of graft materials; (iv) maintain a large, footprint to distribute load over a larger area against the endplate, for example, by not contracting in length to expand in height and/or width; and, (v) insert into the annulus in a minimally-invasive manner using only a unilateral approach.

Figure 2A:
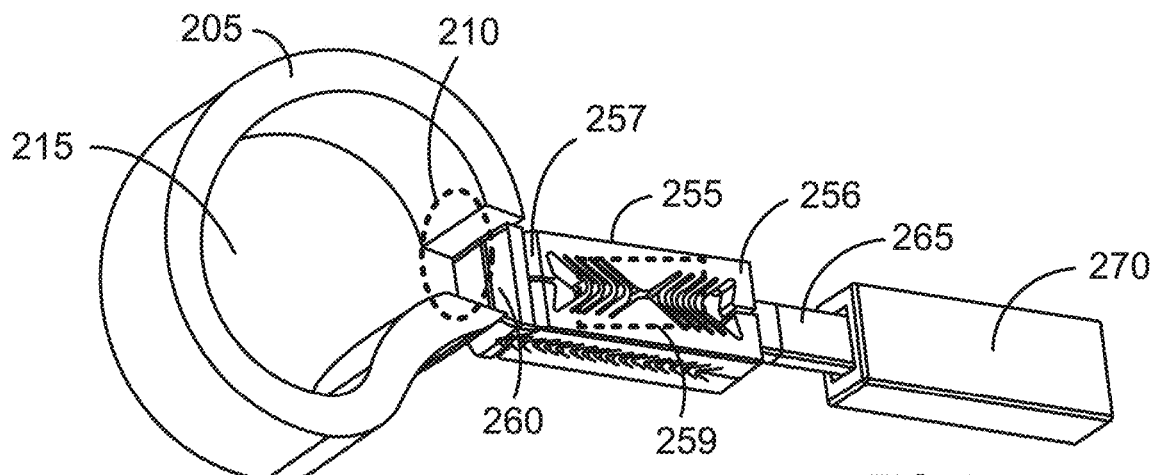
FIGS. 2A-2F illustrate a method of using a bidirectionally-expandable cage, according to some embodiments.
Figure 2B:
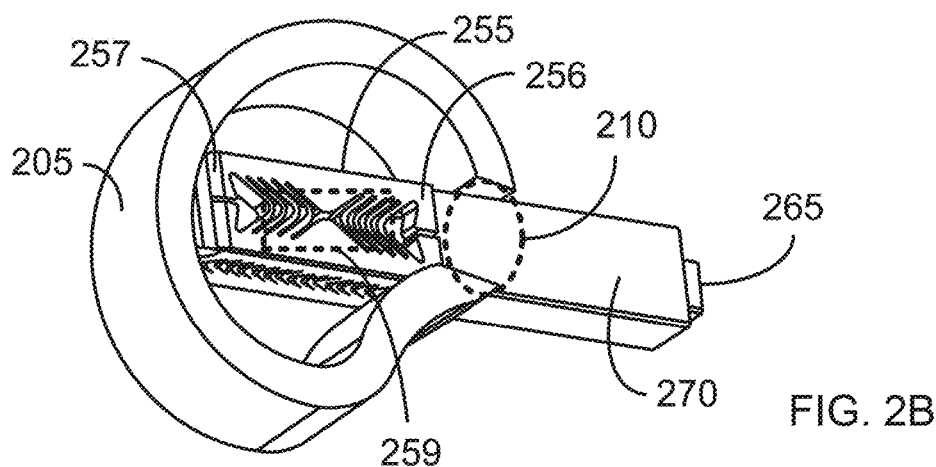

FIGS. 2A-2F illustrate a method of using a bidirectionally-expandable cage, according to some embodiments. As shown in FIGS. 2A-2B, an annulus 205 is prepared with an annulotomy serving as a single point of entry 210 and an intervertebral space 215 for insertion of a bidirectionally expandable cage system 250. As shown in FIGS. 2C-2F, the system 250 has a cage 255 having a proximal end 256, a distal end 257, and a lumen 258 that communicates with the intervertebral space 215 through an expandable/collapsible bone graft window 259; a shim core 260 having a tapered nose 262 at the distal end of the shim core 260; a releasably attachable rail beam 265; a pusher 270 that slidably translates over the shim core 260 and the rail beam 265; a trial shim 275 having a shoulder 277 and slidably translating over the rail beam 265 and shim core 260 into the lumen 258 of the cage 255, and a permanent shim 280 having a shoulder 282 and slidably translating over the rail beam 265 and shim core 260 into the lumen 258 of the cage 255.

Figure 2C:
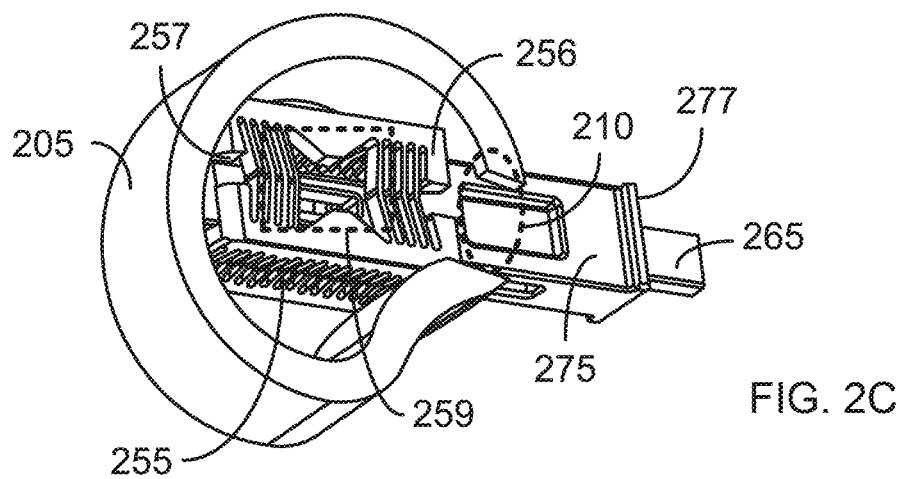
Figure 2D:
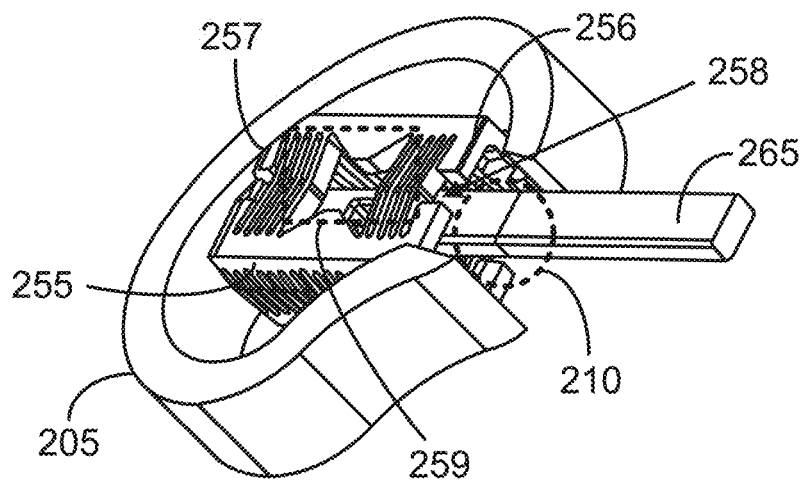
Figure 2E:
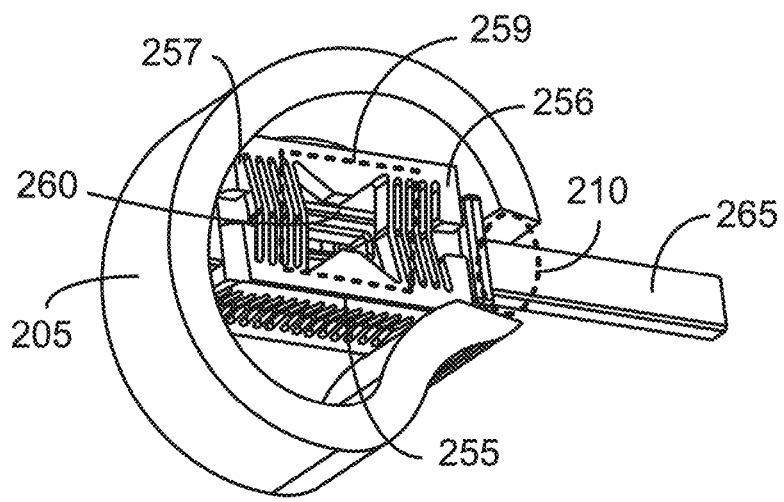
Figure 2F:
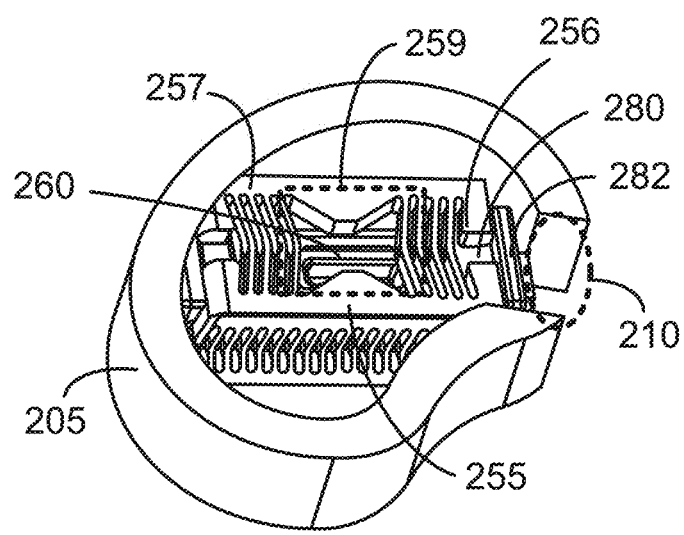

The procedure for implanting the cage 255 begins in FIG. 2A, including inserting a cannula (not shown) with a bullet-nosed obturator through the single point of entry 210 and inside the intervertebral disc space 215 until contacting the opposing wall of the annulus 205. The cannula (not shown) depth is used to select the desired length of the cage 255. The shim core 260 is loaded with bone graft material and the rail beam 265 is releasably attached to the shim core 260. The cage 255 is loaded onto the rail beam 265 and pushed onto the shim core 260 and into the cannula (not shown) using the pusher 270 until the distal end 257 of the cage 255 contacts the back of the tapered nose 262 of the shim core 260 as shown in FIG. 2A. The assembly of the shim core 260 and the cage 255 are inserted into the intervertebral space 215, and the cannula (not shown) is removed as shown in FIG. 2B. The lumen 258 of the cage 255 is loaded with bone graft material, and the trial shim 275 is slidably translated over the rail beam 265 and the shim core 260 into the lumen 258 of the cage 255 as shown in FIG. 2C. A variety of sizes of the trial shim 275 can be tested until the largest trial shim 275 that will fit is found, or until the trial shim having the desired vertical and lateral dimensions for expansion is used, in order to laterovertically expand the cage 255 as desired. The trial shim 275 is then removed, and the lumen 258 of the cage 255 is again filled with bone graft material with the shim core 260 remaining in place as shown in FIG. 2D. The permanent shim 280 is then slidably translated along the rail beam 265 and the shim core 260 into the intervertebral space 215 using the pusher 270 until the distal end 257 of the cage 255 contacts the back of the tapered nose 262 of the shim core 260 to maintain the desired laterovertical expansion of the cage 255 as shown in FIG. 2E. The rail beam 265 is then disconnected from the shim core 260 as shown in FIG. 2F.

It should be appreciated that the annulotomy can have nearly any dimension considered desirable to one of skill in the art. The annulotomy can have a vertical dimension, for example, that is the distance between a top vertebral plate and a bottom vertebral plate, the top vertebral plate and the bottom vertebral plate defining the upper and lower borders of the intervertebral disc space. In some embodiments, the vertical dimension can range from about 4 mm to about 12 mm, about 5 mm to about 11 mm, about 6 mm to about 10 mm, and about 7 mm to about 9 mm, about 6 mm to about 8 mm, about 6 mm, or any range or amount therein in increments of 1 mm. In some embodiments, the lateral dimension of the single point of entry can range from about 5 mm to about 15 mm, about 6 mm to about 14 mm, about 7 mm to about 13 mm, about 8 mm to about 12 mm, about 10 mm, or any range or amount therein in increments of 1 mm. In some embodiments, the single point of entry has an area with a diameter ranging from about 2 mm to about 20 mm, from about 3 mm to about 18 mm, from about 4 mm to about 16 mm, from about 5 mm to about 14 mm, from about 6 mm to about 12 mm, from about 7 mm to about 10 mm, or any range therein. In some embodiments, the low profile has an area with a diameter of 2 mm, 4 mm, 6 mm, 8 mm, 10 mm, 12 mm, 14 mm, 16 mm, 18 mm, or any range therein, including any increment of 1 mm in any such diameter or range therein. The low profile dimensions of the cages taught herein are designed to fit within these dimensions.

One of skill will also appreciate that there are several methods and devices that could be used to expand the cage. In some embodiments, the expanding includes using a means for (i) laterovertically expanding the cage and (ii) creating a convex surface that at least substantially complements the concavity of a surface of a vertebral endplate that contacts the pair of top beams or the pair of bottom beams.

One of skill will also appreciate a method that distracts the intervertebral space and laterally expands the cage to avoid back-out. As such, in some embodiments, the expanding includes introducing a laterovertical expansion member into the intervertebral space through the single point of entry and into the cage, the laterovertical expansion member configured to provide a vertical force through the cage and into the top vertical endplate and bottom vertical endplate to distract the intervertebral space; and, a lateral force on the first side wall and the second side wall to expand the cage to a width that is greater than the lateral dimension of the single point of entry to prevent the bidirectionally-expandable cage from backing out of the annulus fibrosis after the expanding.

One of skill will also appreciate having a method for passing bone grafting material into the intervertebral space. As such, the laterovertical expansion member can include a port for introducing the grafting material into the intervertebral space. The methods and systems provided herein include the use of bone graft materials known to one of skill. Materials which may be placed or injected into the intervertebral space include solid or semi-solid grafting materials, bone from removed from patient's facet, an iliac crest harvest from the patient, and bone graft extenders such as hydroxyapatite, demineralized bone matrix, and bone morphogenic protein. Examples of solid or semi-solid grafting material components include solid fibrous collagen or other suitable hard hydrophilic biocompatible material. Some materials may also include swelling for further vertical expansion of the intervertebral disc space.

One of skill will also appreciate having a method for retaining the laterovertical expansion member in the cage. As such, the introducing can include engaging a ratchet mechanism comprising a protuberance on the laterovertical expansion member that engages with a strut of the cage to prevent the cage from backing out of the annulus fibrosis after the expanding. The ratchet mechanism can be, for example, similar to a zip-tie ratchet mechanism having a gear component and a pawl component. In some embodiments, the cage has the gear component, for example, including the struts; and, the laterovertical expansion member is a shim device having the pawl component, for example, a projection that can angle toward the proximal end of the expansion member or away from the direction of insertion of the shim device. In some embodiments, the cage has the pawl component, for example, including the struts; and, the laterovertical expansion member is a shim device having the gear component, for example, a series of projections. In some embodiments, a projection can angle from about 5° to about 75° toward the proximal end of the expansion member or away from the direction of insertion of the shim device.

One of skill will also appreciate having a method of designing the shape of the cage upon expansion. As such, in some embodiments, the expanding includes selecting a shim configured to create a convex surface on the top surface of the top wall to at least substantially complement the concavity of the respective top vertebral plate, and/or the bottom surface of the bottom wall to at least substantially complement the concavity of the respective bottom vertebral plate. In some embodiments, the expanding includes selecting a shim configured to vertically expand the distal end of the cage more than the proximal end of the cage. And, in some embodiments, the expanding includes selecting a shim configured to laterally expand the distal end of the cage more than the proximal end of the cage.

Figures 3A, 3B:
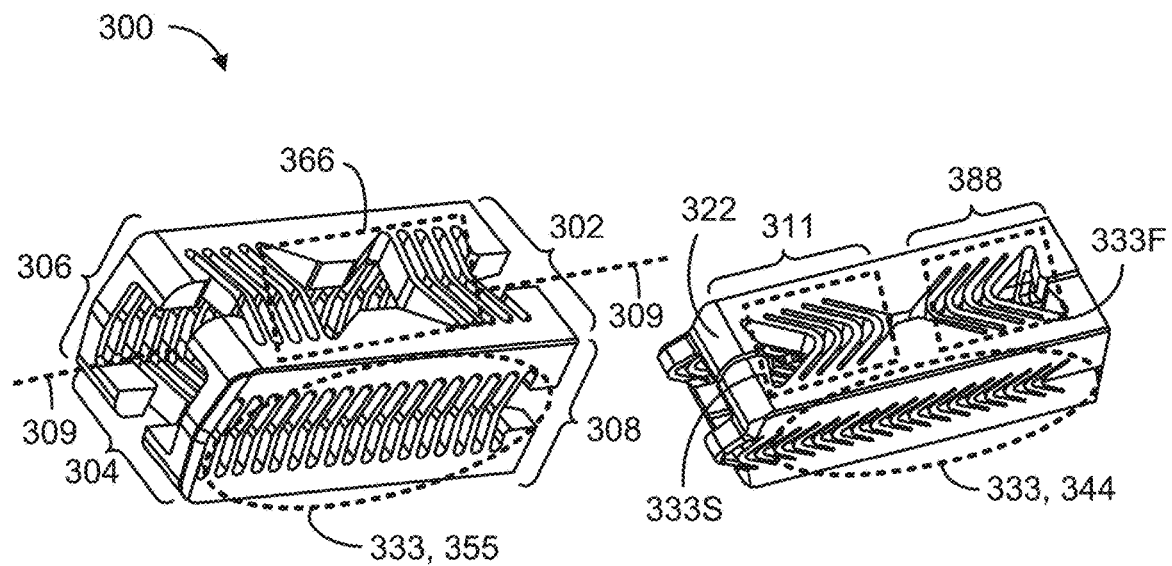
FIGS. 3A-3D illustrate a bidirectionally-expandable cage for fusing an intervertebral disc space, according to some embodiments.
Figures 3C, 3D:
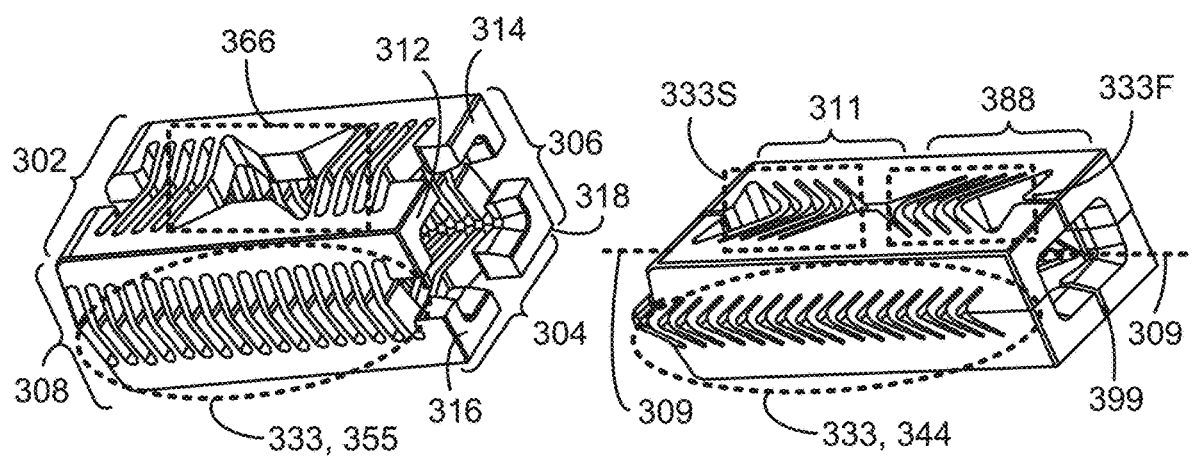

FIGS. 3A-3D illustrate collapsed and expanded views of a bidirectionally-expandable cage for fusing an intervertebral disc space, according to some embodiments. FIGS. 3A and 3C show an expanded configuration, and FIGS. 3B and 3D show a collapsed configuration. The cage 300 can comprise at least 4 walls 302,304,306,308 that form a cylinder having a long axis 309, the at least 4 walls 302, 304,306,308 including a top wall 302 forming a top plane and having a top surface with protuberances (not shown) adapted to contact the top vertebral plate (not shown); a bottom wall 304 forming a bottom plane and having a bottom surface with protuberances (not shown) adapted to contact the bottom vertebral plate (not shown); a first side wall 306 forming a first side wall plane; and, a second side wall 308 forming a second side wall plane. In these embodiments, each of the walls 302,304,306,308 can have at least 2 longitudinal beams, such that a rectangular cylinder can have a total of 4 longitudinal beams 312,314,316,318; and, a plurality of struts 333 that (i) stack in the collapsed state of the cage 300, as shown in FIGS. 3B and 3D, to minimize void space in their respective wall for a low profile entry of the cage 300 both vertically and laterally into a single point of entry (not shown) into an intervertebral disc space (not shown) and (ii) deflect upon expansion to separate the at least 2 longitudinal beams of the total of 4 longitudinal beams 312,314,316,318 in the rectangular cylinder in their respective wall 302,304,306,308. In addition, the cage 300 can be configured to expand laterally in the intervertebral space (not shown) to a size greater than a lateral dimension of the single point of entry (not shown to prevent the bidirectionally-expandable cage 300 from backing out of the annulus fibrosis (not shown) after the expanding shown in FIGS. 3A and 3C.

It should be appreciated that the collapsed configuration includes the design of a low profile entry through the annulus fibrosis to allow for a minimally-invasive procedure. In order to facilitate the use of a minimally-invasive procedure, the low profile entry of the collapsed configuration should be a substantially small area of entry having a diameter ranging, for example, from about 5 mm to about 12 mm for the single point of entry through the annulus fibrosis. In some embodiments, the low profile has an area with a diameter ranging from about 2 mm to about 20 mm, from about 3 mm to about 18 mm, from about 4 mm to about 16 mm, from about 5 mm to about 14 mm, from about 6 mm to about 12 mm, from about 7 mm to about 10 mm, or any range therein. In some embodiments, the low profile has an area with a diameter of 2 mm, 4 mm, 6 mm, 8 mm, 10 mm, 12 mm, 14 mm, 16 mm, 18 mm, or any range therein, including any increment of 1 mm in any such diameter or range therein.

One of skill will appreciate that a variety of strut configurations may be contemplated to minimize void space for the low profile entry of the cage into the intervertebral space. In some embodiments, each wall of the cage has a series of v-shaped struts 333 that (i) stack in a closed-complementary configuration 344 in the collapsed state to minimize void space in their respective wall for the low profile entry of the cage both vertically and laterally into the intervertebral space, and (ii) deflect upon expansion in a plane that is at least substantially parallel to the plane of their respective wall to an open-complementary configuration 355 to separate the at least 2 longitudinal beams of the total of 4 longitudinal beams 312,314,316,318 in the rectangular cylinder in their respective wall and open a bone graft window 366 to pass a bone graft material into the intervertebral space in the expanded configuration. In some embodiments, the cage 300 is configured to accommodate the lateral dimension of the single point of entry ranging from about 5 mm to about 15 mm.

The v-shaped struts can be "V" shaped slots projected through each of the cage walls starting at a distance of 2 mm (0.5-4) from each corner of the cage to effectively render the "V" shaped struts in the mid region of the wall faces, in which the struts can be fabricated as continuous with L shaped beams on the corners. The slots can be cut such that they are projected perpendicular to the faces or angled distally from the outside of the cage to the inside of the cage. The distally angled projection can facilitate insertion of the shims taught herein. And, the proximal faces of the corners of the beams can also have inward, distally angled chamfers to facilitate insertion of the shims taught herein. The struts can be uniform in thickness in the proximal-distal direction. In some embodiments, the struts range from about 0.2 mm to about 1.0 mm, from about 0.3 mm to about 0.9 mm, from about 0.4 mm to about 0.8 mm, from about 0.5 mm to about 0.7 mm in thickness, or any range therein in increments of about 0.1 mm. The vertex of the "V" strut can trace along the center axis of the each of the side faces and can be radiused to dimension of 0.031" (0.005-0.062"), in some embodiments, to prevent stress cracking. Moreover, the shape of the strut or the slot projections can also be C, U, or W, in some embodiments. The struts can be 4 times thicker in the direction perpendicular to the long axis of the cage than in the direction of the long axis of the cage. In some embodiments, this thickness ratio can range from about 2× to about 8×, from about 3× to about 7×, from about 4× to about 6×, about 5×, or any range therein in increments of 1×. This thickness can help maintain a high structural stiffness and strength in the direction perpendicular to the proximal-distal axis so that the transverse cross section (perpendicular to the proximal-distal axis) shape is maintained during and after insertion of the cage into the intervertebral disc space.

In some embodiments, the angle of each strut can range from about 140°-170° as measured at the vertex in the non-stressed state. In these embodiments, the angle facilitates flexion of the legs of each strut towards each other upon moderate inward pressure to collapse the cage for insertion into the disc space. Furthermore the angled strut lies in a plane at least substantially parallel to the plane of it's respective wall, and in some embodiments to the long axis of the cage, so that the flexion does not alter the side wall thickness. This helps to maintain the low profile for insertion while maximizing the lumen size. This geometry combined with the solid beams on the corners helps ensure that the implant has a minimal change in length, less than 15% reduction in length as measured along the long axis, when expanded more than 20% vertically and/or horizontally. As such, the top and bottom of the cage that support the vertebra remain at least substantially constant in length regardless of expansion.

In some embodiments, the cage 300 has v-shaped struts 333 and a bone graft window 366 that (i) complements the v-shaped struts 333 in the collapsed configuration and (ii) opens upon expansion to pass a bone graft material into the intervertebral space in the open-complementary configuration 355, which can also be referred to as an expanded configuration. And, in some embodiments, the cage 300 has a proximal region 311, a proximal end 322, a distal region 388, a distal end 399, and at least one of the at least 4 walls 302,304,306,308 having a first series of v-shaped struts 333 that are configured to stack in a closed-complementary configuration 344 in the collapsed state to minimize void space for the low profile entry of the cage 300 into the intervertebral space; and, deflect upon expansion to an open-complementary configuration 355 to separate the at least 2 longitudinal beams of the total of 4 longitudinal beams 312,314,316,318 in the rectangular cylinder in their respective wall and open a bone graft window 366 adapted to pass a bone graft material into the intervertebral space in the expanded configuration; wherein, the first series of v-shaped struts 333F is located in the proximal region of the cage, the vertices of the first series of v-shaped struts 333F pointing away from the proximal end 322 of the cage 300 and toward the distal end 399 of the cage 300. In some embodiments, the cage 300 can further comprise a second series of v-shaped struts 333S that stack in a closed-complementary configuration 344 in the collapsed state to minimize void space for the low profile entry of the cage 300 into the intervertebral space; and, deflect upon expansion to an open-complementary configuration 355 to separate the at least 2 longitudinal beams of the total of 4 longitudinal beams 312,314,316,318 in the rectangular cylinder in their respective wall and open a bone graft window 366 adapted to pass a bone graft material into the intervertebral space in the expanded configuration; wherein, the second series of v-shaped struts 333S is located in the distal region 388 of the cage 300, the vertices of the second series of v-shaped struts 333S pointing away from the distal end 399 of the cage 300 and toward the proximal end 322 of the cage 300. In such embodiments, the strut configuration can result in the expansion of the first series of v-shaped struts 333F and the second series of v-shaped struts 333S creating a bone graft window 366 that opens to the bow-tie configuration shown in FIGS. 3A and 3C.

One of skill will also appreciate that the cage design provides flexibility in the relative amounts of lateral expansion and vertical expansion, as well as the relative amounts of expansion proximally and distally across the cage in either the lateral or vertical expansions. As such, in some embodiments, the cage is configured such that the ratio of the amount of lateral expansion to the amount of vertical expansion is variable. And, in some embodiments, the cage is configured such that the ratio of the amount of proximal expansion to the amount of distal expansion is variable for lateral expansion or vertical expansion.

Figure 4A:
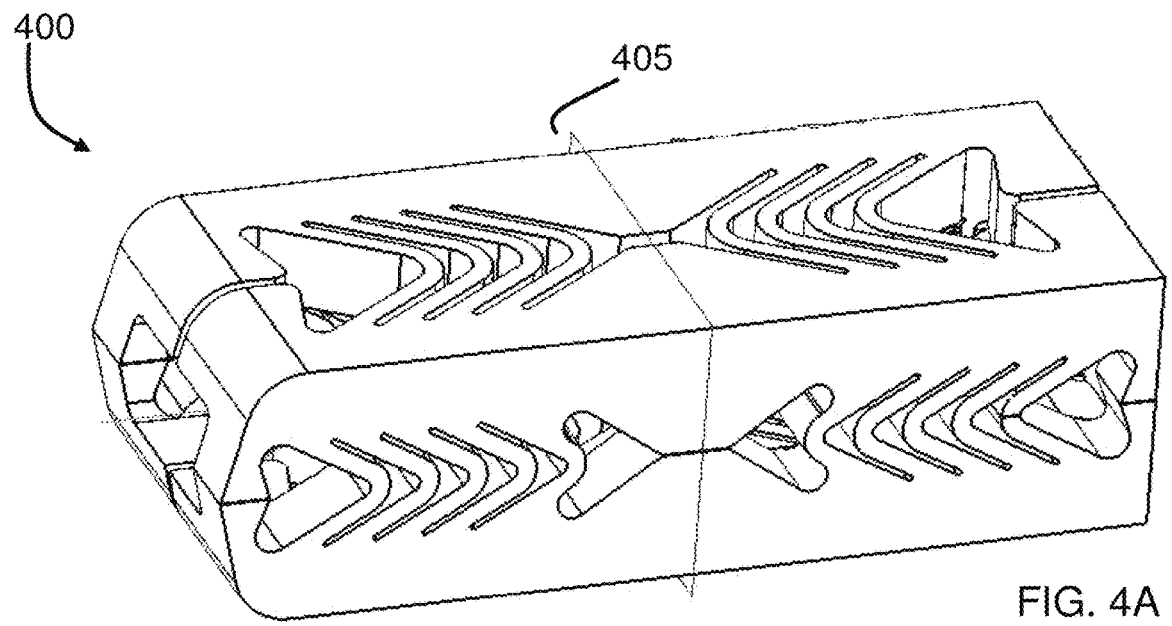
FIGS. 4A and 4B illustrate collapsed and expanded views of a bidirectionally-expandable cage having a bone graft window on each wall for fusing an intervertebral disc space, according to some embodiments.
Figure 4B:
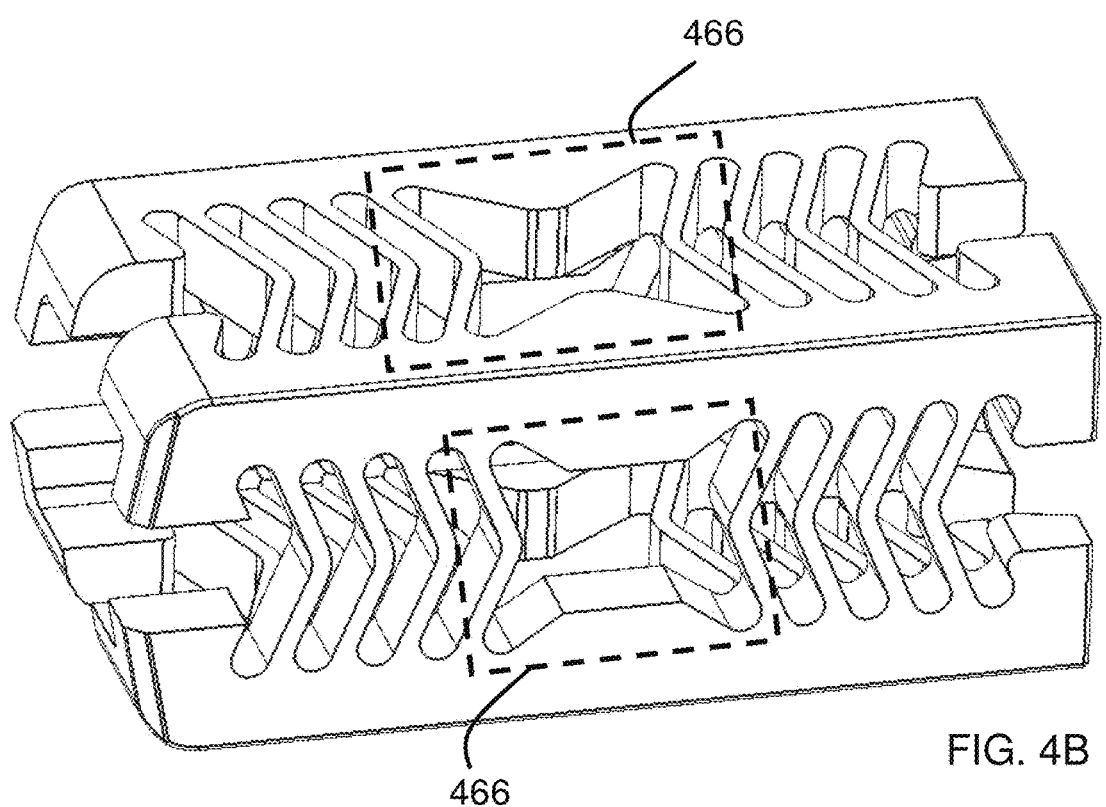
Figure 5A:
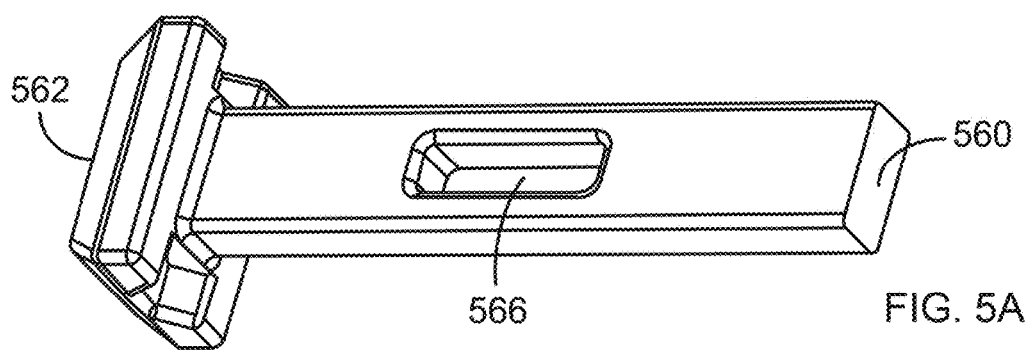
FIGS. 5A-5D illustrate system for fusing an intervertebral disc space, according to some embodiments.
Figure 5B:
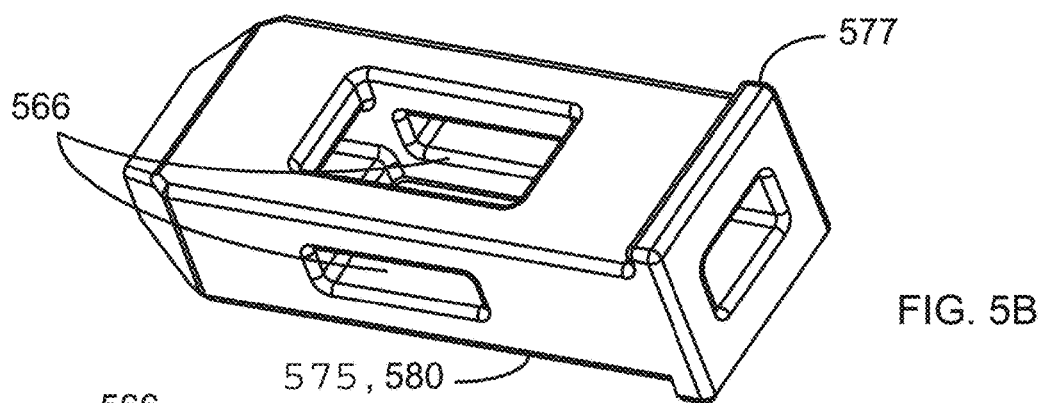
Figure 5C:
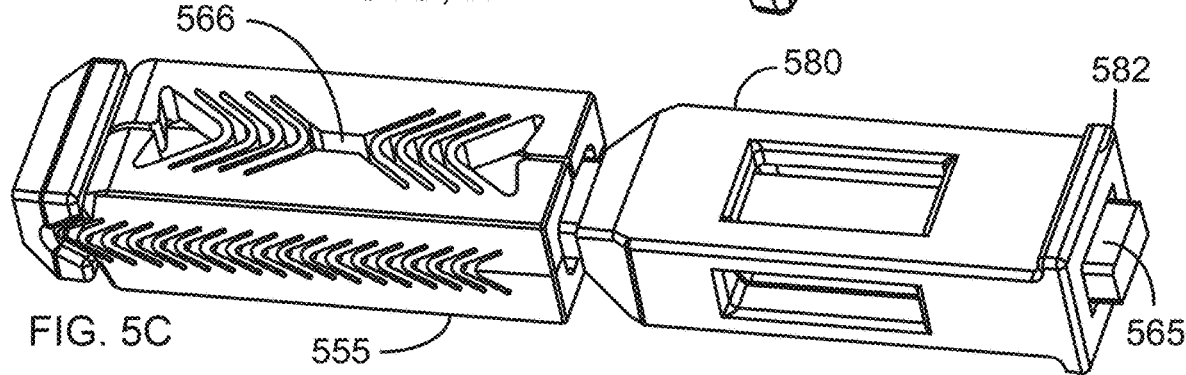
Figure 5D:
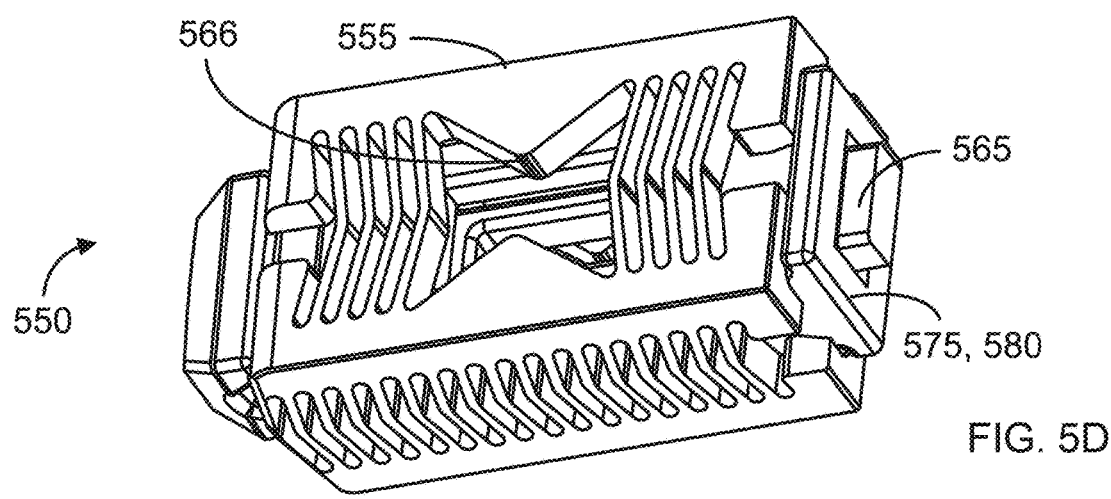

FIGS. 4A and 4B illustrate collapsed and expanded views of a bidirectionally-expandable cage having a bone graft window on each wall for fusing an intervertebral disc space, according to some embodiments. FIG. 4A shows the cage 400 in the collapsed configuration for a low-profile entry 405 into to single point of entry into an intervertebral disc space, and FIG. 4B shows the cage 400 in the expanded configuration to distract the intervertebral disc space and avoid back-out of the cage through the single point of entry after the expansion. As shown, each wall contains a bone graft window 466 for passing bone graft material into the intervertebral disc space.

FIGS. 5A-5D illustrate system for fusing an intervertebral disc space, according to some embodiments. As shown, the system 550 has a cage 555 having an expandable/collapsible bone graft window 566; a shim core 560 having a tapered nose 562 at the distal end of the shim core 560 and a bone graft window 566; a releasably attachable rail beam 565; a pusher (not shown) that slidably translates over the shim core 560 and the rail beam 565; a trial shim 575 having a shoulder 577 and slidably translating over the rail beam 565 and shim core 560 into the cage 555, and a permanent shim 580 having a shoulder 582 and slidably translating over the rail beam 565 and shim core 560 into the cage 555. The system can comprise a bidirectionally-expandable cage having at least 4 walls that form a cylinder having a long axis. The at least 4 walls can include, for example, a top wall forming a top plane and having a top surface with protuberances adapted to contact the top vertebral plate; a bottom wall forming a bottom plane and having a bottom surface with protuberances adapted to contact the bottom vertebral plate; and, a first side wall forming a first side wall plane, and a second side wall forming a second side wall plane. Each of the walls can have at least 2 longitudinal beams; and, a plurality of struts that (i) stack in the collapsed state to minimize void space in their respective wall for a low profile entry of the cage both vertically and laterally into a single point of entry into an intervertebral disc; and, (ii) deflect upon expansion to separate the at least 2 longitudinal beams in their respective wall. In some embodiments, the cage can be configured to expand laterally in the intervertebral space to a size greater than a lateral dimension of the single point of entry to prevent the bidirectionally-expandable cage from backing out of the annulus fibrosis after the expanding. Moreover, the system can include a laterovertical expansion member configured to induce the laterally expanding and the vertically expanding of the cage; and, a core configured to guide the laterovertical expansion member into the cage to induce the laterally expanding and the vertically expanding of the cage.

One of skill will appreciate that the laterovertical expansion member can also be configured to slidably engage with the core to translationally enter the cage in along the long axis of the cage. In some embodiments, the lateral expansion can occur concurrent with the vertical expansion and, in some embodiments, the lateral expansion can occur prior to the vertical expansion, for example, to reduce frictional stress on the cage during the lateral expansion. A two stage shim, for example, can be used. A first stage shim can be inserted to expand the cage laterally before inserting a second stage shim to expand the cage vertically. In some embodiments, the second stage shim can slidably translate along the first stage shim. The shim can be made of any material considered desirable to one of skill, for example, a metal or a polymer. In some embodiments, the shim can comprise a non-resorbable polymer material, an inorganic material, a metal, an alloy, or bone.

One of skill will appreciate that a system can include all or any combination of the above. As such, the teachings also include system for fusing an intervertebral disc space, the system comprising a bidirectionally-expandable cage having a proximal region, a proximal end, a distal region, a distal end, and at least 4 walls, the cage fabricated as a continuous single piece. In these embodiments, the at least 4 walls form a cylinder having a long axis and include a top wall forming a top plane and having a top surface with protuberances adapted to contact the top vertebral plate; a bottom wall forming a bottom plane and having a bottom surface with protuberances adapted to contact the bottom vertebral plate; and, a first side wall forming a first side wall plane, and a second side wall forming a second side wall plane. Each of the walls can have at least 2 longitudinal beams and a plurality of struts.

At least one of the walls can have a first series of v-shaped struts that are configured to stack in a closed-complementary configuration in the collapsed state to minimize void space for a low profile entry of the cage through a single point of entry into an intervertebral disc space; and, deflect upon expansion to an open-complementary configuration to separate the at least 2 longitudinal beams in their respective wall and open a bone graft window adapted to pass a bone graft material into the intervertebral space in the expanded configuration. The first series of v-shaped struts can be located in the proximal region of the cage, the vertices of the first series of v-shaped struts pointing away from the proximal end of the cage and toward the distal end of the cage; and, the cage can be configured to expand laterally in the intervertebral space to a size greater than a lateral dimension of the single point of entry to prevent the bidirectionally-expandable cage from backing out of the annulus fibrosis after the expanding. A laterovertical expansion member can be configured to induce the laterally expanding and the vertically expanding of the cage; and, a core can be configured to guide the laterovertical expansion member into the proximal end of the cage, and along the long axis of the cage, to expand the cage laterally and vertically. Moreover, the laterovertical expansion member can slidably engage with the core to translationally enter the cage along the long axis of the cage.

One of skill will appreciate that the systems and system components can be manufactured using any method known to one of skill in the manufacture of such intricate metal and/or polymeric components. For example, the cage can be fabricated in a partially expanded state or a fully expanded state. Moreover, the cage can be manufactured to have no internal stress or strain in the partially or fully expanded state when no external loading is applied.

The system components can comprise any suitable material, or any combination of materials, known to one of skill. For example, all components can be metal, all components can be plastic, or the components can be a combination of metal and plastic. One of skill will appreciate that the cages can have performance characteristics that are near that of a bone structure, in some embodiments, such that the scaffoldings are not too stiff or hard, resulting in a localized loading issue in which the scaffolding puts too much pressure on native bone tissue, and likewise such that the scaffoldings are too flexible or soft, resulting in a localized loading issue in which the bone tissue puts too much pressure on the scaffolding. A radio-opaque material can be employed to facilitate identifying the location and position of the scaffolding in the spinal disc space. Examples of such materials can include, but are not limited to, platinum, tungsten, iridium, gold, or bismuth.

One of skill can select materials on the basis of desired material performance characteristics. For example, one of skill will look to performance characteristics that can include static compression loading, dynamic compression loading, static torsion loading, dynamic torsion loading, static shear testing, dynamic shear testing, expulsion testing, and subsidence testing. The parameters for upper and lower limits of performance for these characteristics can fall within the range of existing such spinal devices that bear the same or similar environmental conditions during use. For example, a desired static compression loading can be approximately 5000N. A desired dynamic compression loading can have an asymptotic load level of ≥3000N at $5 \times 10^6$ cycles or ≥1500N at $10 \times 10^6$ cycles. The desired load level can range, for example, from about 1.0× to about 2.0×, from about 1.25× to about 1.75×, or any range therein in increments of 0.1×, the vertebral body compression strength. Examples of standard procedures used to test such performance characteristics include ASTM F2077 and ASTM F2624.

Examples of suitable materials can include non-reinforced polymers, carbon-reinforced polymer composites, PEEK (polyether ketone) and PEEK composites, polyetherimide (ULTEM), polysulfone, polyimide, polyamide or carbon fiber. Other examples include metals and alloys comprising any one or more components including, but not limited to, shape-memory alloys, nickel, titanium, titanium alloys, cobalt chrome alloys, stainless steel, ceramics and combinations thereof. In some embodiments, the components are all titanium or titanium alloy; all PEEK; or a combination of titanium or titanium alloy and PEEK. In some embodiments, the cage comprises titanium or titanium alloy, and the shim comprises PEEK. In some embodiments, the scaffolding can comprise a metal frame and cover made of PEEK or ULTEM. Examples of titanium alloys can include alloys of titanium, aluminum, and vanadium, such as $Ti_6Al_4V$ in some embodiments.

In some embodiments, the cage can be fabricated from strong and ductile polymers having a tensile modulus of about 400,000 psi or more, and a tensile strength of about 14,000 psi or more. Such polymers may also have the ability to strain more than 4% to break, and perhaps at least 20% to break in some embodiments. The materials can be stiffened by being filled with glass fibers or carbon fibers in some embodiments.

Bone ingrowth is desirable in many embodiments. As such, the scaffolding can comprise materials that contain holes or slots to allow for such bone ingrowth. Consistently, the scaffoldings can be coated with hydroxyapatite, or other bone conducting surface, for example, bone morphogenic protein, to facilitate bone ingrowth. Moreover, the surfaces of the scaffoldings can be formed as rough surfaces with protuberances, insets, or projections of any type known to one of skill, such as teeth or pyramids, for example, to grip vertebral endplates, avoid migration of the scaffolding, and encourage engagement with bone ingrowth.

The methods and systems provided herein include the use of bone graft materials known to one of skill. Materials which may be placed or injected into the intevertebral space include solid or semi-solid grafting materials, bone from removed from patient's facet, an iliac crest harvest from the patient, and bone graft extenders such as hydroxyapatite, demineralized bone matrix, and bone morphogenic protein. Examples of solid or semi-solid grafting material components include solid fibrous collagen or other suitable hard hydrophilic biocompatible material. Some materials may also include swelling for further vertical expansion of the intervertebral disc space.

The systems taught herein can be provided to the art in the form of kits. A kit can contain, for example, a cage, a vertical expansion member, and a bone graft material. In some embodiments, the kit will contain an instruction for use. The vertical expansion member can be any vertical expansion mechanism or means taught herein. For example, the vertical expansion member can be a shim. In some embodiments, the kit includes a graft-injection shim for temporarily distracting the intervertebral space, the graft-injection shim having a port for receiving and distributing the bone graft material in the intervertebral space. In these embodiments, the graft-injection shim can remain as a permanent shim or be removed and replaced with a permanent shim.

Figure 6:
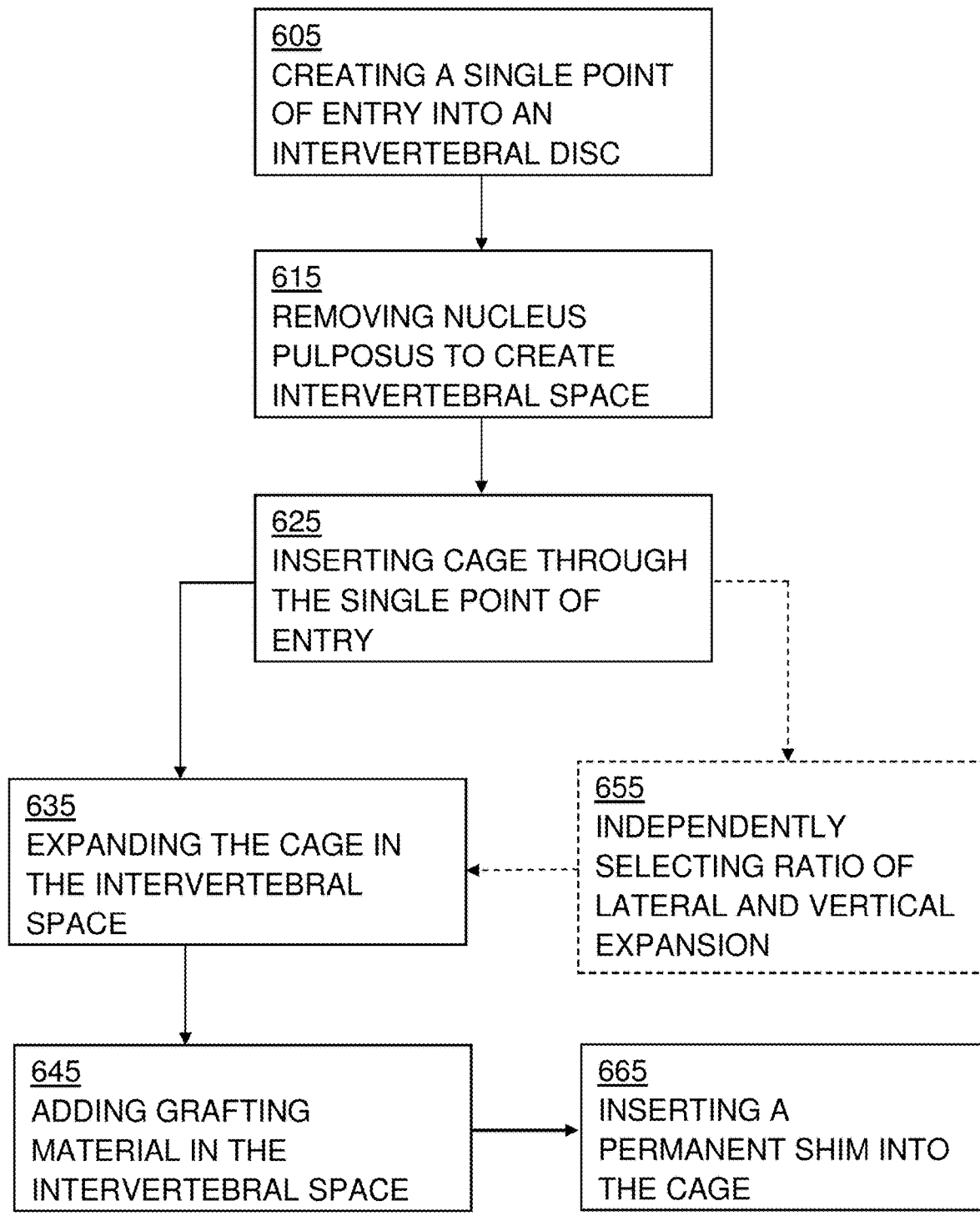
FIG. 6 is a diagram of a method of using a bidirectionally-expandable cage, according to some embodiments.
Figure 7A:
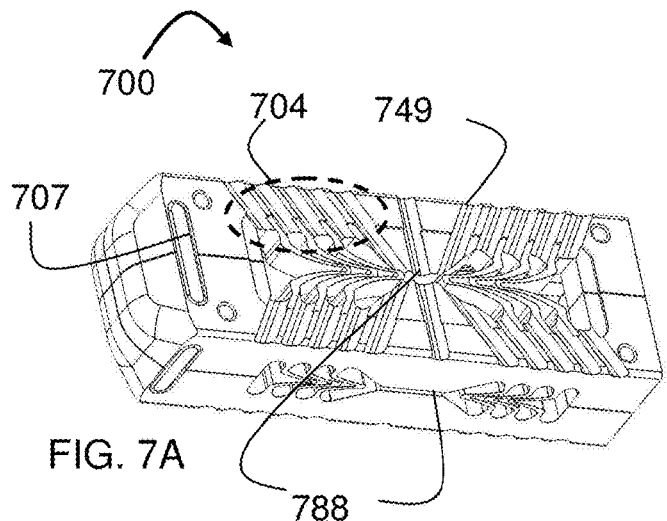
FIGS. 7A-7F illustrate some additional features of graft distribution systems, according to some embodiments.
Figure 7B:
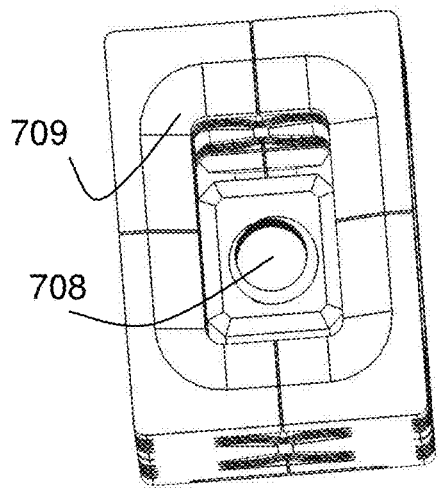
Figure 7C:
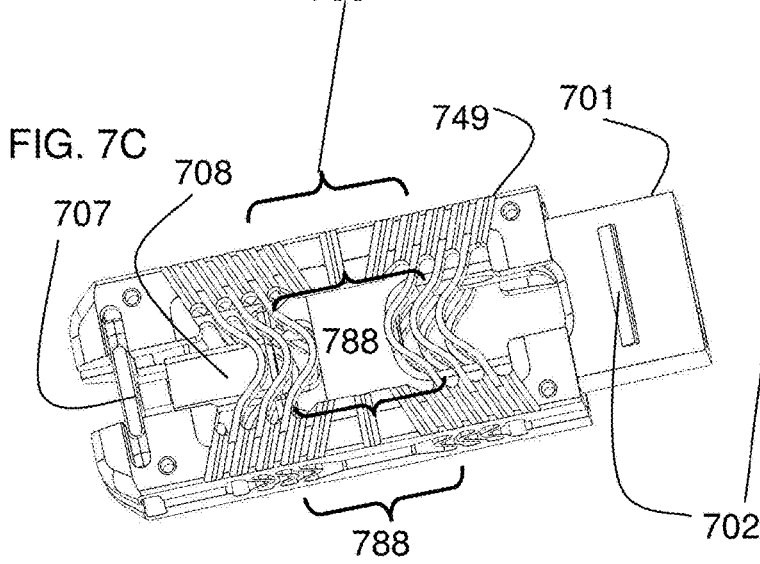
Figure 7D:
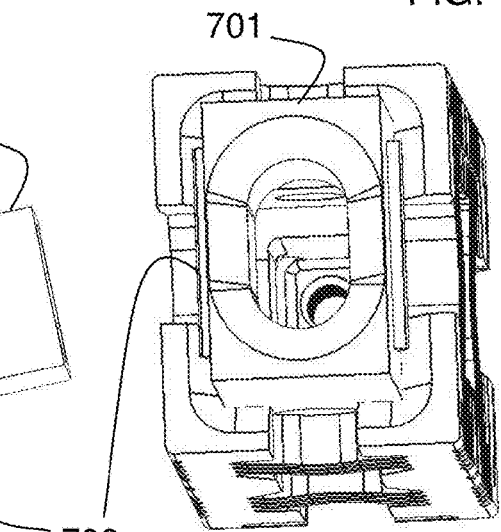
Figure 7E:
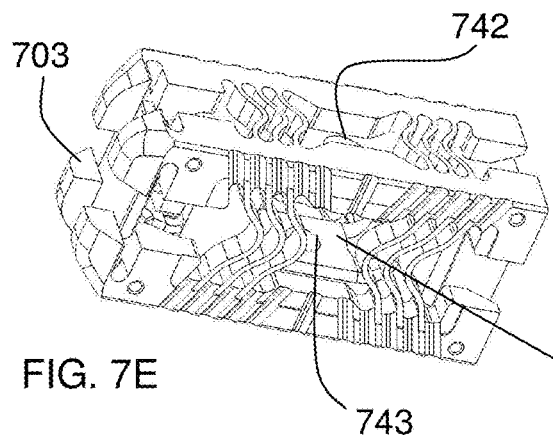
Figure 7F:
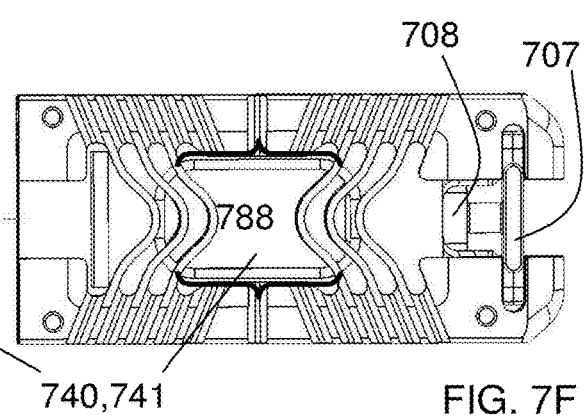

FIG. 6 is a flowchart of a method of using a bidirectionally-expandable cage, according to some embodiments. The methods can include creating 605 a single point of entry into an intervertebral disc, the intervertebral disc having a nucleus pulposus surrounded by an annulus fibrosis, and the single point of entry having a lateral dimension created through the annulus fibrosis. The methods can also include removing 615 the nucleus pulposus from within the intervertebral through the single point of entry, leaving an intervertebral space for expansion of a bidirectionally-expandable cage within the annulus fibrosis, the intervertebral space having a top vertebral plate and a bottom vertebral plate. The methods can also include inserting 625 a bidirectionally-expandable cage through the single point of entry into the intervertebral space. Moreover, the methods can include expanding 635 the cage in the intervertebral space both laterally and vertically, adding 645 a grafting material to the intervertebral space through the single point of entry, and inserting 665 a permanent shim into the cage.

One of skill will appreciate having the ability to control the amounts of vertical expansion and lateral expansion of the cage to accommodate a variety of applications, for example, to accommodate a variety annulotomy dimensions used for the single point of entry. As such, in some embodiments, the expanding 635 includes selecting 655 an amount of lateral expansion independent of an amount of vertical expansion. The lateral expanding of the cage can be selected, for example, to exceed the lateral dimension of the single point of entry through an annulotomy by a desired amount to avoid, or prevent, the cage from backing out of the intervertebral space after expansion.

As such, methods of fusing an intervertebral space are provided herein using any of the graft distribution systems taught herein. The methods can include creating a single point of entry into an intervertebral disc, the intervertebral disc having a nucleus pulposus surrounded by an annulus fibrosis, and the single point of entry having the maximum lateral dimension created through the annulus fibrosis. The methods can also include removing the nucleus pulposus from within the intervertebral disc through the single point of entry, leaving the intervertebral space for expansion of the graft distribution system within the annulus fibrosis, the intervertebral space having the top vertebral plate and the bottom vertebral plate. The methods can also include inserting the laterovertically expanding frame in the collapsed state through the single point of entry into the intervertebral space; and, inserting the central beam into the frame to form the graft distribution system. Moreover, the methods can also include adding a grafting material to the intervertebral space through the entry port.

FIGS. 7A-7F illustrate some additional features of graft distribution systems, according to some embodiments. The graft distribution systems 700 provided herein have at least a top exit port 740 and a bottom exit port 741 in the grafting portion of the central beam 701, but they can also contain side ports 742, 743, such that there at least 4 graft distribution ports in some embodiments. In some embodiments, the central beam 701 further comprises a first side graft port 742 and a second side graft port 743, in addition to a locking clip 702 at the proximal end of the central beam. In some embodiments, the laterovertically-expanding frame 749 can be a monolithically integral frame, optionally having a "bullet nose" 703 at the distal end of the frame for safe position of the cage against the anterior inner annulus in vivo, and adapted to open a graft distribution window 788 on at least the top and bottom sides, as well as the first side and second side in some embodiments containing side ports, upon expansion of the connector elements to facilitate graft distribution within the intervertebral space.

The distal end of the frame 749 can be configured to have a laterovertically operable connection with a guide plate 707 that restricts the first top beam, the first bottom beam, the second top beam, and the second bottom beam to laterovertical movement relative to the guide plate when converting the frame from the collapsed state to the expanded state in vivo. And, in some embodiments, the laterovertically-expandable frame has a lumen, and the guide plate has a luminal side with a connector 708 for reversibly receiving a guide wire for inserting the laterovertically-expandable frame into the intervertebral space. In some embodiments, the frame has a chamfer inside the proximal end of the frame beams to facilitate insertion of central beam. And, in many embodiments, the frames have means for creating friction between the vertebral endplates and the frame, such as protuberances, for example cleat-type structures 704, to further avoid backout.

As can be seen in at least FIG. 7, the bone graft distribution systems provided herein include bone graft windows defined by the connector elements, the bone graft windows opening upon expansion of the laterovertically expanding frame. In some embodiments, the method further comprises opening a bone graft window, wherein the connector elements include v-shaped struts that (i) stack either proximally or distally in a closed-complementary configuration in the collapsed state to minimize void space for a low profile entry of the system both vertically and laterally into the intervertebral space, and (ii) deflect upon expansion to open the bone graft window.

It should be appreciated that the bone graft distribution systems provided herein also allow for independent expansion laterally and vertically by expanding in steps. In some embodiments, the expanding includes selecting an amount of lateral expansion independent of an amount of vertical expansion. And, in some embodiments, the lateral expansion exceeds the width of the annular opening that is the single point of entry into the intervertebral space. For example, the lateral dimension of the single point of entry can range from about 5 mm to about 15 mm in some embodiments. As such, in some embodiments, the expanding includes expanding the laterovertically expanding frame laterally to a width that exceeds the width of the single point of entry; and, inserting the central beam to expand the laterovertically expanding frame vertically to create the graft distribution system.

The bone graft distribution systems provided herein also have additional means for retaining the central beam in the laterovertically expanding frame. In some embodiments, the inserting of the central beam into the laterovertically expanding frame includes engaging a ratchet mechanism comprising a protuberance on the central beam that engages with the laterovertically-expanding frame to prevent the central beam from backing out of the laterovertically-expanding frame after the expanding.

Moreover, the bone graft distribution systems provided herein can be in the form of a kit. The kits can include, for example, a graft distribution system taught herein, a cannula for inserting the graft distribution system into the intervertebral space, a guidewire adapted for guiding the central beam into the laterovertically expanding frame, and an expansion handle for inserting the central beam into the laterovertically expanding frame to form the graft distribution system.

FIGS. 8A-8D illustrate components of a kit, according to some embodiments. FIGS. 8A and 8B illustrate a 4-sided funnel cannula 805 as taught herein having a shaft 810 forming a channel 815, a funnel 820 for guiding a laterovertically expandable frame into an annulus in a low-profile configuration, the cannula shown with an obturator 825 in the channel 815 of the cannula 805, the cannula 805 inserted posterolaterally through an annulotomy 877 in the annulus 888, into an intervertebral space 899, with the distal end of the cannula 805 position near the inner anterior wall of the annulus 888. FIG. 8C illustrates FIG. 8A with a guidewire used to insert the laterovertically expandable frame 749 into the funnel 820 of the cannula 805 to guide the frame 749 into the annulus 888 in the low profile, collapsed state of the frame 749. FIG. 8D illustrates an expansion handle 855 having trigger 856 that pushes a pushrod 857 along the guidewire 866 while holding the guidewire to push on the proximal end of the central beam 701 to insert the central beam 701 into the frame 749 to expand the frame 749 by applying equal, or substantially equal forces: a proximally-directed force, $F_P$, at the connection 708 between the guide plate 707 and the guide wire 866 onto the distal portion of the beams of the frame 749, and a distally-directed force, FD, at the proximal end of the central beam 701.

Figure 9A:
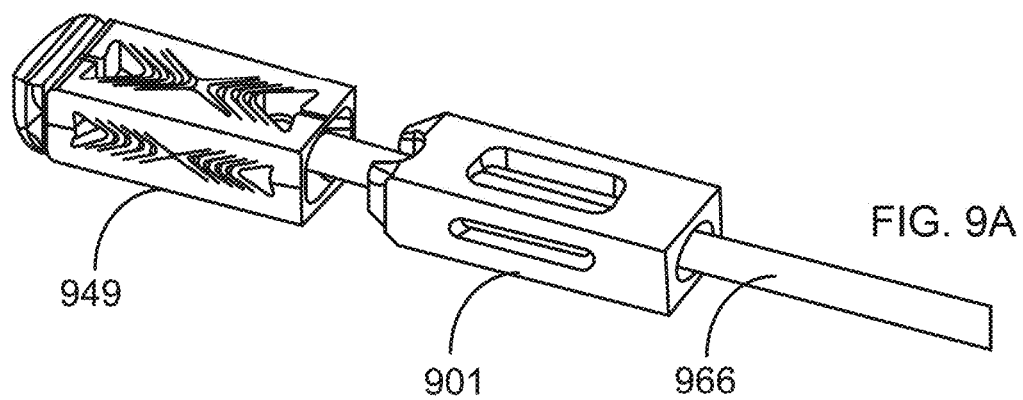
FIGS. 9A-9C illustrate the expansion of a laterovertically-expandable frame in an intervertebral space, according to some embodiments.
Figure 9B:
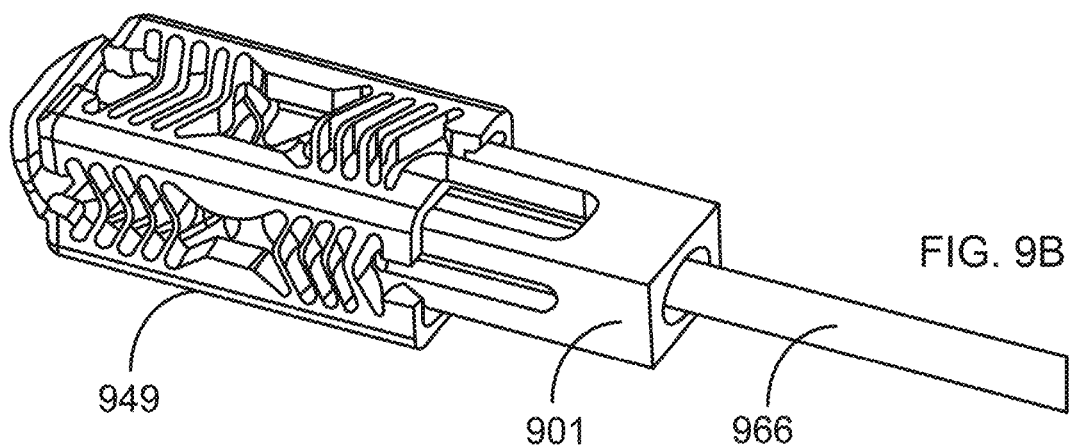
Figure 9C:
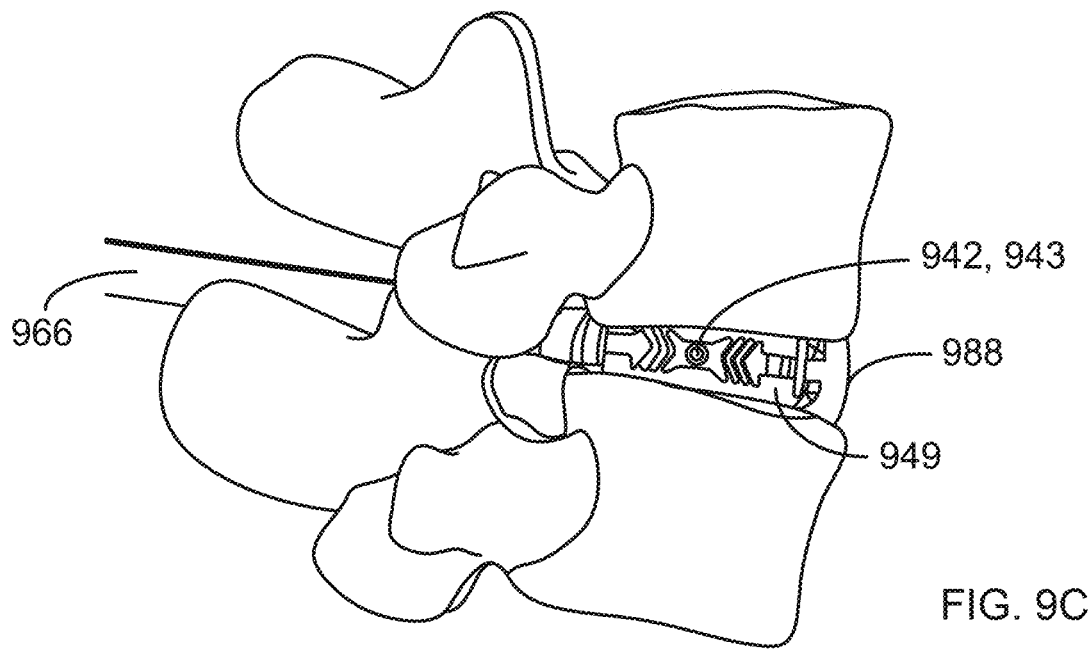

FIGS. 9A-9C illustrate the expansion of a laterovertically-expandable frame in an intervertebral space, according to some embodiments. FIG. 9A shows a collapsed frame 949 receiving a central beam 901 along a guidewire 966. FIG. 9B shows the central beam 901 partially inserted into the frame 949 in an expanded state, the guidewire 966 still in place FIG. 9C shows how the expanded state may appear when inserted posterolaterally and expanded in the intervertebral space in an annulus 988. Side ports 942,943 for bone graft distribution are shown through an open bone graft window in the expanded frame 749.

FIGS. 10A-10C illustrate profiles of an expanded graft distribution system to highlight the exit ports and bone graft windows, according to some embodiments. Profiles of an expanded frame 1049, highlighting bone graft windows 1088 and graft ports 1040,1041,1042,1043 as they may appear in an intervertebral space after an implant procedure. The guidewire 1066 is shown as remaining in place.

Figure 11A:
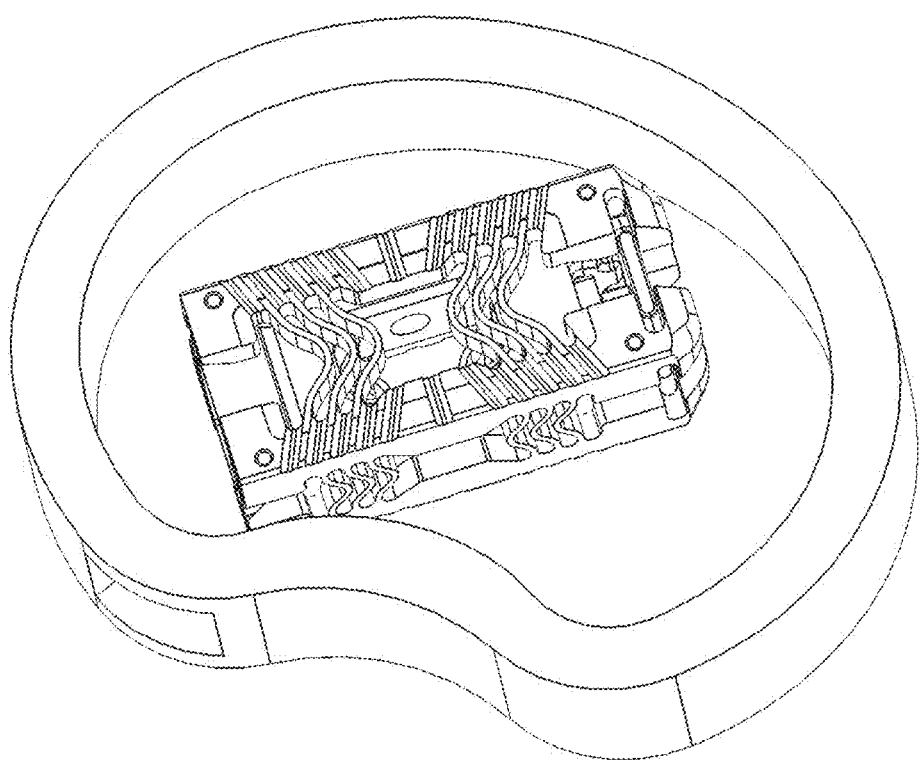
FIGS. 11A and 11B compare an illustration of the graft distribution in place to a test placement in a cadaver to show relative size, according to some embodiments.
Figure 11B:
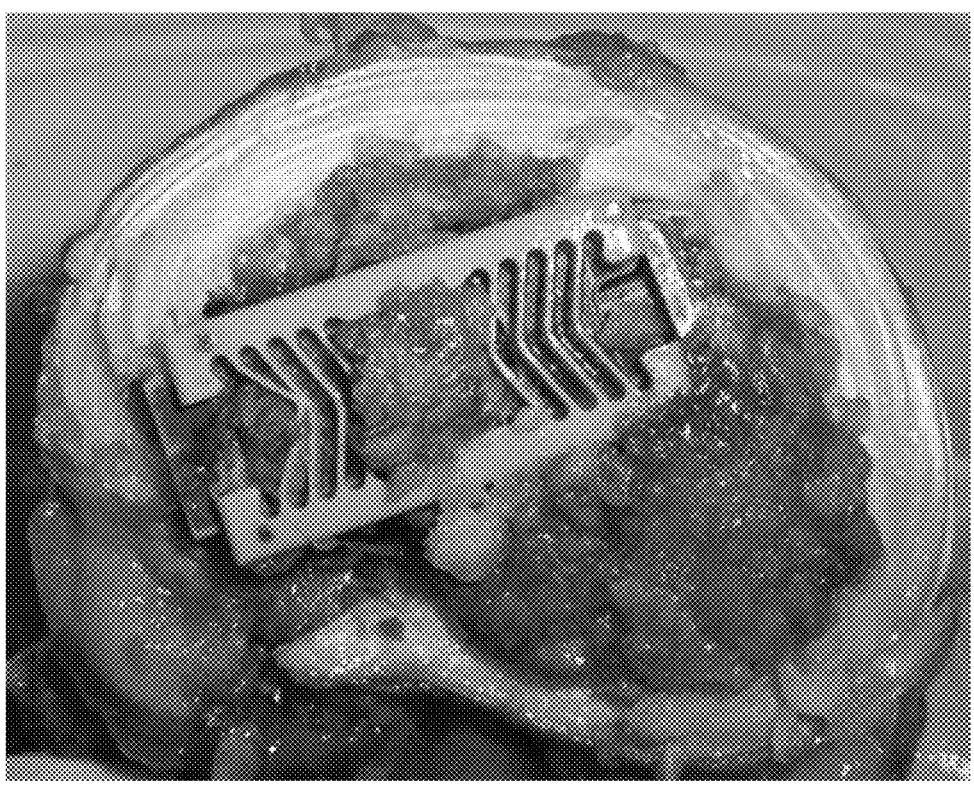
Figure 12A:
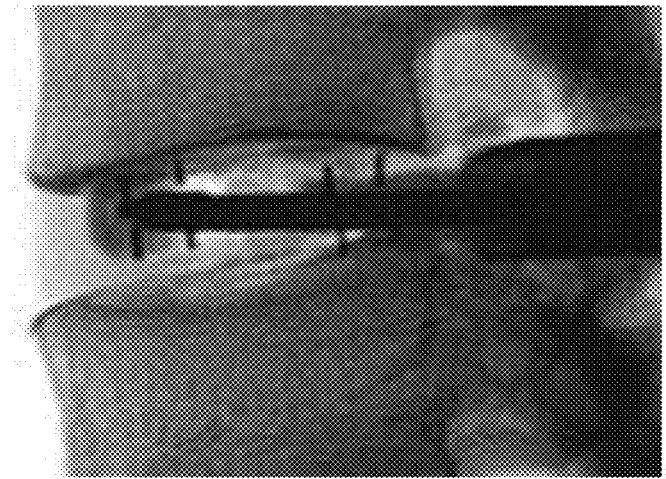
FIGS. 12A-12C show x-rays of a placement in a cadaver, according to some embodiments.
Figure 12B:
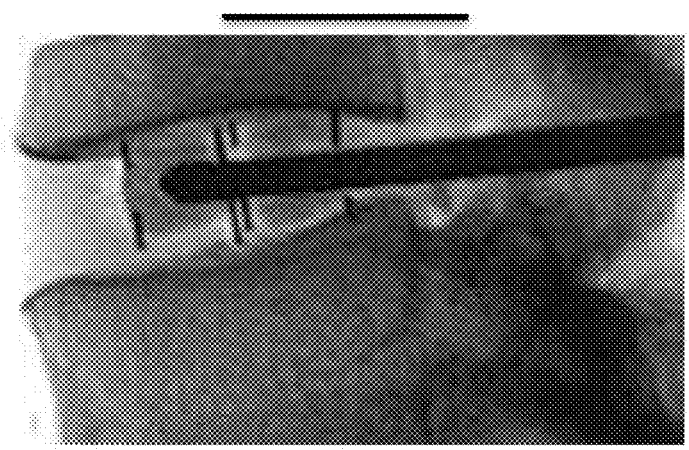
Figure 12C:
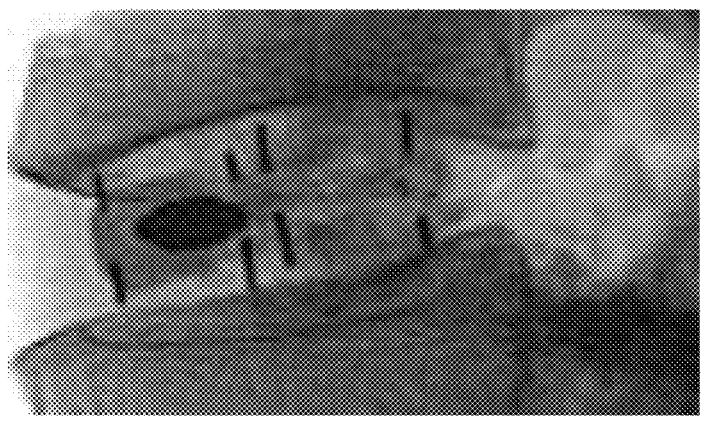

FIGS. 11A and 11B compare an illustration of the graft distribution in place to a test placement in a cadaver to show relative size, according to some embodiments. Likewise, FIGS. 12A-12C show x-rays of a placement in a cadaver, according to some embodiments.

As described above, the frame 149 can be configured such that the central axis of the first top beam 150 is at least substantially on (i) the top plane and (ii) the first side plane; the central axis of the second top beam 160 is at least substantially on (i) the top plane and (ii) the second side plane; the central axis of the first bottom beam 170 is at least substantially on (i) the bottom plane and (ii) the first side plane; and, the central axis of the second bottom beam being at least substantially on (i) the bottom plane and (ii) the second side plane. It should be appreciated that this configuration provides a "top face" framed by the first top beam and the second top beam, a "bottom face" framed by the first bottom beam and the second bottom beam, a "first side face" framed by the first top beam and the first bottom beam, and a "second side face" framed by the second top beam and the second bottom beam.

In some embodiments, it can be desirable to have the frame expand to shape that is predesigned to fit between the top endplate and the bottom endplate of the intervertebral space in a manner that calls, for example, for opposing faces of the frames to be something other than "at least substantially parallel." For example, it may be desired to have the two opposing sides of the frame expand such that the central axis of the first top beam is no longer at least substantially parallel to the central axis of the second top beam. Likewise, it may be desired to have the two opposing sides of the frame expand such that the central axis of the first bottom beam is no longer at least substantially parallel to the central axis of the second bottom beam. Likewise, it may be desired to have the opposing top and bottom sides of the frame expand such that the central axis of the first top beam is no longer at least substantially parallel to the central axis of the first bottom beam. Likewise, it may be desired to have the opposing top and bottom sides of the frame expand such that the central axis of the second top beam is no longer at least substantially parallel to the central axis of the second bottom beam. Or, any combination of the above may be desired. The laterovertically expandable frames taught herein enable each of these desirable configurations.

Figure 13A:
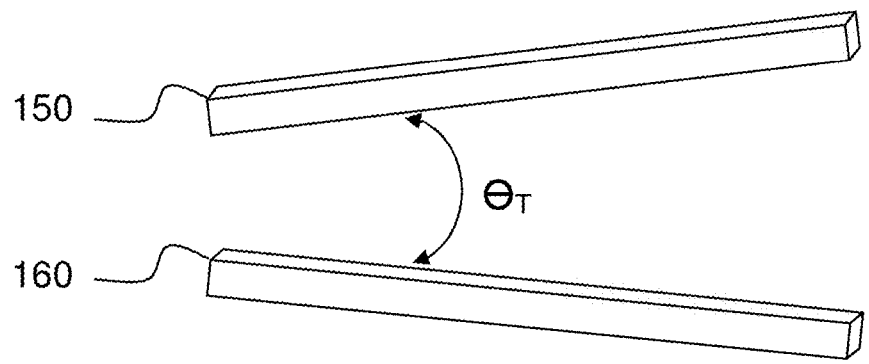
FIGS. 13A-13D show orientations of the first top beam relative to the second top beam, first bottom beam relative to the second bottom beam, first top beam relative to the first bottom beam, and the second top beam relative to the second bottom beam, according to some embodiments.
Figure 13B:
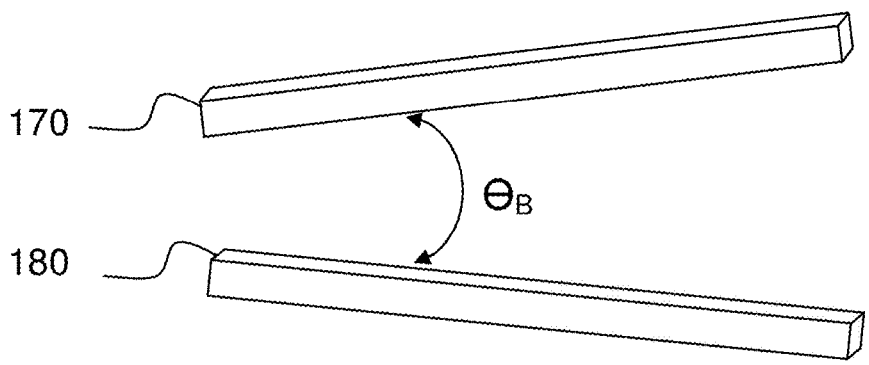
Figure 13C:
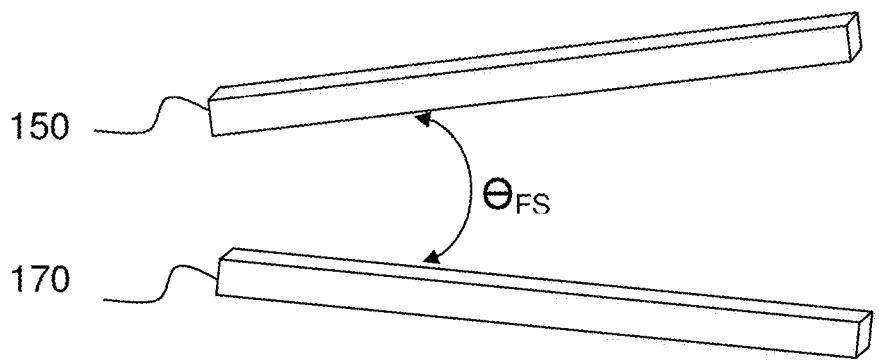
Figure 13D:
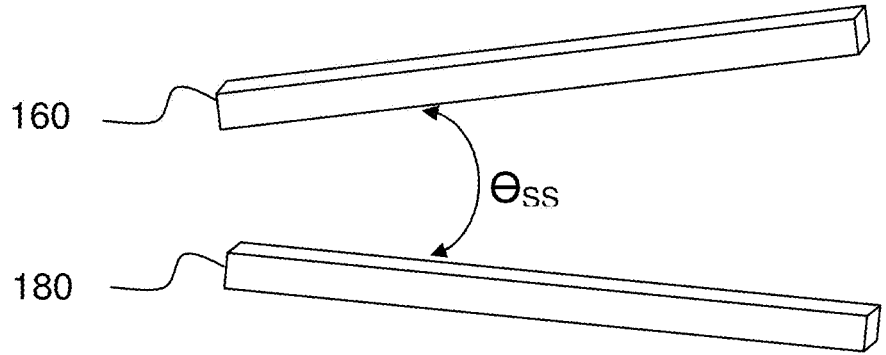

FIGS. 13A-13D show orientations of the first top beam relative to the second top beam, first bottom beam relative to the second bottom beam, first top beam relative to the first bottom beam, and the second top beam relative to the second bottom beam, according to some embodiments. FIG. 13A shows the first top beam 150 relative to the second top beam 160, in which the angle $\theta_T$ is formed by the two beams to shape the top face of the frame. FIG. 13B shows the first bottom beam 170 relative to the second bottom beam 180, in which the angle $\theta_B$ is formed by the two beams to shape the bottom face of the frame. FIG. 13C shows the first top beam 150 relative to the first bottom beam 170, in which the angle $\theta_{FS}$ is formed by the two beams to shape the first side face of the frame. FIG. 13D shows the second top beam 160 relative to the second bottom beam 180, in which the angle $\theta_{SS}$ is formed by the two beams to shape the second side face of the frame. In some embodiments, each of $\theta_T$, $\theta_B$, $\theta_{FB}$, and $\theta_{SS}$ can be independently selected and each can range from 0° to 32°, from 0.5° to 31.5°, from 0.1° to 31.0°, from 1.5° to 30.5°, from 2.0° to 30.0°, from 2.5° to 29.5°, from 3.0° to 29.0°, from 3.5° to 28.5°, from 4.0° to 28.0°, from 4.5° to 27.5°, from 5.0° to 27°, from 5.5° to 26.5°, from 6.0° to 26.0°, from 6.5° to 25.5°, from 7.0° to 25.0°, from 7.5° to 25.5°, from 8.0° to 26.0°, from 8.5° to 26.5°, from 9.0° to 26.0°, from 9.5° to 25.5°, from 10.0° to 25.0°, from 10.5° to 24.5°, from 11.0° to 24.0°, from 11.5° to 23.5°, from 12.0° to 23.0°, from 12.5° to 22.5°, from 13.0° to 22.0°, from 13.5° to 21.5°, from 14.5° to 21.0°, from 15.5° to 20.5°, from 16.0° to 20.0°, from 16.5° to 19.5°, from 17.0° to 19.0°, or any range therein in increments of 0.1°. In some embodiments, each of $\theta_T$, $\theta_B$, $\theta_{FS}$, and $\theta_{SS}$ can be independently selected and each can be about 1°, 2°, 3°, 4°, 5°, 6°, 7°, 8°, 9°, 10°, 11°, 12°, 13°, 14°, 15°, 16°, 17°, 18°, 19°, 20°, 21°, 22°, 23°, 24°, 25°, 26°, 27°, 28°, 29°, 30°, 31°, 32°, 33°, 34°, 35°, or any angle therein in increments of 0.1°.

It should be appreciated that the beams can each be independently designed to have its own, independently selected curvature, whether convex or concave, and the curvatures can be the same or different between beams that share a face of the frame. And, the curvatures can be opposing for beams that form opposing faces of the frame. Moreover, the frame can have a mixture of one or more straight and one or more curved beams.

Given the above, it should be appreciated that the frames can be designed according to nearly any opening bordered by the top vertebral endplate and bottom vertebral endplate of an intervertebral space, as well as according to a given clinical treatment regardless of the opening dimensions prior to treatment. In some embodiments, the top face of the frame can be at least substantially parallel to the bottom face of the frame, whereas the first side face of the frame and the second side face of the frame can be oriented at angles $\theta_T$ and $\theta_B$, wherein $\theta_T$ and $\theta_B$ can be independently selected to be the same or different. Likewise, in some embodiments, the first side face of the frame can be at least substantially parallel to the second side face of the frame, whereas the top face of the frame and the bottom face of the frame can be oriented at angles $\theta_{FS}$ and $\theta_{SS}$, wherein $\theta_{FS}$ and $\theta_{SS}$ can be independently selected to be the same or different. In some embodiments, each of $\theta_T$, $\theta_B$, $\theta_{FS}$, and $\theta_{SS}$ can be independently selected to range from about 5° to about 32°, from about 7° to about 22°, and from about 8° to about 16°, in some embodiments. As such, any of a variety of frames can be constructed from any of a variety of quadrilateral structures having the angles taught herein.

In some embodiments, the systems include a stabilizer that slidably engages with the distal region of the first top beam, the first bottom beam, the second top beam, the second bottom beam, or a combination thereof. The stabilizer serves the function of the guide plate taught herein and can also be configured for retaining the first top beam, the first bottom beam, the second top beam, the second bottom beam, or the combination thereof, from a lateral movement that exceeds the expanded state.

And, in some embodiments, the framing can be configured for engaging with the central beam in vivo to support the framing in the expanded state. Moreover, the connector elements can be struts configured to have a cross-sectional aspect ratio of longitudinal thickness to transverse thickness ranging from 1:2 to 1:8, adapted to maintain structural stiffness in the laterovertically expanding frame in a direction perpendicular to the central frame axis of the expanded state of the frame. In some embodiments, the connector elements can be struts configured to have a cross-sectional aspect ratio of longitudinal thickness to transverse thickness ranging from about 1:1.1 to about 1:20, from about 1:1.2 to about 1:12, from about 1:1.3 to about 1:13, from about 1:1.4 to about 1:14, from about 1:1.5 to about 1:15, from about 1:1.6 to about 1:16 from about 1:1.7 to about 1:17, from about 1:1.8 to about 1:18 from about 1:1.9 to about 1:19, or any range therein. In some embodiments, the connector elements can be struts configured to have a cross-sectional aspect ratio of longitudinal thickness to transverse thickness of about 1:1.1, about 1:1.3, about 1:1.5, about 1:1.7, about 1:1.9, about 1:2.1, about 1:2.3, about 1:2.5, about 1:2.7, about 1:2.9, about 1:3.1, about 1:3.3, about 1:3.5, about 1:3.7, about 1:3.9, about 1:4.1, about 1:4.3, about 1:4.5, about 1:4.7, about 1:4.9, about 1:5.1, about 1:5.3, about 1:5.5, about 1:5.7, about 1:5.9, about 1:6.1, about 1:6.3, about 1:6.5, about 1:6.7, about 1:6.9, about 1:7.1, about 1:7.3, about 1:7.5, about 1:7.7, about 1:7.9, about 1:8.1, about 1:8.3, about 1:8.5, about 1:8.7, about 1:8.9, about 1:9.1, about 1:9.3, about 1:9.5, about 1:9.7, about 1:9.9, about 1:10.1, about 1:10.3, about 1:10.5, about 1:10.7, about 1:10.9, about 1:10.1, about 1:10.3, about 1:10.5, about 1:10.7, about 1:10.9, about 1:11.1, about 1:11.3, about 1:11.5, about 1:11.7, about 1:11.9, about 1:12.1, about 1:12.3, about 1:12.5, about 1:12.7, about 1:12.9, about 1:13.1, about 1:13.3, about 1:13.5, about 1:13.7, about 1:13.9, about 1:14.1, about 1:14.3, about 1:14.5, about 1:14.7, about 1:14.9, about 1:15.1, about 1:15.3, about 1:15.5, about 1:15.7, about 1:15.9, about 1:16.1, about 1:16.3, about 1:16.5, about 1:16.7, about 1:16.9, about 1:17.1, about 1:17.3, about 1:17.5, about 1:17.7, about 1:17.9, about 1:18.1, about 1:18.3, about 1:18.5, about 1:18.7, about 1:18.9, about 1:19.1, about 1:19.3, about 1:19.5, about 1:19.7, about 1:19.9, about 1:20.1, about 1:20.3, about 1:20.5, about 1:20.7, about 1:20.9, or any range there in increments of 0.1 in the longitudinal thickness and/or transverse thickness component of the ratio, such that the strut is adapted to maintain structural stiffness in the laterovertically expanding frame in a direction perpendicular to the central frame axis of the expanded state of the frame.

Figure 14A:
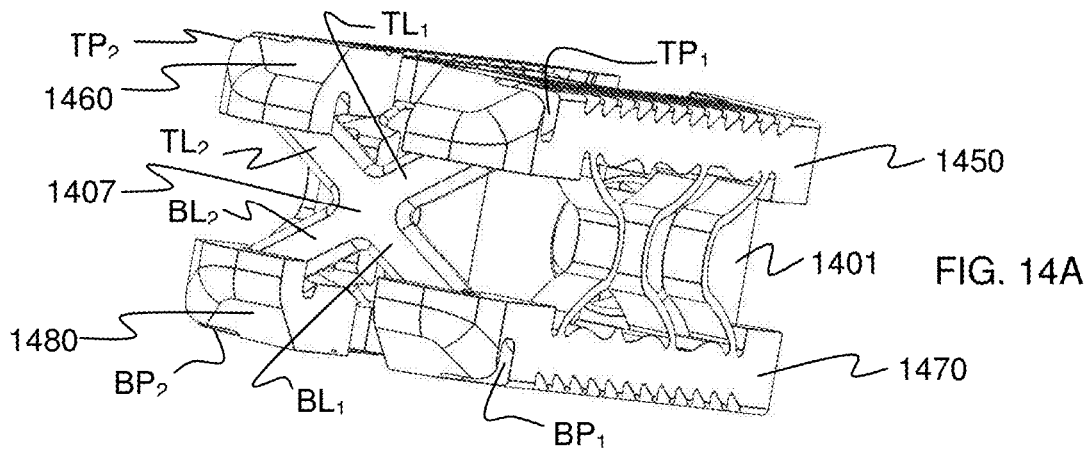
FIGS. 14A-14D illustrate components of a system having a stabilizer, wherein the stabilizer is in an X-configuration, according to some embodiments.

FIGS. 14A-14D illustrate components of a system having a stabilizer, wherein the stabilizer is in an X-configuration, according to some embodiments. As shown in FIG. 14A, the system 1400 can include a stabilizer 1407 that can be in an X-configuration. In some embodiments, the X-configuration can have a first top leg $TL_1$ for slidably-engaging with the first top beam 1450 at an angle $\theta_{1T}$ with the intended lateral movement $LM_{1T}$ of the first top beam 1450, first bottom leg $BL_1$ for slidably engaging with the first bottom beam 1470 at an angle $\theta_{1B}$ with the intended lateral movement $LM_{1B}$ of the first bottom beam 1470, a second top leg $TL_2$ for slidably engaging with the second top beam 1480 at an angle $\theta_{2T}$ with the intended lateral movement $LM_{2T}$ of the second top beam 1460, and a second bottom leg $BL_2$ for slidably engaging with the second bottom beam 1480 at an angle $\theta_{2B}$ with the intended lateral movement $LM_{2B}$ of the second bottom beam 1480.

In some embodiments, each of the angles $\theta_{1T}$, $\theta_{1B}$, $\theta_{2T}$, $\theta_{2B}$, respectively, provide a tensile force for resisting the first top beam 1450, the first bottom beam 1470, the second top beam 1460, and the second bottom beam 1480 from the lateral movement $LM_{1T}$, $LM_{2T}$, $LM_{1B}$, $LM_{2B}$ that exceeds the expanded state. In some embodiments, each of the angles $\theta_{1T}$, $\theta_{1B}$, $\theta_{2T}$, $\theta_{2B}$ can be independently selected from an amount of angulation ranging from about 15° to about 75°, from about 20° to about 75°, from about 25° to about 75°, from about 30° to about 75°, from about 35° to about 75°, from about 55° to about 75°, from about 15° to about 70°, from about 15° to about 65°, from about 15° to about 60°, from about 15° to about 55°, from about 15° to about 50°, from about 15° to about 45°, or any range therein. In some embodiments, each of the angles $\theta_{1T}$, $\theta_{1B}$, $\theta_{2T}$, $\theta_{2B}$ can be independently selected from an amount of angulation that is about 10°, about 15°, about 20°, about 25°, about 30°, about 35°, about 40°, about 45°, about 50°, about 55°, about 60°, about 65°, about 70°, about 75°, about 80°, or any angulation therein in amounts of 1°.

Figure 14B:
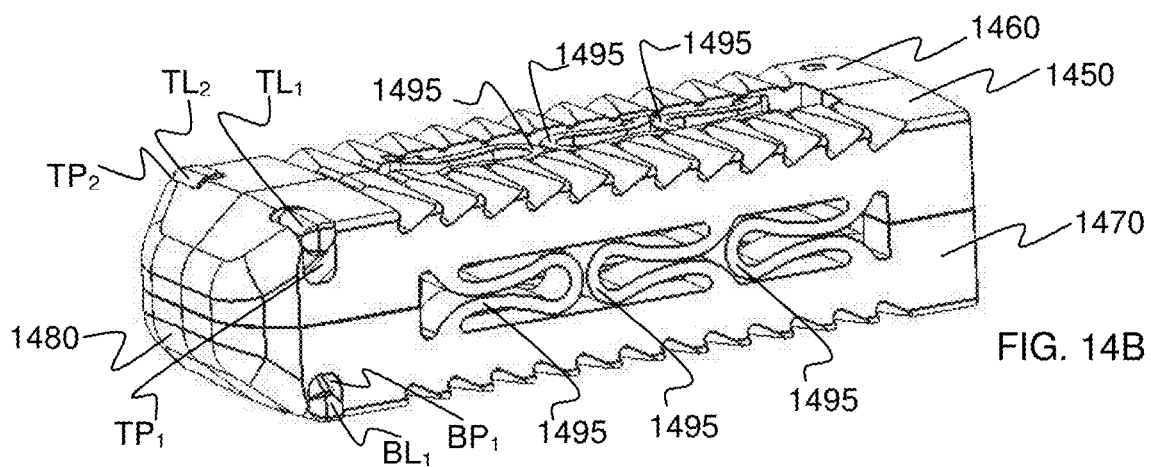
Figure 14C:
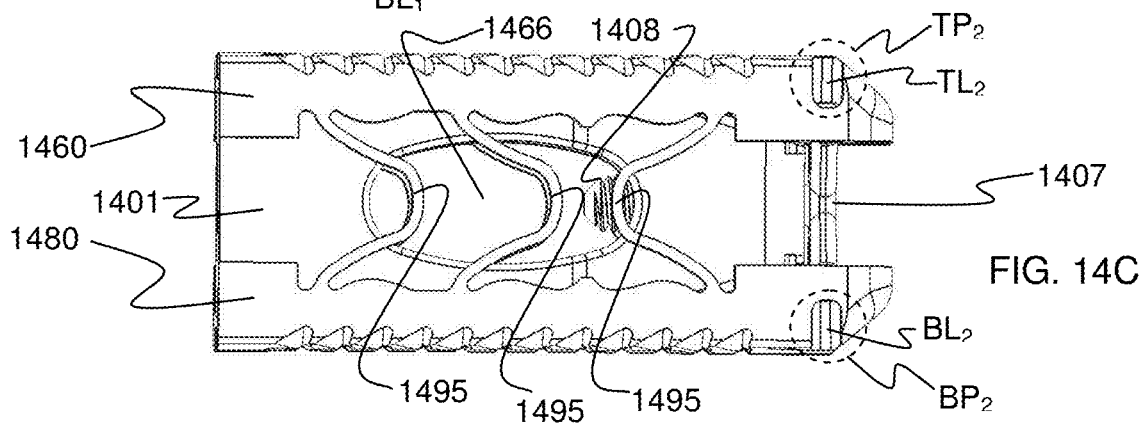
Figure 14D:
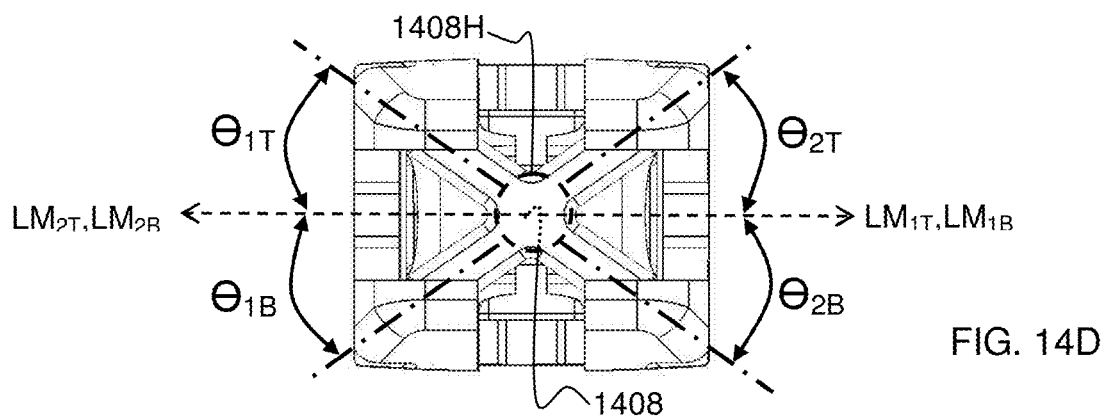
Figure 15A:
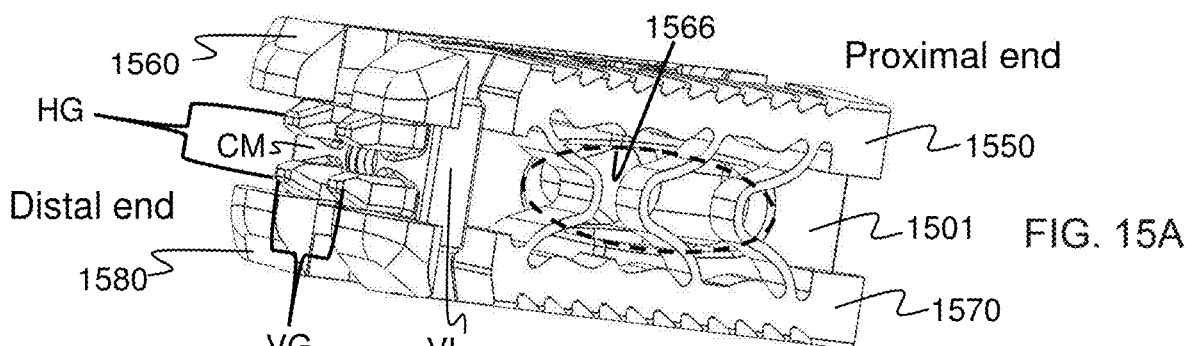
FIGS. 15A-15D illustrate components of a system having a stabilizer, wherein the stabilizer is in an H-configuration, according to some embodiments.
Figure 15B:
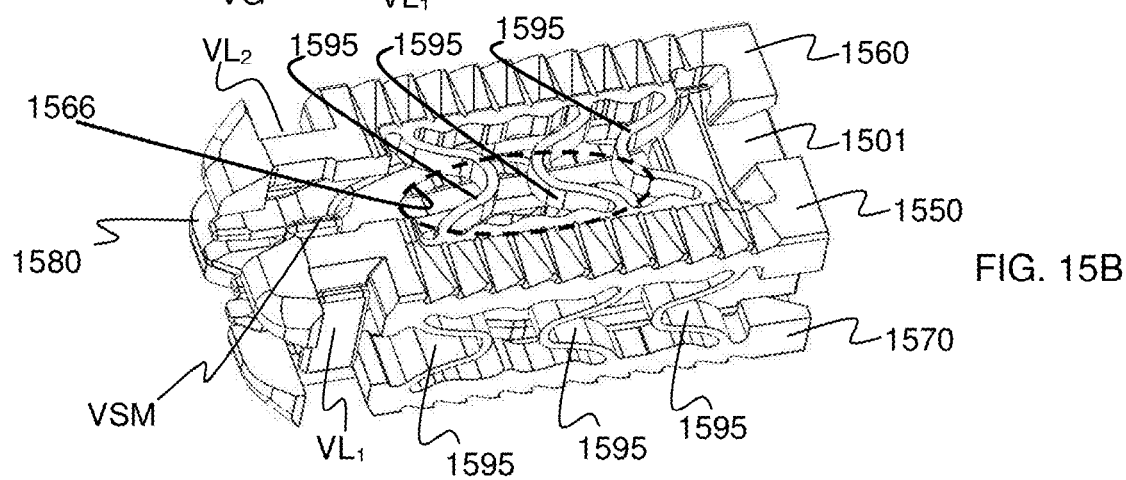
Figure 15C:
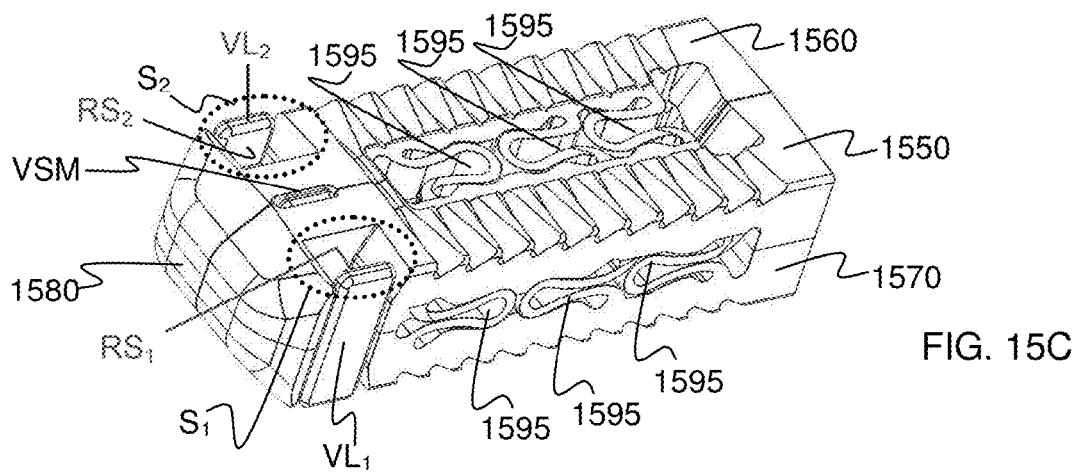
Figure 15D:
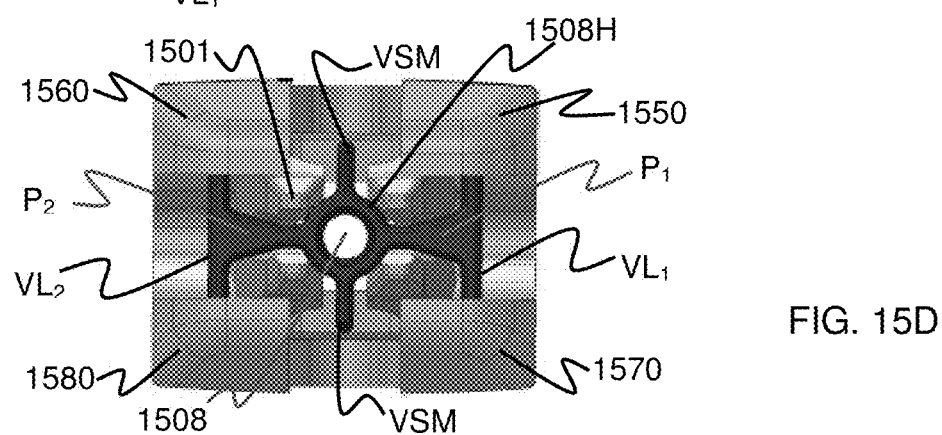

In some embodiments, the stabilizer 1407 further comprises a point of attachment 1408 for releasably attaching a guidewire (not shown) for guiding the central beam 1401 into the laterovertically expanding frame comprising the first top beam 1450, the second top beam 1460, the first bottom beam 1470, and the second bottom beam 1480. And, in some embodiments, the first top leg $TL_1$, the first bottom leg $BL_1$, the second top leg $TL_2$, and the second bottom leg $BL_2$ converge to form a hub 1408H having a point of attachment 1408 on the posterior surface of the hub 1408H for releasably attaching a guidewire (not shown) for guiding the central beam 1401 into the laterovertically expanding frame. The point of attachment might be, for example, a male or female threaded component, or any other releasable connector known to one of skill. And, the beams 1450, 1460, 1470, 1480 can be configured with ports $TP_1$, $TP_2$, $BP_1$, $BP_2$ for passage of the respective legs $TL_1$, $TL_2$, $BL_1$, $BL_2$ of the stabilizer 1407. FIGS. 14B and 14C show the system in a collapsed configuration and expanded side configuration, respectively. In some embodiments, the central beam 1401 can include one or more bone graft distribution ports 1466. And, as in other embodiments taught herein, the beams 1450, 1460, 1470, 1480 can be interconnected using flexible struts 1495.

FIGS. 15A-15D illustrate components of a system having a stabilizer, wherein the stabilizer is in an H-configuration, according to some embodiments. The H-configuration can have a first vertical leg $VL_1$, a second vertical leg $VL_2$, and a cross-member CM that connects the first vertical leg $VL_1$ at least substantially parallel to the second vertical leg $VL_2$, the first vertical leg $VL_1$ including a first retaining surface $RS_1$ for engaging with the first top beam 1550 and the first bottom beam 1570, the second vertical leg $VL_2$ including a second retaining surface $RS_2$ for engaging with the second top beam 1560 and the second bottom beam 1580, and the cross-member CM providing a tensile force for resisting the first top beam 1550, the first bottom beam 1570, the second top beam 1560, and the second bottom beam 1580 from the lateral movement that exceeds the expanded state. In some embodiments, the central beam 1501 has a horizontal groove HG configured complementary to the cross-member CM of the stabilizer 1507, and the horizontal groove HG of the central beam 1501 slidably connects with the cross-member CM in the expanded state. In some embodiments, the cross-member CM further comprises a vertical support member VSM and the central beam 1501 has a vertical groove VG configured complementary to the vertical support member VSM of the stabilizer, and the vertical groove VG of the central beam 1501 slidably connects with the vertical support member VSM in the expanded state. In some embodiments, the stabilizer 1507 further comprises a point of attachment 1508 at a hub 1508H for releasably attaching a guidewire (not shown) adapted for guiding the central beam 1501 into the laterovertically expanding frame comprising the first top beam 1550, the second top beam 1560, the first bottom beam 1570, and the second bottom beam 1580. The point of attachment might be, for example, a male or female threaded component, or any other releasable connector known to one of skill. And, the beams 1550,1560,1570,1580 can be configured with slots $S_1, S_2$ in which the vertical legs $VL_1, VL_2$ can travel during the lateral expansion of the beams 1550,1560,1570,1580 of the expandable frame. And, in some embodiments, cross-member CM includes a first pillar $P_1$ and a second pillar $P_2$ that operably connect at a hub that has the point of attachment 1508 for releasably attaching the guidewire (not shown) for guiding the central beam 1501 into the laterovertically expanding frame. In some embodiments, the central beam 1501 can include one or more bone graft distribution ports 1566. And, as in other embodiments taught herein, the beams 1550,1560,1570,1580 can be interconnected using flexible struts 1595.

Figure 16A:
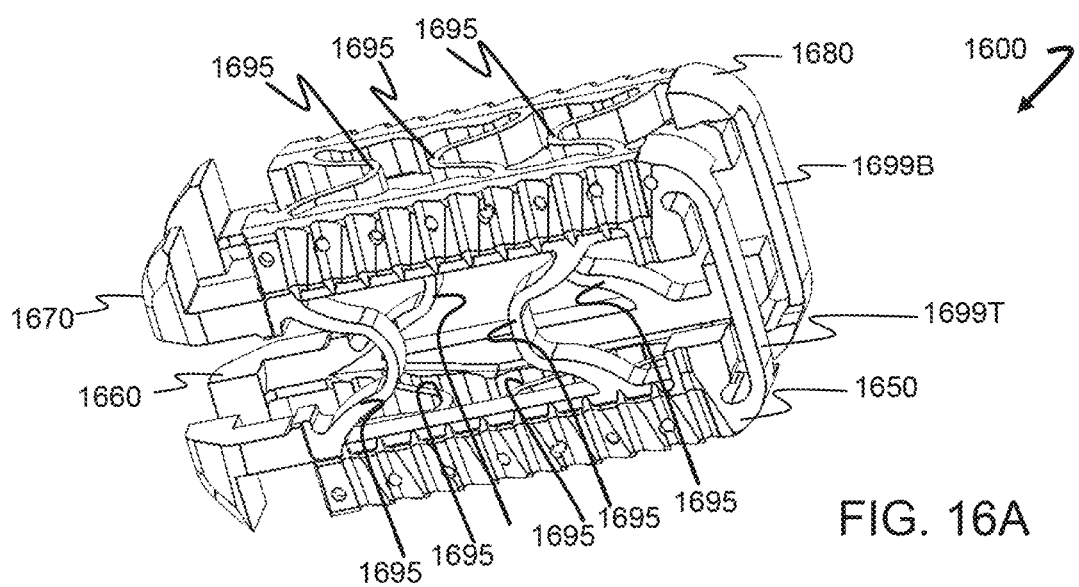
FIGS. 16A-16I illustrate components of a system having a cage with a combination of a stabilizer and a tensioner, and a central beam configured for expanding the cage, according to some embodiments.

FIGS. 16A-16I illustrate components of a system having a cage with a combination of a stabilizer and a tensioner, and a central beam configured for expanding the cage, according to some embodiments. FIGS. 16A-16E show the cage without a central beam to illustrate features of a cage, and FIGS. 16F-16I show the cage with a central beam to illustrate the system in an expanded state. The stabilizer can have any configuration that performs the functions set-forth herein for such a stabilizer. For example, the stabilizer can have an X-configuration or an H-configuration in these embodiments, at least as set-forth herein in at least FIGS. 14A-14D and FIGS. 15A-15D discussed above. FIG. 16A provides a perspective view of a cage 1600 that may be used in such a system, the cage 1600 having a first top beam 1650, a first bottom beam 1670, a second top beam 1660, and a second bottom beam 1680, the beams interconnected by flexible struts 1695 that allow for bilateral expansion and collapse of the cage 1600. Interestingly, in some embodiments, the cage 1600 can include one or more tensioners such as, for example, tension straps 1699.

Figure 16B:
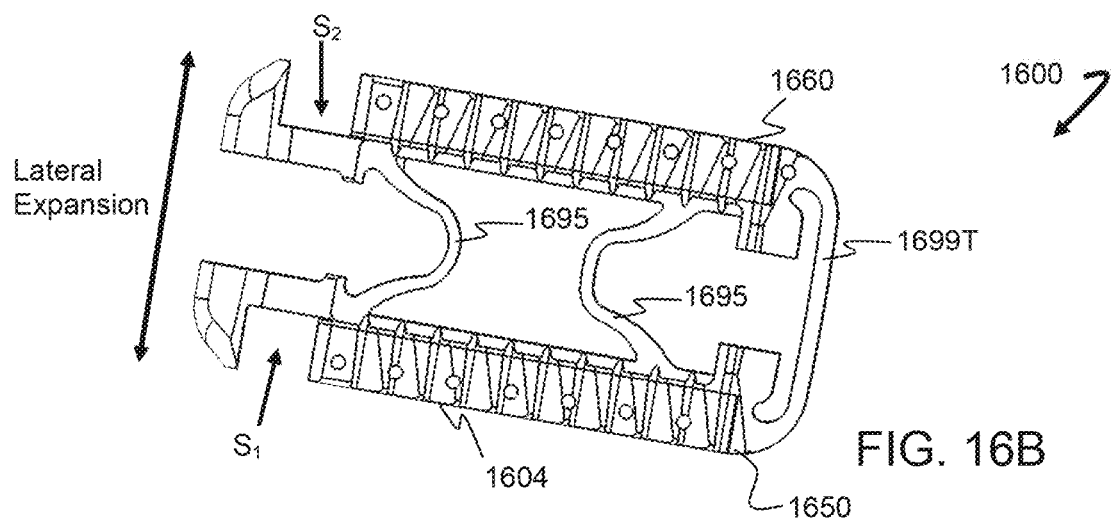
Figure 16C:
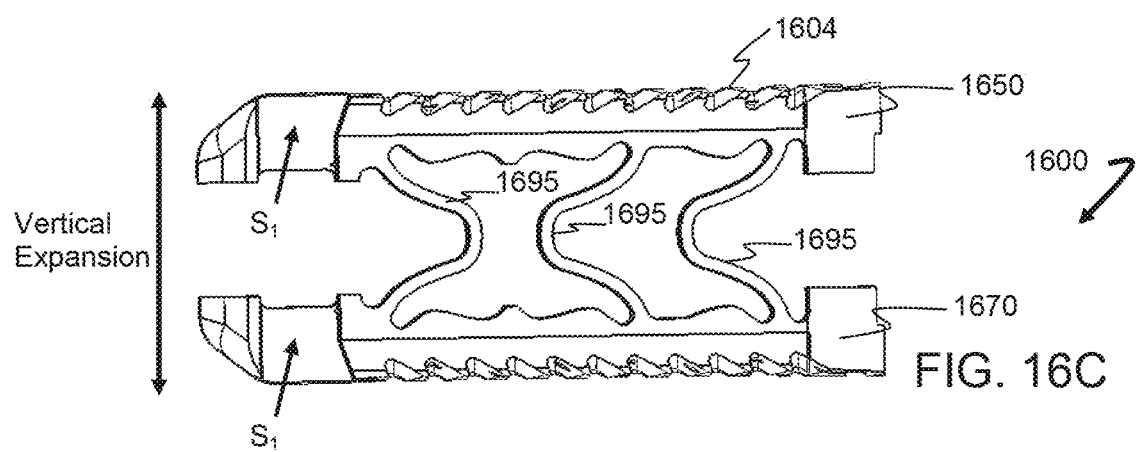

FIG. 16B provides a top perspective view of lateral expansion, for example, of the cage 1600 as it is configured for receiving a stabilizer having an H-configuration. A first pair of recesses $R_1$ are provided in the cage 1600 for receiving a first vertical leg $VL_1$ (see FIGS. 15A-15D), and a second pair of recesses $R_2$ are provided in the cage 1600 for receiving a second vertical leg $VL_2$ (see FIGS. 15A-15D), and a cross-member CM (see FIG. 15A) that connects the first vertical leg $VL_1$ (see FIGS. 15A-15D) at least substantially parallel to the second vertical leg $VL_2$ (see FIGS. 15A-15D), the first vertical leg $VL_1$ (see FIGS. 15A-15D) including a first retaining surface $RS_1$ (see FIG. 15C) for engaging with the first top beam 1650 and the first bottom beam 1670, the second vertical leg $VL_2$ (see FIGS. 15A-15D) including a second retaining surface $RS_2$ (see FIG. 15C) for engaging with the second top beam 1660 and the second bottom beam 1680, and the cross-member CM (see FIG. 15A) providing a tensile force for resisting the first top beam 1650, the first bottom beam 1670, the second top beam 1660, and the second bottom beam 1680 from the lateral movement that exceeds the expanded state. In some embodiments, the central beam 1601 (not shown) has a horizontal groove HG (see FIG. 15A) configured complementary to the cross-member CM (see FIG. 15A) of the stabilizer 1607 (see FIGS. 15A-15D), and the horizontal groove HG (see FIG. 15A) of the central beam 1601 slidably connects with the cross-member CM (see FIG. 15A) in the expanded state. In some embodiments, the cross-member CM (see FIG. 15A) further comprises a vertical support member VSM (see FIGS. 15B and 15C) and the central beam 1601 has a vertical groove VG (see FIG. 15A) configured complementary to the vertical support member VSM (see FIGS. 15B and 15C) of the stabilizer (see FIGS. 15A-15D), and the vertical groove VG (see FIG. 15A) of the central beam 1601 slidably connects with the vertical support member VSM (see FIGS. 15B and 15C) in the expanded state. In some embodiments, the stabilizer 1607 (see FIGS. 15A-15D) further comprises a point of attachment 1608 (see FIG. 15D, 1508) at a hub 1608H (see FIG. 15D, 1508H) for releasably attaching a guidewire (not shown) adapted for guiding the central beam 1601 into the laterovertically expanding frame comprising the first top beam 1650, the second top beam 1660, the first bottom beam 1670, and the second bottom beam 1680. The point of attachment might be, for example, a male or female threaded component, or any other releasable connector known to one of skill. And, as shown in at least FIGS. 16A-16C, the beams 1650,1660,1670,1680 can be configured with slots $S_1, S_2$ in which the vertical legs $VL_1, VL_2$ can travel during the lateral expansion of the beams 1650,1660,1670,1680 of the expandable frame.

In some embodiments, cross-member CM (see FIG. 15A) includes a first pillar $P_1$ (see FIG. 15D) and a second pillar $P_2$ (see FIG. 15D) that operably connect at a hub that has the point of attachment 1608 (see FIG. 15D, 1508) for releasably attaching the guidewire (not shown) for guiding the central beam 1601 into the laterovertically expanding frame. In some embodiments, the central beam 1601 can include one or more bone graft distribution ports 1666. And, as in other embodiments taught herein, the beams 1650,1660, 1670,1680 can be interconnected using flexible struts 1695. Moreover, the beams 1650,1660,1670,1680 can have cleats 1604 to help avoid backout of the cage 1600 from the intervertebral space.

One of skill will appreciate that the tensioner can have any configuration that provides the function sought herein, which is to provide a tension force between beams. As such, the cages taught herein can include a means for providing tension force between the beams. The addition of one or more tensioners can function, for example, to retain the beams 1650,1660,1670,1680 on a central beam 1601. In some embodiments, the function sought is to provide a tension between the first top beam and the second top beam.

In some embodiments, the function sought is to provide a tension between the first bottom beam and the second bottom beam. Likewise, in some embodiments, the function sought is to provide a tension between the first top beam and the second top beam, in addition to a tension between the first bottom beam and the second bottom beam. As shown herein, for example, the tensioners can be a top tension strap 1699T and a bottom tension strap 1699B.

One of skill will appreciate that the configuration of the tensioner can be varied to provide a sufficient tension force between beams of a cage, according to some embodiments. FIGS. 16A-16I show a tension strap configuration that provides a tension force from the elasticity of the material that composes the top and bottom tension straps.

Figure 16D:
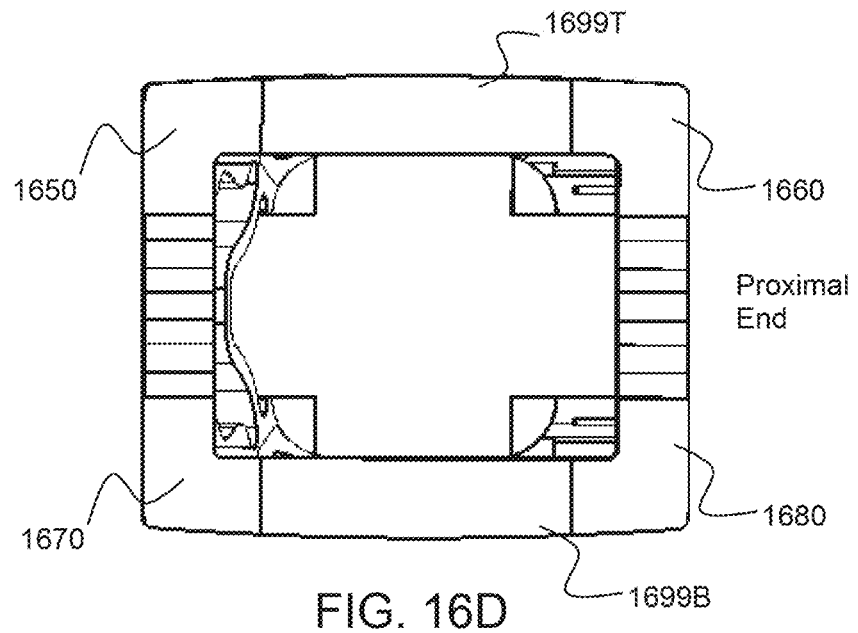
Figure 16E:
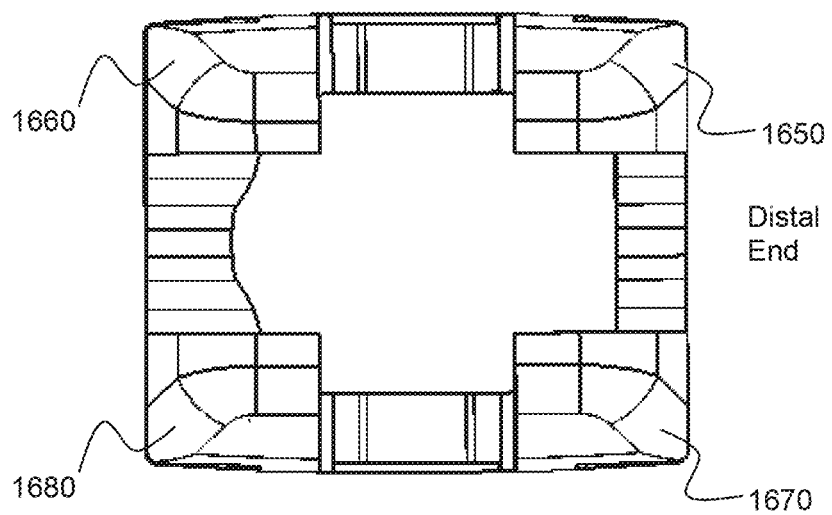
Figure 16F:
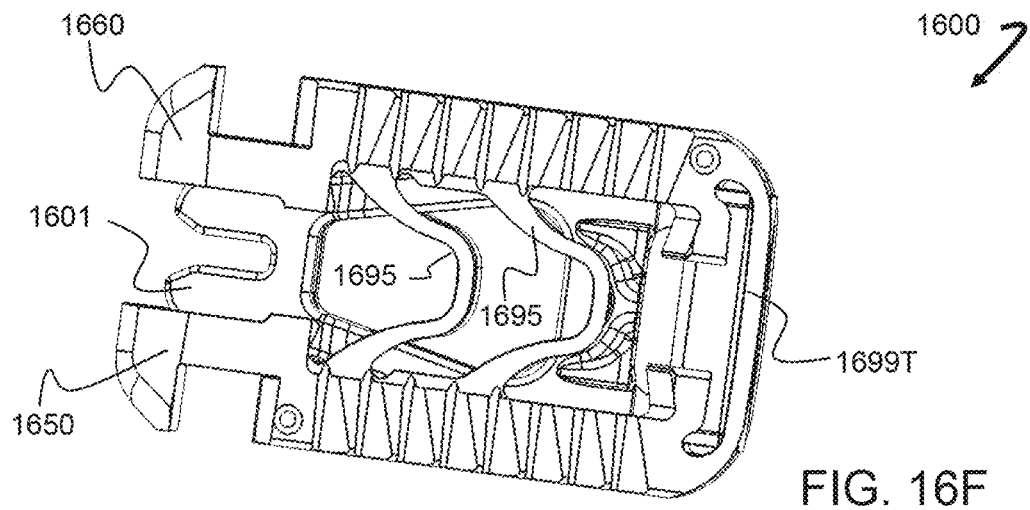
Figure 16G:
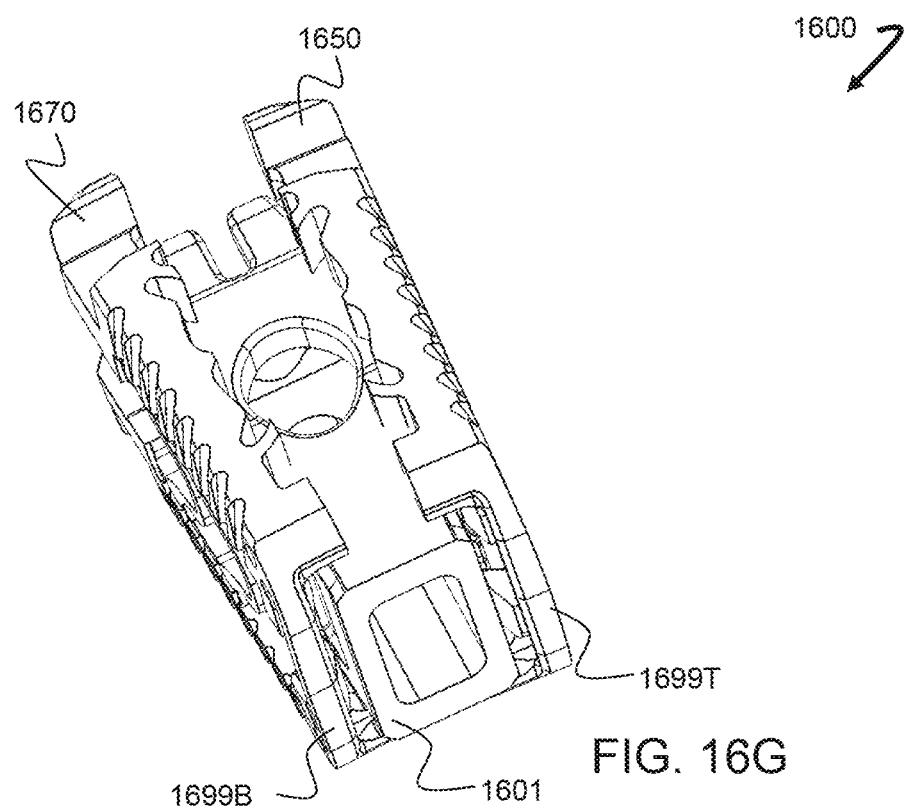
Figure 16H:
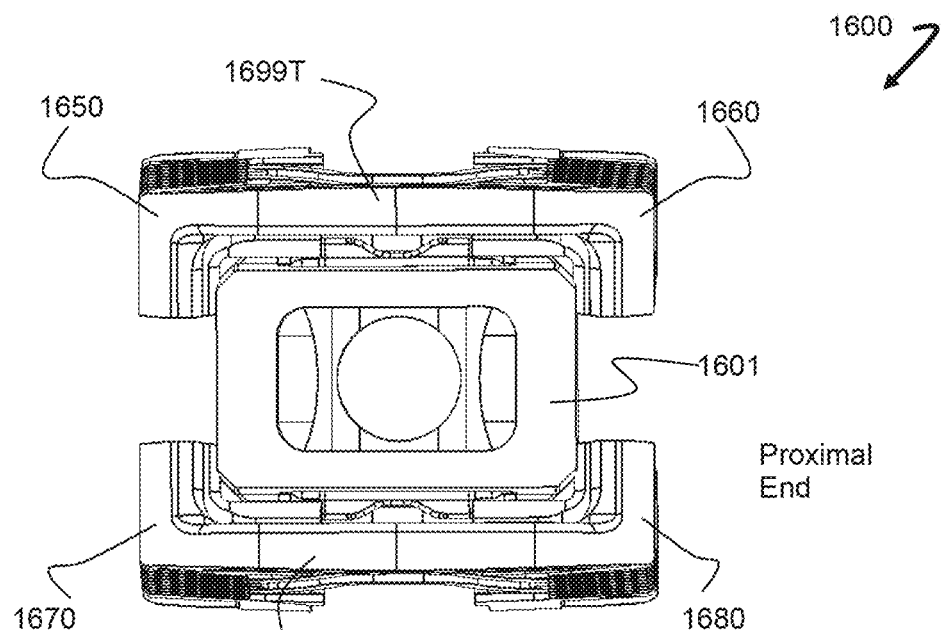
Figure 16I:
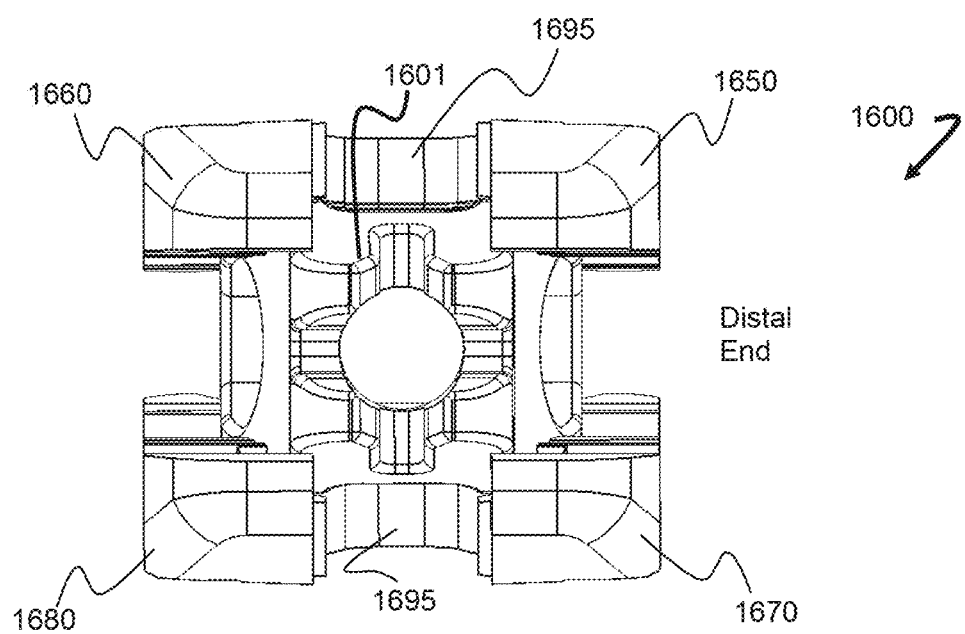
Figure 17A:
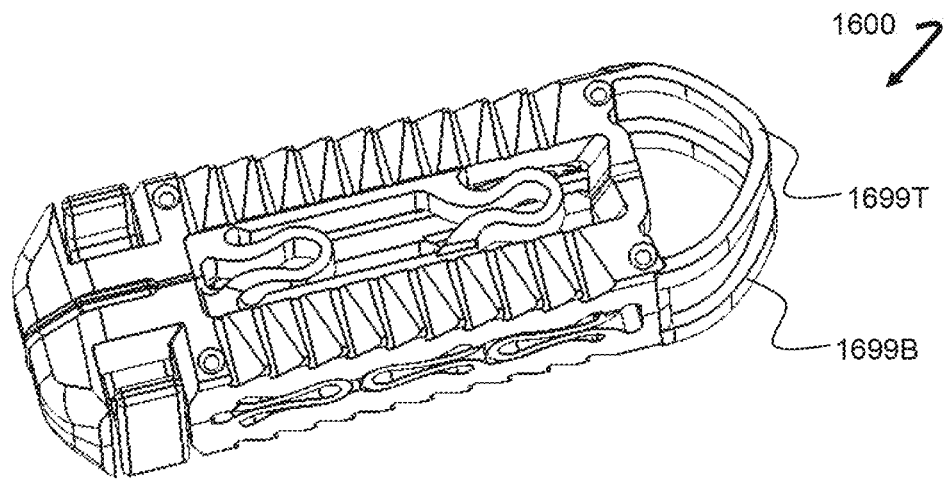
FIGS. 17A and 17B illustrate the cage of FIGS. 16A-16J in a collapsed configuration, according to some embodiments.
Figure 17B:
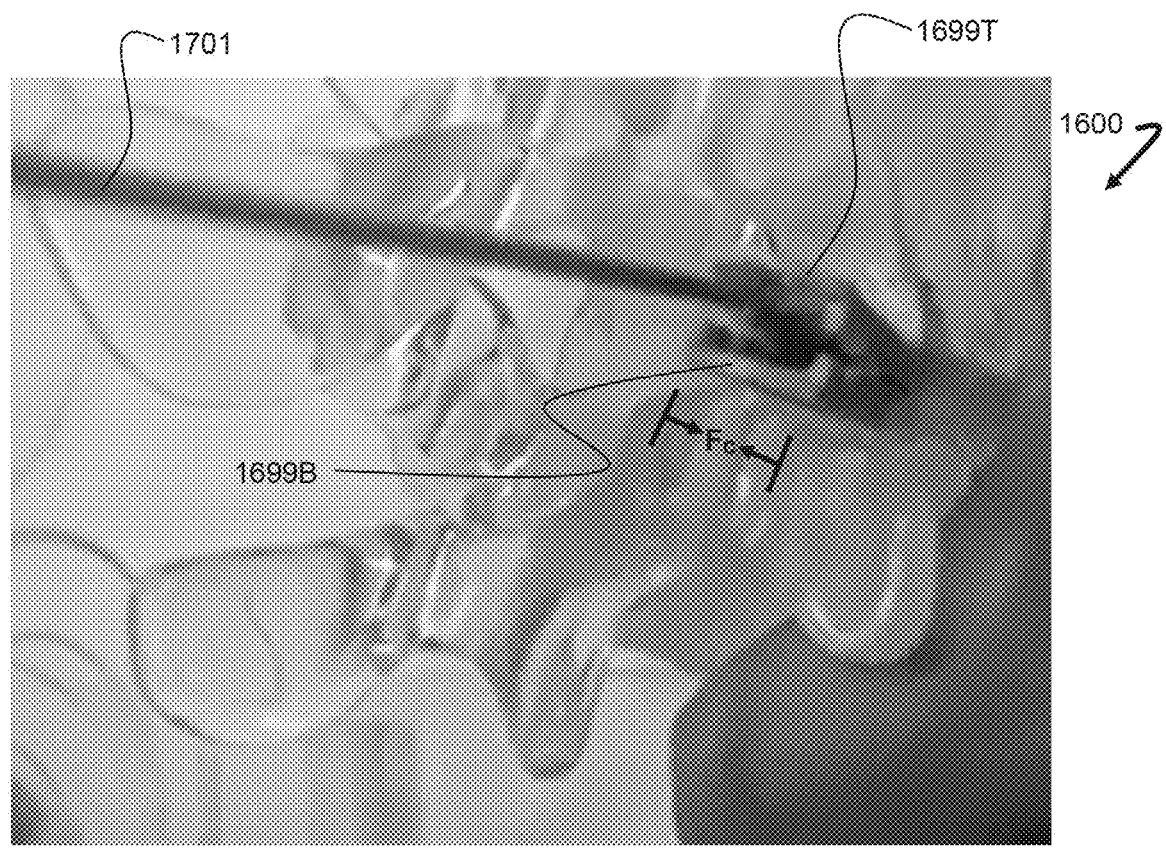

FIGS. 17A and 17B illustrate the cage of FIGS. 16A-16J in a collapsed configuration, according to some embodiments. FIG. 17A shows, for example, a perspective view of the top and bottom tension straps 1699T,1699B flexed due to the cage 1600 being in the collapsed configuration. FIG. 17B shows how a flexed tensioner 1699T can be used, for example, in the process of removing the cage 1600 from a subject. As can be seen from FIG. 17B, the steps of attaching a puller 1701 to the tensioner 1699T and pulling on the tension 1699T creates a collapsing force, $F_C$, on the cage 1600 which helps to remove the cage from the intervertebral space of the subject.

In some embodiments, the tensioner is inelastic, or at least substantially inelastic. In some embodiments, the tension force can be increased by increasing the cross-sectional area of the tensioner and decreased by decreasing the cross-sectional area of the tensioner. In some embodiments, the tension force can comprise a force applied by a shape-memory of the material. As such, in some embodiments, the tension force can be configured by varying cross-sectional area and shape of a material. In some embodiments, the tensioner can be entirely elastic beyond the stress and strain applied in the expansion of the cage. In some embodiments, the tensioner should have a tensile strength that is greater than the tensile strength required in the expansion of the cage and, in some embodiments, the tensile strength is at least about 1.5×, 2×, 2.5×, 3×, 3.5×, 4×, 4.5×, 5×, or any amount therein in increments of 0.1×, the tensile strength required to expand the cage. The tensile strength might be measured in some embodiments, for example, at the point immediately prior to the yield point of the tensioner material, taken as the lowest stress at which permanent deformation is measured in the tensioner. One of skill will appreciate that either ASTM D638 and ISO 527 tests, for example, might be used in making the material selection. One of skill, for example, will note that PEEK is a thermoplastic having desirable mechanical properties that include a Young's modulus of elasticity of about 3.6 GPa and a tensile strength of about 170 MPa. Polysulfone has a Young's modulus of elasticity of about 2.61 GPa and a tensile strength of about 68 MPa, and ULTEM 1000 has a Young's modulus of elasticity of about 3.45 GPa and a tensile strength of about 114 MPa.

In some embodiments, the Young's modulus of elasticity ranges of the tensioner from about 1.5 GPa to about 4.5 GPa, from about 2.0 GPa to about 4.0 GPa, from about 2.4 GPa to about 3.8 GPa, from about 2.6 GPa to about 3.6 GPa, or any range therein. In some embodiments, the Young's modulus of elasticity is about 2.0 GPa, about 2.2 GPa, about 2.4 GPa, about 2.6 GPa, about 2.8 GPa, about 3.0 GPa, about 3.2 GPa, about 3.4 GPa, about 3.6 GPa, about 3.8 GPa, or any amount therein in increments of 0.1 GPa. In some embodiments, a tensioner strap is "at least substantially inelastic" when it has a Young's modulus of elasticity that is greater than about 2.0 GPa, greater than about 2.2 GPa, greater than about 2.4 GPa, greater than about 2.6 GPa, greater than about 2.8 GPa, greater than about 3.0 GPa, greater than about 3.2 GPa, greater than about 3.4 GPa, greater than about 3.6 GPa, greater than about 3.8 GPa, or any amount therein in increments of 0.1 GPa. As such, if a tensioner has a Young's modulus of elasticity range with a lower end that is at least about 2.0 GPa, about 2.2 GPa, 2.4 GPa, 2.6 GPa, 2.8 GPa, 3.0 GPa, 3.2 GPa, 3.4 GPa, 3.6 GPa, or 3.8 GPa the tensioner can be consider to be at least substantially inelastic.

In some embodiments, the tensile strength ranges of the tensioner from about 30 MPa to about 300 MPa, from about 40 MPa to about 250 MPa, from about 50 MPa to about 200 MPa, from about 60 MPa to about 190 MPa, from about 70 MPa to about 180 MPa, from about 80 MPa to about 170 MPa, from about 65 MPa to about 185 MPa, or any range therein. In some embodiments, the tensile strength is about 60 MPa, about 70 MPa, about 80 MPa, about 90 MPa, about 100 MPa, about 110 MPa, about 120 MPa, about 130 MPa, about 140 MPa, about 150 MPa, about 160 MPa, about 170 MPa, about 180 MPa, about 190 MPa, about 200 MPa, about 210 MPa, about 220 MPa, about 230 MPa, about 240 MPa, about 250 MPa, or any amount or range therein in increments of 1.0 MPa.

FIG. 16D illustrates, for example, an embodiment wherein the proximal end of the cage 1600 has a top tension strap 1699T operably connecting the first top beam 1650 to the second top beam 1660, and a bottom tension strap 1699B operably connecting the first bottom beam 1660 to the second top beam 1680. FIG. 16E illustrates, for example, the distal end of the cage 1600, in the expanded configuration. As shown in at least FIGS. 14D and 15D, the distal end of the cage 1600 can be configured for receiving a stabilizer in operable contact with the beams 1650,1660,1670,1680.

FIG. 16F illustrates a top view of a system with the central beam 1601 inserted in the cage 1600 in the expanded configuration, and FIGS. 16G-16I have the cut-out views that remove the side struts to show the relationship between the central beam 1601, and the cage 1600 in the expanded configuration. No stabilizer is shown in these views, but the cage 1600 has a configuration for receiving an H-type stabilizer in combination with a top tension strap 1699T and a bottom tension strap 1699B as shown, for example, in FIGS. 16D, 16G, and 16H.

In some embodiments, the stabilizer can be on, at, or near the proximal end of the cage. In some embodiments, the stabilizer can be on, at, or near the distal end of the cage. In some embodiments, the stabilizer can be on, at, or near the proximal end of the cage and in combination with a second stabilizer on, at, or near the distal end of the cage.

In some embodiments, the tensioner can be on, at, or near the proximal end of the cage and operably attaching the first top beam to the second top beam. In some embodiments, the tensioner can be on, at, or near the proximal end of the cage and operably attaching the first bottom beam to the second bottom beam. In some embodiments, the tensioner can be on, at, or near the distal end of the cage and operably attaching the first top beam to the second top beam. In some embodiments, the tensioner can be on, at, or near the distal end of the cage and operably attaching the first bottom beam to the second bottom beam. In some embodiments, the tensioner can be on, at, or near the proximal end of the cage and in combination with a second tensioner on, at, or near the distal end of the cage and operably attaching the first top beam to the second top beam. In some embodiments, the tensioner can be on, at, or near the proximal end of the cage and in combination with a second tensioner on, at, or near the distal end of the cage and operably attaching the first bottom beam to the second bottom beam. In any of the embodiments, whether used on, at, or neat the proximal end or on, at, or near the distal end, or both ends, a top tensioner can be used to attach the first top beam to the second top beam, and a bottom tensioner can be used to attach the first bottom beam to the second bottom beam. And, in some embodiments, the tensioner can be a single unit that attaches the first top beam to the second top beam, and it also the first bottom beam to the second bottom beam. Moreover, the tensioner, whether used as one strap or a plurality of straps, can be formed as monolithically integral with the cage.

In some embodiments, a tensioner can be used in combination with a stabilizer. In these embodiments, the stabilizer can be on, at, or near the distal end of the cage, and the tensioner can be on, at, or near the proximal end of the cage. Likewise, in these embodiments, the stabilizer can be on, at, or near the proximal end of the cage, and the tensioner can be on, at, or near the distal end of the cage. In some embodiments, the stabilizer is on, at, or near the distal end of the cage, and it is used in combination with a top tensioner that operably connects the first top beam to the second top beam and a bottom tensioner that operably connects the first bottom beam to the second bottom beam.

In some embodiments, a cage can have a tensioner at the proximal end of the cage and at the distal end of the cage. In some embodiments, a cage can have proximal top tensioner at the proximal end of the cage connecting the first top beam to the second top beam, a proximal bottom tensioner at the proximal end of the cage connecting the first bottom beam to the second bottom beam, a distal top tensioner at the distal end of the cage connecting the first top beam to the second top beam, and a distal bottom tensioner at the distal end of the cage connecting the first bottom beam to the second bottom beam.

Figure 18A:
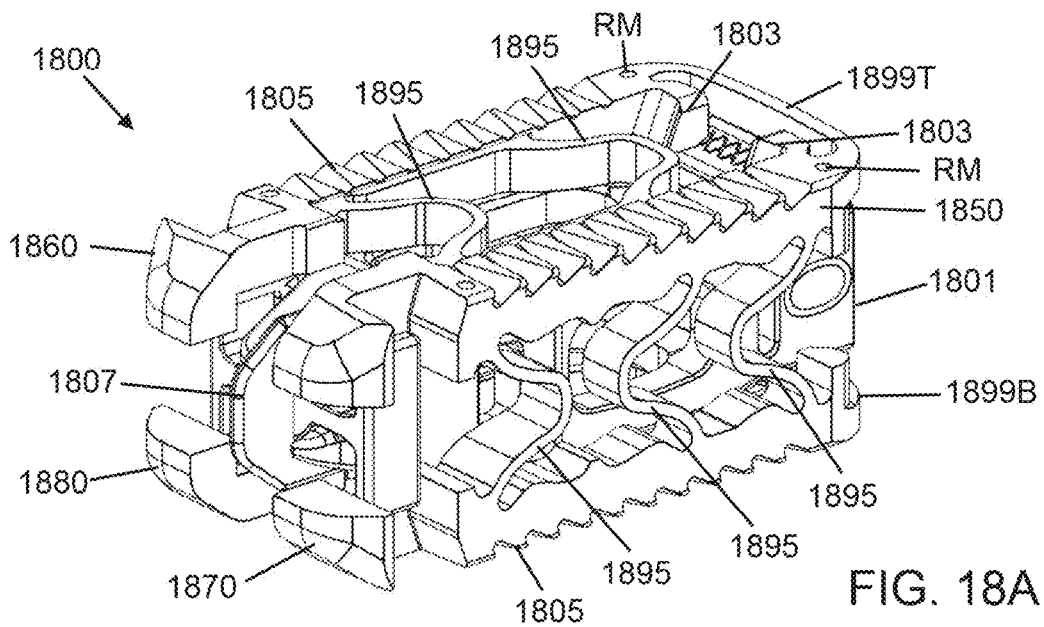
FIGS. 18A-18I illustrate components of a system having a cage with a tensioner, a central beam or shim having a vertical split configured for expanding the cage, and a locking stabilizer, according to some embodiments.
Figure 18B:
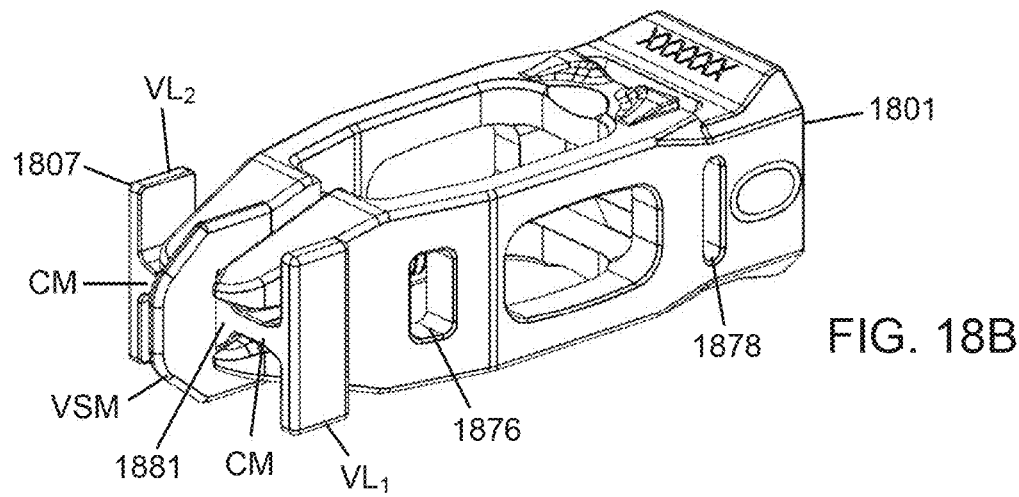
Figure 18C:
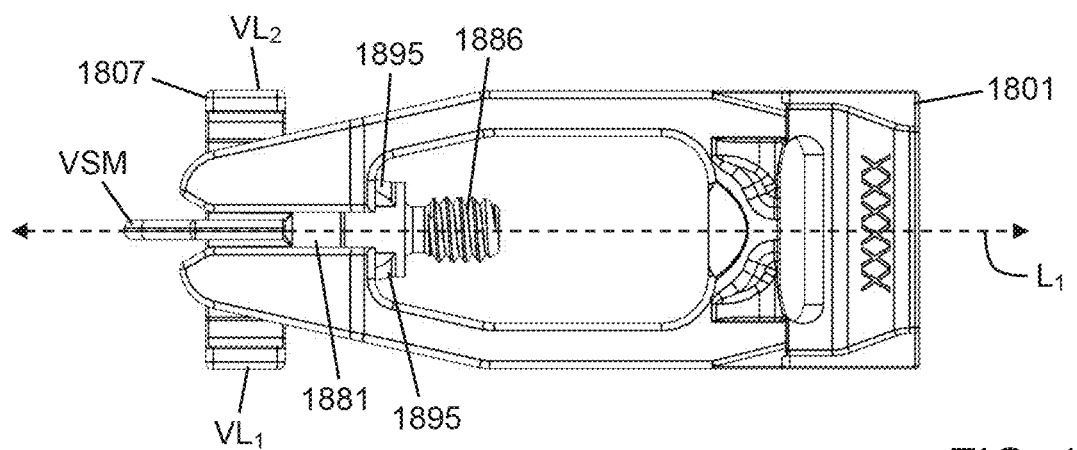
Figure 18D:
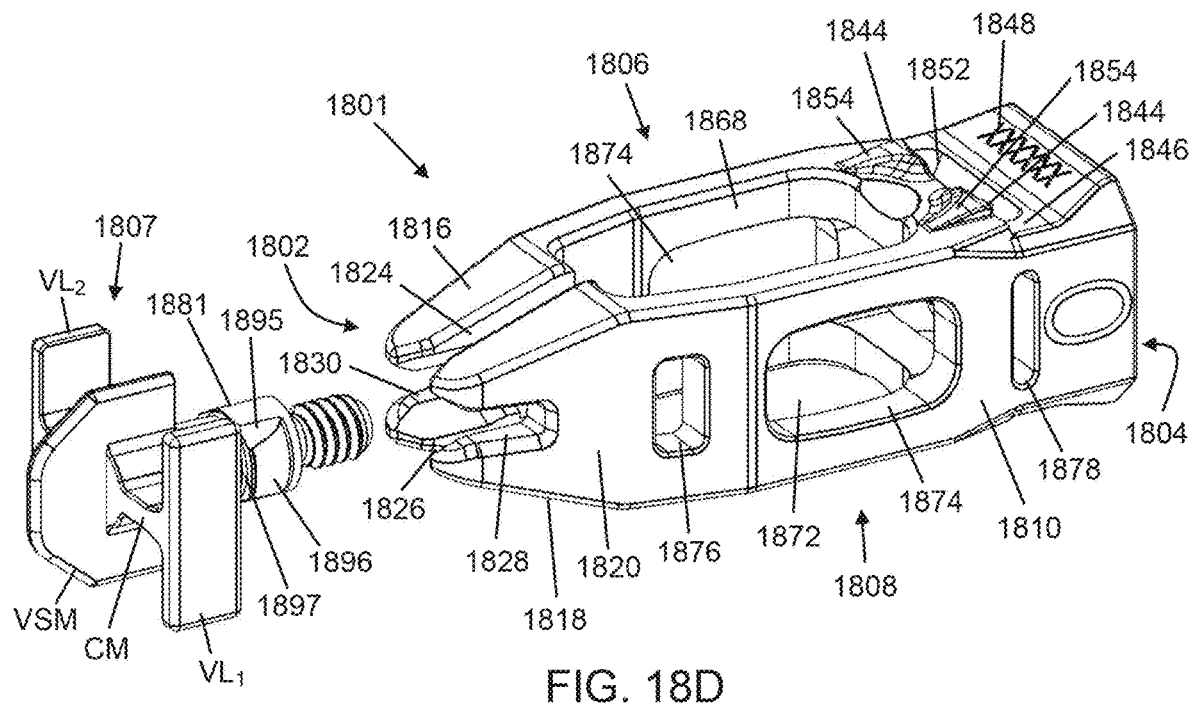
Figure 18E:
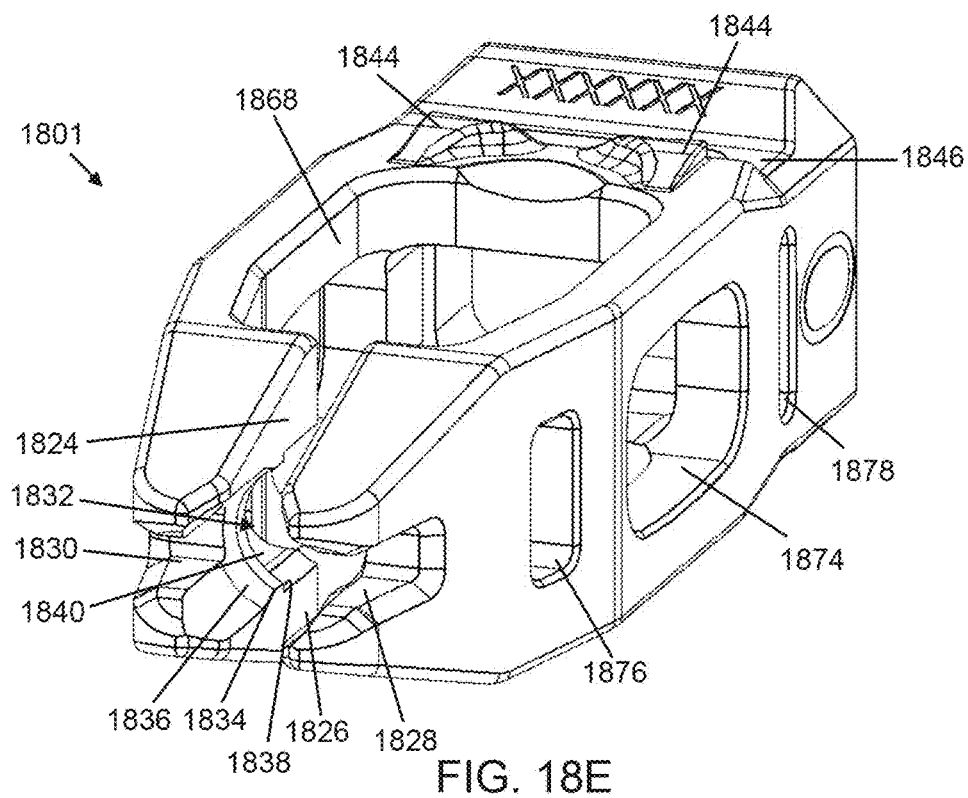
Figure 18F:
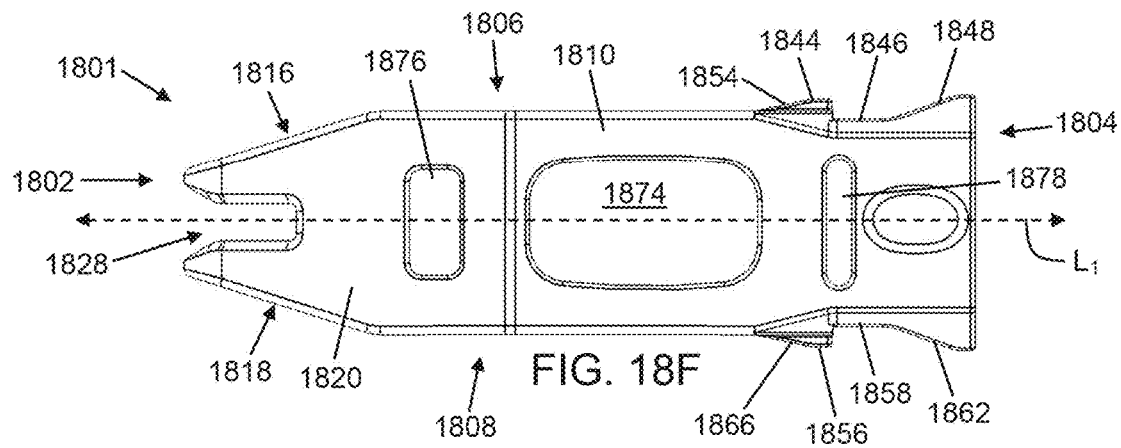
Figure 18G:
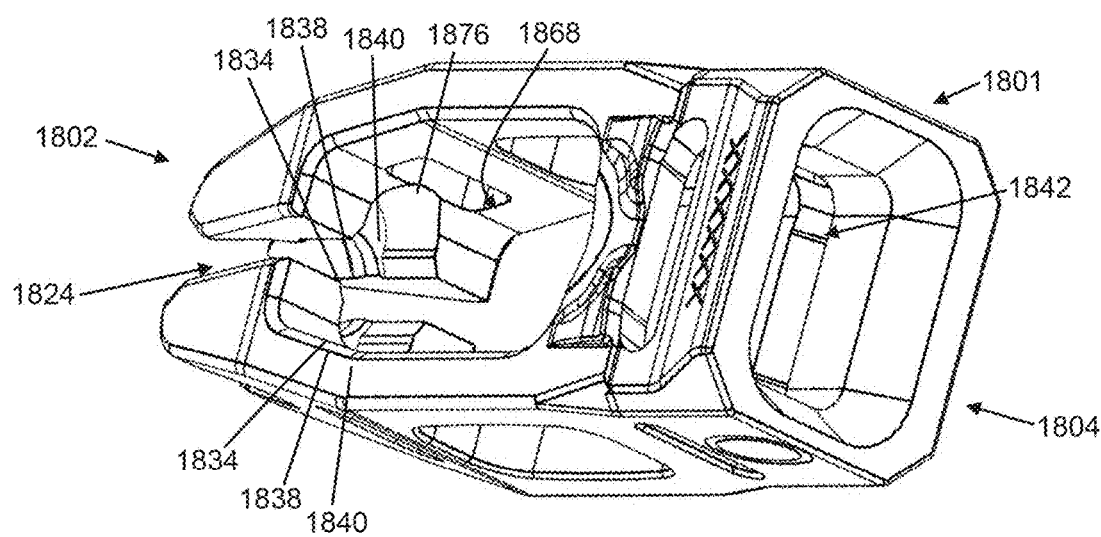
Figures 18H, 18I:
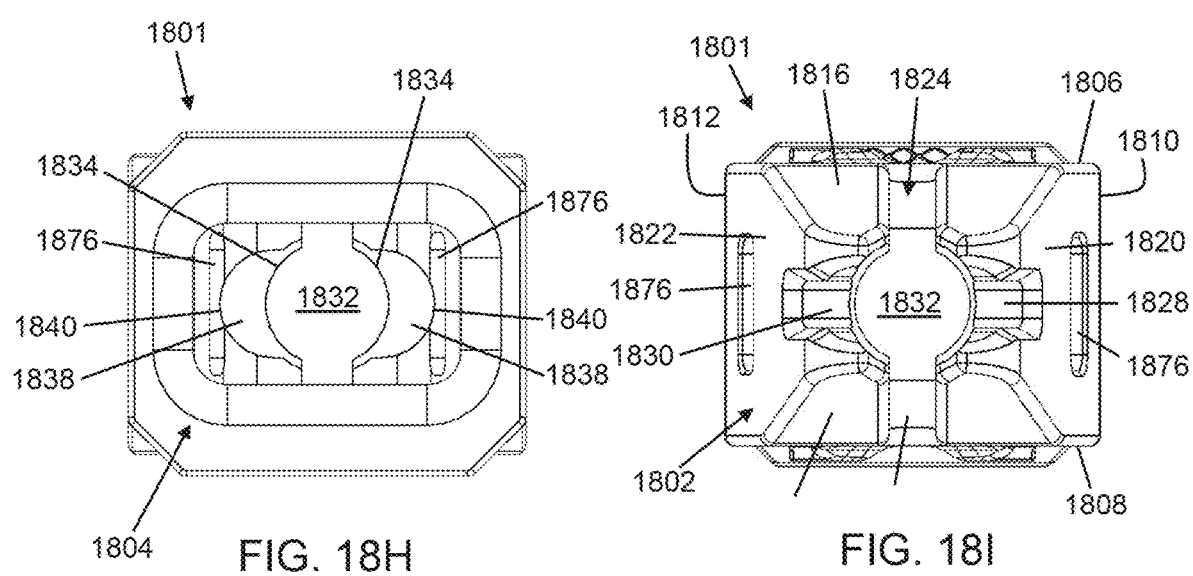
Figure 19A:
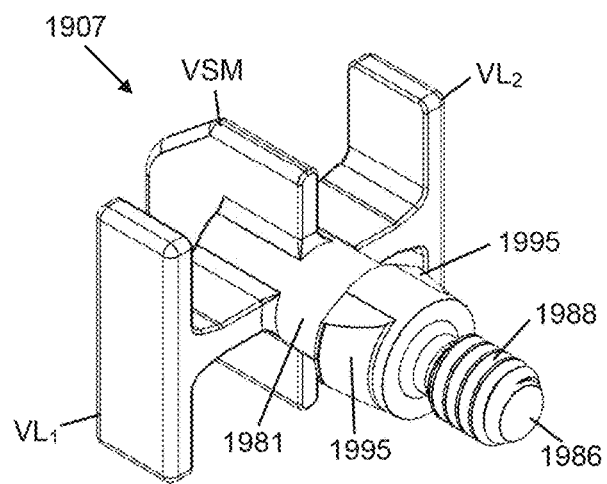
FIGS. 19A-19F illustrate an example of the locking stabilizer, wherein the stabilizer is in an H-configuration, according to some embodiments.
Figure 19B:
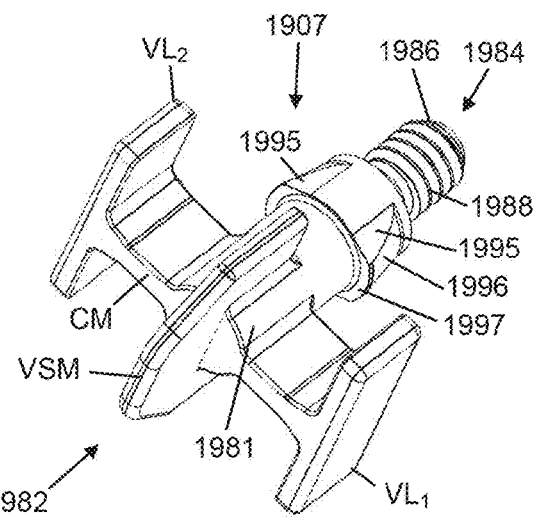
Figure 19C:
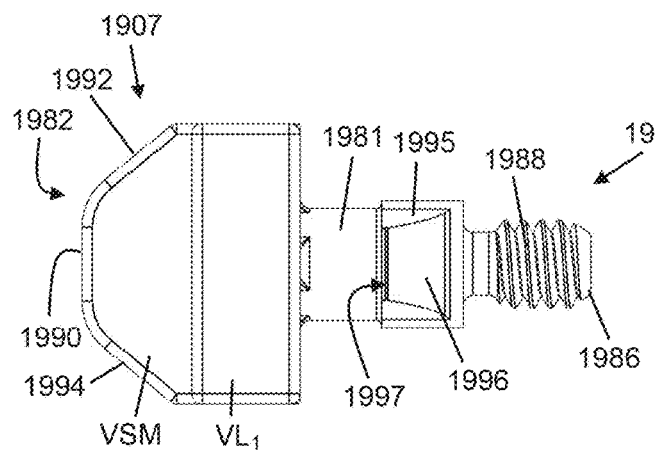
Figure 19D:
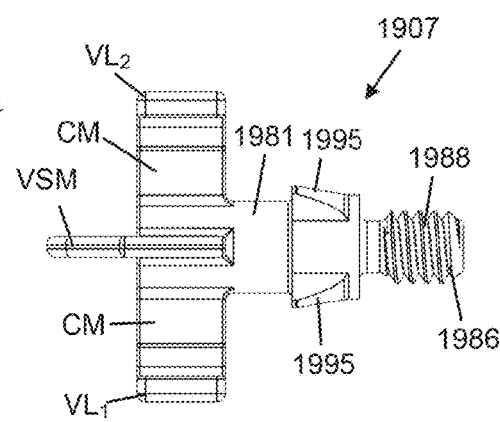
Figure 19E:
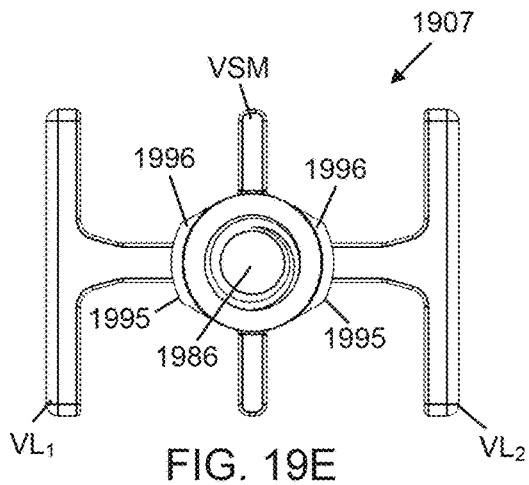
Figure 19F:
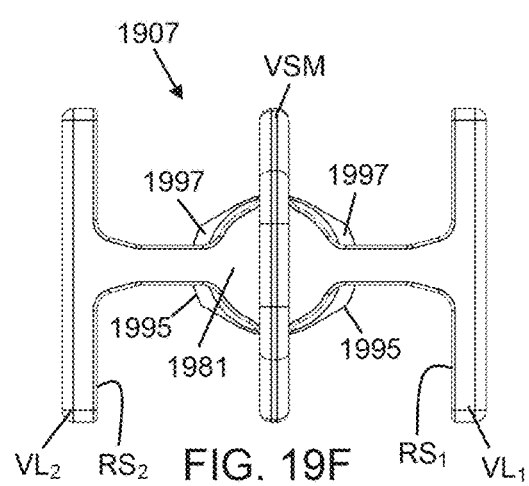

FIGS. 18A-18I illustrate components of a system having a cage 1800 with a tensioner, a central beam or shim 1801 having a vertical split configured for expanding the cage, and a locking stabilizer 1807, according to some embodiments. FIG. 18A shows the cage without a central beam to illustrate features of a cage, FIGS. 18B-18D show the central beam with a locking stabilizer, and FIGS. 18E-18I show the central beam without the cage or locking stabilizer to illustrate the features of the central beam. The locking stabilizer can have any configuration that performs the functions set-forth herein for such a stabilizer. For example, the stabilizer can have an X-configuration or an H-configuration in these embodiments, at least as set-forth herein in at least FIGS. 14A-14D and FIGS. 15A-15D discussed above. FIG. 18A provides a perspective view of a cage 1800 that may be used in such a system, the cage 1800 having a first top beam 1850, a first bottom beam 1870, a second top beam 1860, and a second bottom beam 1880, the beams interconnected by flexible struts 1895 that allow for bilateral expansion and collapse of the cage 1800. In some embodiments, the cage 1800 can include one or more tensioners such as, for example, tension straps 1899T, 1899B. Moreover, the beams 1850, 1860, 1870, 1880 can have cleats 1805 to help avoid backout of the cage 1800 from the intervertebral space. The cage may be any cage described above, particularly for example the cage 1600 of FIGS. 16A-16I. It should be understood that any feature described above with respect to any cage may be included on cage 1800, and thus further description of cage 1800 would be repetitive.

FIGS. 18B-18L illustrate one example of a central beam, or shim 1801 in further detail. The shim 1801 drives the expansion of the cage 1800 and provides stability for the expanded cage 1800 after insertion. The degree of cage expansion in any direction is directly correlated to the size and shape of the shim 1801. Therefore, the shim may be provided in various sizes and shapes without departing from the scope of the disclosure. By way of example, the shim 1801 includes a leading end 1802, trailing end 1804, top 1806, bottom 1808, a first side 1810, a second side 1812, and a central lumen 1814.

The shim 1801 has a generally tapered leading end 1802 such that advancement of the shim 1801 into the cage 1800 causes expansion of the cage 1800. In some embodiments, the shim 1801 is tapered to cause expansion of the cage 1800 in one direction only. In some embodiments, the shim 1801 is tapered to cause expansion of the cage 1800 in multiple directions. To facilitate this, each of the top 1806, bottom 1808, first side 1810, and second side 1812 includes a tapered surface 1816, 1818, 1820, 1822, respectively, that tapers distally toward the central longitudinal axis $L_1$ of the system. The slope of each individual tapered surface determines how quickly the cage 1800 expands to maximum height/width, and may be different for the different surfaces. By way of example, the angle of the taper for the tapered surfaces 1816, 1818, 1820, 1822 can range from about 0° to about 45°, and from about 5° to about 35°. In some embodiments, the angle of the taper for the top and bottom tapered surfaces 1816, 1818 can range from about 25° to about 35°. In some embodiments, the angle of the taper for the side tapered surfaces 1820, 1822 is 25°. In some embodiments, the angle of the taper for each tapered surface 1816, 1818, 1820, 1822 is 25°. Each tapered surface 1816, 1818, 1820, 1822 has a slot 1824, 1826, 1828, 1830 formed therein that is configured to receive a portion of the locking stabilizer 1807 during coupling of the shim 1801 and cage 1800. More specifically, the tapered surface 1816 has a vertically-oriented slot 1824 configured to receive a first portion of the vertical support member VSM, the tapered surface 1818 has a vertically-oriented slot 1826 configured to receive a second portion of the vertical support member VSM, the tapered surface 1820 has a horizontally oriented slot 1828 configured to receive a first portion of the cross-member CM, and the tapered surface 1822 has a horizontally-oriented slot 1830 configured to receive a second portion of the cross-member CM. In some embodiments, the vertically-oriented slots 1824, 1826 extend completely through the leading end 1802 of the shim 1801. This allows flexibility of the system in the medial/lateral (horizontal) direction only. The horizontally oriented slots 1828, 1830 extend partially through the leading end 1802.

Figure 20A:
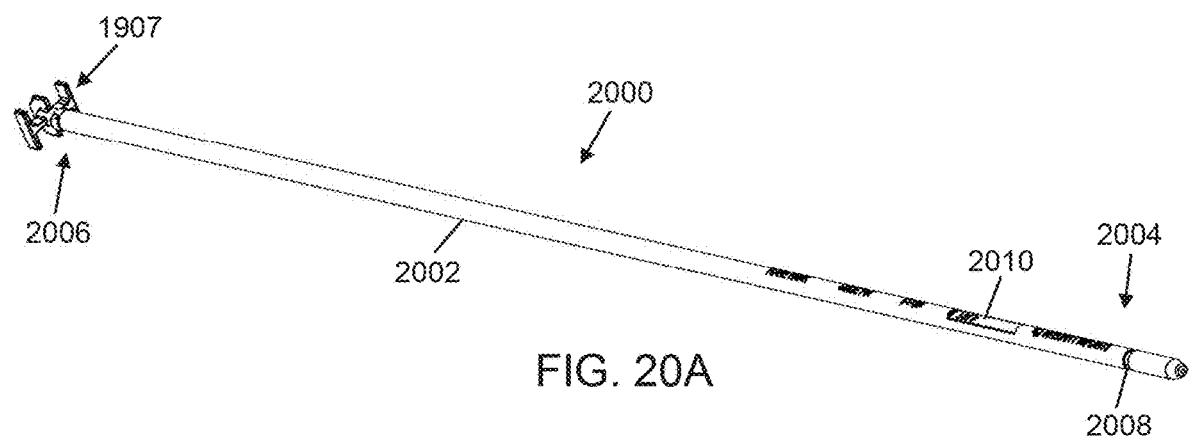
FIGS. 20A-20C illustrate an example of a guide pin coupled with the locking stabilizer of FIGS. 19A-19F, according to some embodiments.
Figure 20B:
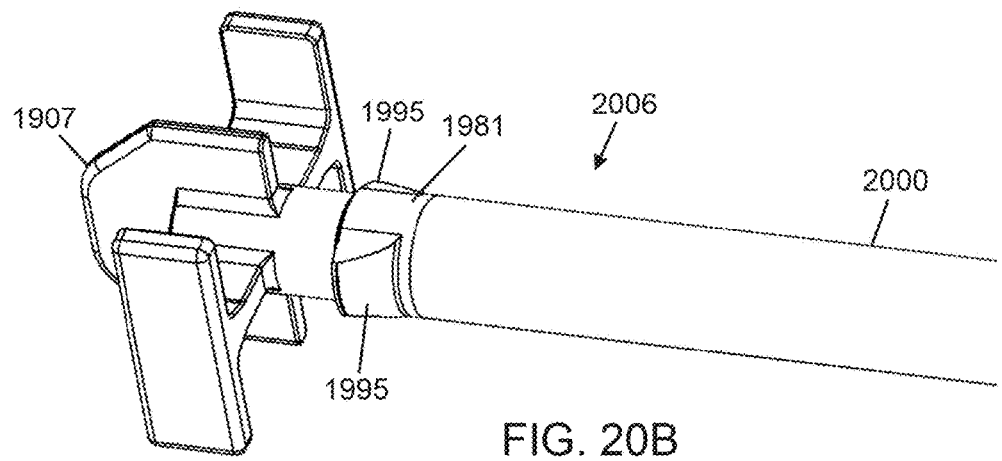
Figure 20C:
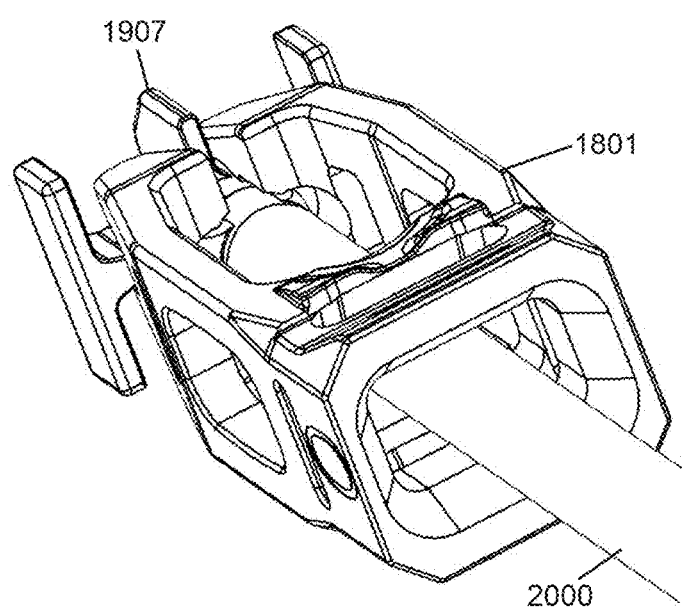

The leading end 1802 includes an aperture 1832 sized and configured to enable passage of the base 1880 of the locking stabilizer 1807 through the leading end 1802 and into the cage 1800 so that the post 1886 is accessible for coupling with an guide pin (for example guide pin 2000 of FIGS. 20A-20C). The shim 1801 has a shoulder 1834 on the internal diameter of the aperture 1832. The shoulder 1834 has a distally tapered leading surface 1836 and a squared-off or perpendicular trailing surface 1838. The tapered leading surface 1836 facilitates loading of the shim 1801 onto the guide pin 2000 and also sliding along the guide pin. The distally tapered leading surface 1836 interacts with the proximally tapered trailing surface 1896 of the locking barb 1895 on the locking stabilizer 1807 to act as a ramp to facilitate passage of the shoulder 1834 over the locking barb 1895. Once the shoulder 1834 has passed beyond the tapered trailing surface 1896 of the locking barb 1895, the perpendicular trailing surface 1838 interacts with the perpendicular leading surface 1897 of the locking barb 1895 to provide a physical barrier preventing backout of the shim 1801, essentially locking the shim 1801 to the stabilizer 1807. The length and angle of the taper directly correlates to the insertion force required. An oval shaped recess 1840 is provided on the interior of the shim 1801 proximal of the shoulder 1834. The oval shaped recess 1840 is sized and configured to accommodate the locking barbs 1895 on the locking stabilizer 1807 during insertion.

The trailing end 1804 includes an axial aperture 1842 sized and configured to allow passage of one or more instruments (e.g. guide pin, inserter, graft applicator, etc) through the trailing end 1804 and into the central lumen 1814. The top surface 1806 at the trailing end 1804 includes one or more locking barbs 1844, a transverse recess 1846 positioned posterior of the one or more locking barbs 1844, a posterior ramp 1848 positioned posterior of the transverse recess 1846, and an engagement aperture 1852 formed within the recess 1846 for engaging with a surgical instrument such as a shim removal tool. Each locking barb 1844 includes a ramped surface 1854 ascending posteriorly to the edge of the recess 1846. The one or more locking barbs 1844 and transverse recess 1846 interact with locking flanges 1803 on the cage 1800 to securely hold the shim 1801 within the cage 1800 after the shim 1801 has been fully inserted. More specifically, as the trailing end 1804 of the shim 1801 advances into the cage 1800, the first and second locking flanges 1803 will slideably engage the ramped surface(s) 1854 of the locking barb(s) 1844 and be displaced slightly as the locking barb(s) 1844 pass by, at which point the locking flanges 1803 will snap back into place within the transverse recess 1846. This action not only produces an audible and tactile "click", but also places the locking flanges 1803 in position to prevent unwanted posterior migration of the shim 1801 after the surgery has been completed.

The bottom surface 1808 at the trailing end 1804 is essentially a mirror image of the top surface 1806 at the trailing end 1804, and includes one or more locking barbs 1856, a transverse recess 1858 positioned posterior of the one or more locking barbs 1856, a posterior ramp 1862 positioned posterior of the transverse recess 1858, and an engagement aperture 1864 formed within the recess 1862 for engaging with a surgical instrument such as a shim removal tool. Each locking barb 1856 includes a ramped surface 1858 ascending posteriorly to the edge of the recess 1858. The one or more locking barbs 1856 and transverse recess 1858 interact with corresponding locking flanges (not shown) of the cage 1800 to securely hold the shim 1801 within the cage 1800 after the shim 1801 has been fully inserted. More specifically, as the trailing end 1804 of the shim 1801 passes into the cage 1800, the locking flanges will slideably engage the ramped surface(s) 1866 of the locking barb(s) 1856 and be displaced slightly as the locking barb(s) 1856 pass by, at which point the locking flanges will snap back into place within the transverse recess 1858. This action not only produces an audible and tactile "click", but also places the locking flanges in position to prevent unwanted posterior migration of the shim 1801 after the surgery has been completed.

The surgeon may confirm that the shim 1801 has been fully inserted by viewing the construct under fluoroscopy and ensuring that the locking barbs 1844 and/or locking barbs 1856 are anterior of the two radiographic markers RM positioned at the trailing end of the cage 1800. In some embodiments, the shim 1801 includes locking verification slots 1878 to further aid the surgeon in obtaining visual confirmation that the locking barbs 1844 and/or locking barbs 1856 are properly positioned relative to the locking flanges of the cage 1800. By way of example, the locking verification slots 1878 may comprise vertically-oriented elongated slots formed in the first and second sides 1810, 1812 in alignment with the transverse recesses 1846, 1858. Thus, when the shim 1801 is fully inserted into the cage 1800, the radiographic markers RM should be in positioned above/below or posterior of the locking verification slots 1878. The use of locking verification slots 1878 is advantageous in that the slots (e.g. gaps in material) are easier to identify under fluoroscopy than the locking barbs 1844, 1856.

The first and second sides 1810, 1812 are smooth at the trailing end 1804. The shim 1801 further includes large top and bottom graft windows 1868, 1872 formed in the top and bottom surfaces 1806, 1808, respectively, and side graft windows 1874 formed in the first and second sides 1810, 1812. The graft windows allow for the use of bone graft material (e.g. biologic bone, artificial bone matrix, collagen, protein, etc.).

FIGS. 19A-19F illustrate an example of the locking stabilizer 1907, wherein the stabilizer is in an H-configuration, according to some embodiments. By way of example, the locking stabilizer 1907 according to the present example may be made from any suitable medical grade material, including but not limited to metal alloys (e.g. cobalt chromium), titanium alloys (e.g. Ti6Al4V, nickel titanium), or polymers (e.g. PEEK, polyetherimide (Ultem), polyimide, polyamide). The locking stabilizer 1907 of the instant example includes a base 1981, a leading side 1982, and a trailing side 1984. The base 1981 includes a post 1986 extending perpendicularly from the trailing side, the post 1986 being configured to engage an insertion instrument such as a guide pin. By way of example, the post 1986 includes threads 1988 for threaded engagement with the insertion instrument, however other engagement mechanisms are possible, for example snap-fit, ratchet, and the like.

The base 1981 further includes a pair of locking barbs 1995 positioned between the post 1886 and the vertical support member VSM, the locking barbs 1995 configured to interact with the shoulder 1834 of the shim 1801 to effectively lock the locking stabilizer 1807 and shim 1801 together. By way of example, the locking barbs 1995 each have a proximally tapered trailing surface 1996 and a perpendicular leading surface 1997. The proximally tapered trailing surface 1996 interacts with the distally tapered leading surface 1836 of the shoulder 1834 to act as a ramp to facilitate passage of the shoulder 1834 over the locking barb 1995. Once the shoulder 1834 has passed beyond the tapered trailing surface 1996 of the locking barb 1995, the perpendicular leading surface 1997 interacts with the perpendicular trailing surface 1838 of the shoulder 1834 to provide a physical barrier preventing backout of the shim 1801, essentially locking the shim 1801 to the stabilizer 1907. The minor diameter of the tapered trailing surface 1996 is at the same diameter as the guide pin 2000 (FIGS. 20A-20C), which ensures there is no step in the transition from the guide pin 2000 to the stabilizer 1907. The major diameter of the tapered trailing surface 1996 correlates to the amount of interference and engagement between the stabilizer 1907 and the shim 1801 in that increasing the major diameter increases the force required to remove the shim 1801. The length and angle of the taper directly correlates to the insertion force required.

The H-configuration can have a first vertical leg $VL_1$, a second vertical leg $VL_2$, and a cross-member CM that connects the first and second vertical legs $VL_1$ $VL_2$, to the base 1981. The first vertical leg $VL_1$ includes a first retaining surface $RS_1$ for engaging with the first top beam 1850 and the first bottom beam 1870. The second vertical leg $VL_2$ includes a second retaining surface $RS_2$ for engaging with the second top beam 1860 and the second bottom beam 1880. The cross-member CM provides a tensile force for resisting the first top beam 1850, the first bottom beam 1870, the second top beam 1860, and the second bottom beam 1880 from the lateral movement that exceeds the expanded state. In some embodiments, the shim 1801 has a pair of horizontal slots 1828, 1830 configured complementary to the cross-member CM of the stabilizer 1907, and the horizontal slots 1828, 1830 of the central beam 1801 slidably connects with the cross-member CM in the expanded state.

In some embodiments, the cross-member CM further comprises a vertical support member VSM and the shim 1801 has a pair of vertical slots 1824, 1826 configured complementary to the vertical support member VSM of the stabilizer, and the vertical slots 1824, 1826 of the shim 1801 slidably connect with the vertical support member VSM in the expanded state. The vertical support member VSM extends perpendicularly from the leading side 1882 of the base 1881 and has a height dimension that is substantially identical to the height dimension of the cage 1800 in a collapsed state, and at least a partial perimeter shape that coincides with the shape of the leading end of the cage 1800. More specifically, the vertical support member VSM has a leading edge 1990 including first and second tapered portions 1992, 1994 that align with the tapered portions of the smooth outer leading surfaces of the support beams 1850, 1860, 1870, 1880 so that when the system is in the initial, collapsed state, the leading end presents as a smooth, closed leading surface to facilitate advancement of the system into the target disc space.

The locking stabilizer 1907 is not attached to the cage 1800 but is held in place by different elements during different stages of the insertion process. For example, prior to insertion the locking stabilizer 1907 is held in place by the distal ends of the support beams 1850, 1860, 1870, 1880 of the collapsed implant. During insertion (and more specifically during shim 1801 insertion) the locking stabilizer 1907 is held in place due to its connection to the guide pin 2000 (see, e.g. FIGS. 20A-20C). Finally, after insertion the locking shim 1907 is held in place by the leading end 1802 of the shim 1801 (e.g. FIG. 18B) as well as the interaction between the locking barbs 1995 and the shoulder 1834 of the shim 1801.

FIGS. 20A-20C illustrate an example of a guide pin 2000 coupled with the locking stabilizer 1907 of FIGS. 19A-19F, according to some embodiments. FIG. 20C illustrates the coupled guide pin and locking stabilizer engaged with a shim 1801 of FIGS. 18A-18I, according to some embodiments. By way of example, the guide pin 2000 comprises a generally cylindrical elongated shaft 2002 having a proximal end 2004 and a distal end 2006. According to some embodiments, the proximal end 2004 has various features that facilitate interaction with other instruments, for example including but not limited to a circumferential groove 2008 and one or more generally planar recesses 2010. The distal end 2006 comprises an engagement aperture (not shown) configured to engage the post 1986 of the locking stabilizer 1907 described above. In some embodiments, the engagement aperture includes internal structure that facilitates secure engagement with the post 1986. For example, a guide pin 2000 configured for use with the example locking stabilizer 1907 described above may include internal threads to threadedly engage the threads 1988 on the post 1986. When the guide pin 2000 is fully engaged with the locking stabilizer 1907, the distal end 2006 is flush with the proximal end of the base 1981 of the locking stabilizer 1907. At the junction, the diameter of the base 1981 matches the diameter of the guide pin 2000 so as to enable seamless transition from the guide pin to the stabilizer as the shim 1801 is advanced distally along the guide pin to engage the stabilizer.

Figure 21A:
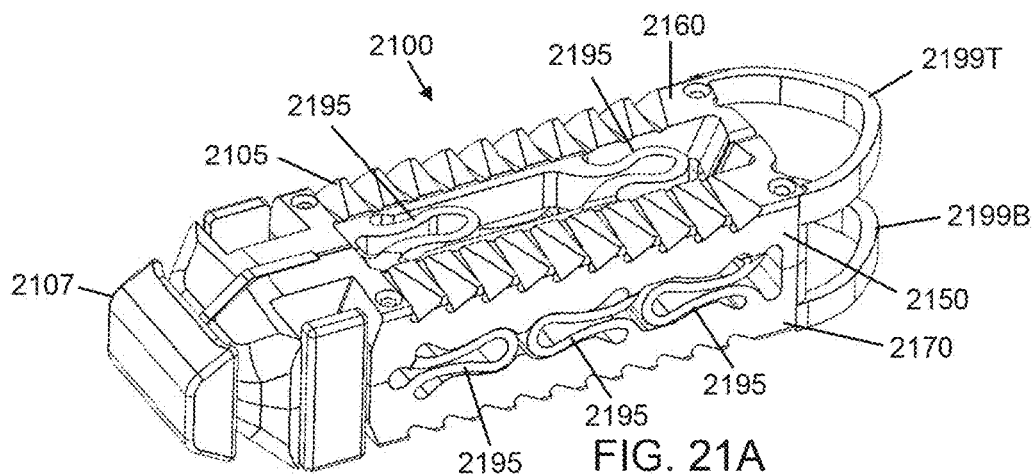
FIGS. 21A-21F illustrate components of a system having a cage with a combination of a fortified stabilizer and a tensioner, and a central beam configured for expanding the cage, according to some embodiments.
Figure 21B:
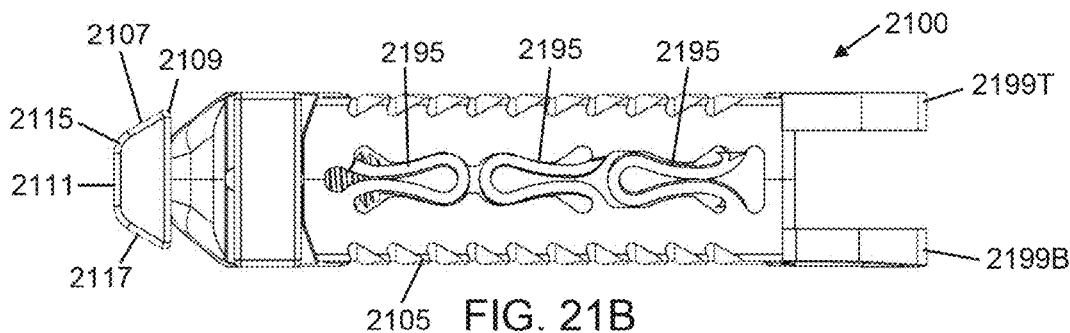
Figure 21C:
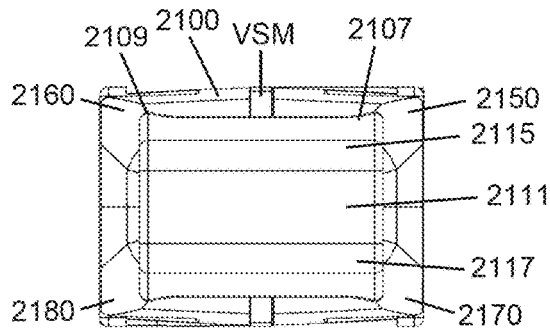
Figure 21D:
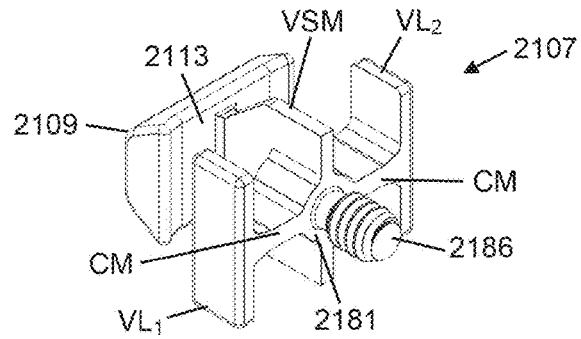
Figure 21E:
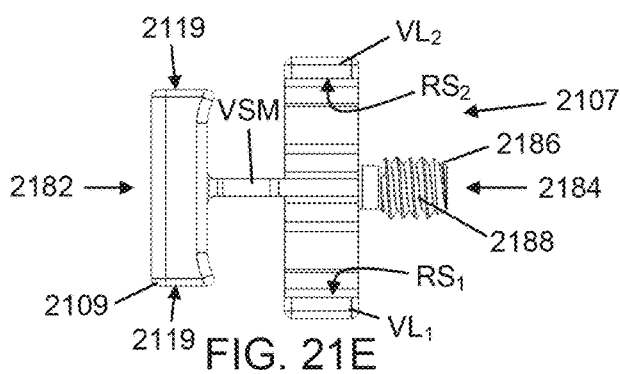
Figure 21F:
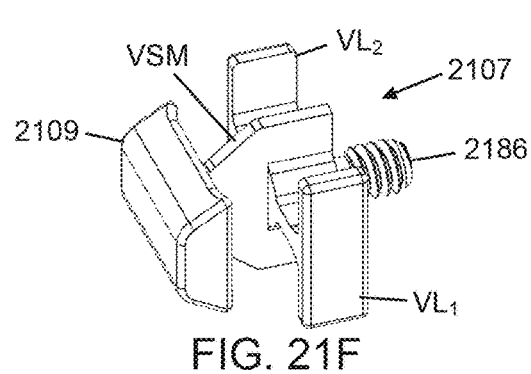

FIGS. 21A-21F illustrate components of a system having a cage 2100 with a tensioner, a central beam or shim configured for expanding the cage (not shown), and a fortified stabilizer 2107, according to some embodiments. FIGS. 21A-21C show the cage in a collapsed state without a central beam to illustrate features of a cage, and FIGS. 21D-21F show the fortified stabilizer. The fortified stabilizer can have any configuration that performs the functions set-forth herein for such a stabilizer. For example, the stabilizer can have an X-configuration or an H-configuration in these embodiments, at least as set-forth herein in at least FIGS. 14A-14D and FIGS. 15A-15D discussed above. FIG. 21A provides a perspective view of a cage 2100 that may be used in such a system, the cage 2100 having a first top beam 2150, a first bottom beam 2170, a second top beam 2160, and a second bottom beam 2180, the beams interconnected by flexible struts 2195 that allow for bilateral expansion and collapse of the cage 2100. In some embodiments, the cage 2100 can include one or more tensioners such as, for example, tension straps 2199T, 2199B. Moreover, the beams 2150, 2160, 2170, 2180 can have cleats 2105 to help avoid backout of the cage 2100 from the intervertebral space. The cage may be any cage described above, particularly for example the cage 1600 of FIGS. 16A-16I. It should be understood that any feature described above with respect to any cage may be included on cage 2100, and thus further description of cage 2100 would be repetitive.

By way of example, the fortified stabilizer 2107 described herein is in an H-configuration. The fortified stabilizer 2107 according to the present example may be made from any suitable medical grade material, including but not limited to metal alloys (e.g. cobalt chromium), titanium alloys (e.g. Ti6Al4V, nickel titanium), or polymers (e.g. PEEK, polyetherimide (ULTEM), polyimide, polyamide). The fortified stabilizer 2107 of the instant example includes a base 2181, a leading side 2182, and a trailing side 2184. The base 2181 includes a post 2186 extending perpendicularly from the trailing side 2184, the post 2186 being configured to engage an insertion instrument such as a guide pin 2000 described above. By way of example, the post 2186 includes threads 2188 for threaded engagement with the insertion instrument, however other engagement mechanisms are possible, for example snap-fit, ratchet, and the like. Although not shown in the instant example, it should be understood that the fortified stabilizer 2107 described herein may be provided with the locking feature of the locking stabilizer 1907 described above.

The H-configuration can have a first vertical leg $VL_1$, a second vertical leg $VL_2$, and a cross-member CM that connects the first and second vertical legs $VL_1$, $VL_2$, to the base 2181. The first vertical leg $VL_1$ includes a first retaining surface $RS_1$ for engaging with the first top beam 2150 and the first bottom beam 2170. The second vertical leg $VL_2$ includes a second retaining surface $RS_2$ for engaging with the second top beam 2160 and the second bottom beam 2180. The cross-member CM provides a tensile force for resisting the first top beam 2150, the first bottom beam 2170, the second top beam 2160, and the second bottom beam 2180 from the lateral movement that exceeds the expanded state. In some embodiments, the shim 1801 has a pair of horizontal slots 1828, 1830 configured complementary to the cross-member CM of the stabilizer 2107, and the horizontal slots 1828, 1830 of the shim 1801 slidably connects with the cross-member CM in the expanded state.

In some embodiments, the cross-member CM further comprises a vertical support member VSM and the shim 1801 has a pair of vertical slots 1824, 1826 configured complementary to the vertical support member VSM of the stabilizer, and the vertical slots 1824, 1826 of the shim 1801 slidably connect with the vertical support member VSM in the expanded state. The vertical support member VSM extends perpendicularly from the leading side 2182 of the base 2181 and has a height dimension that is substantially similar to the height dimension of the cage 2100 in a collapsed state.

In some embodiments, the stabilizer 2107 further includes a fortified leading element 2109 attached to the front face of the vertical support member VSM to provide a sturdy wedge-shaped bumper to reduce the force applied directly to the cage 2100 (e.g. by body tissue) during insertion. The fortified leading element 2109 comprises a leading surface 2111, a trailing surface 2113, a top surface 2115, a bottom surface 2117, and a pair of lateral surfaces 2119. Each of the aforementioned surfaces on the fortified leading element 2109 is smooth, and the edges are generally rounded to impart minimal trauma to the surrounding tissue. The fortified leading element 2109 has a thickness dimension measured as the distance between the leading surface 2111 and trailing surface 2113. By way of example the thickness dimension may be in a range of 0.1-5.0 mm. The fortified leading element 2109 has a leading height dimension $H_L$ measured as the distance between the top surface 2115 and bottom surface 2117 at the junction with the leading surface 2111 and a trailing height dimension $H_T$ measured as the distance between the top surface 2115 and bottom surface 2117 at the junction with the trailing surface 2113. By way of example, the trailing height dimension $H_T$ is greater than the leading height dimension $H_L$ such that each of the top and bottom surfaces 2115, 2117 has a distal taper. This distal taper creates the wedge effect to help displace body tissue during insertion.

Figure 22A:
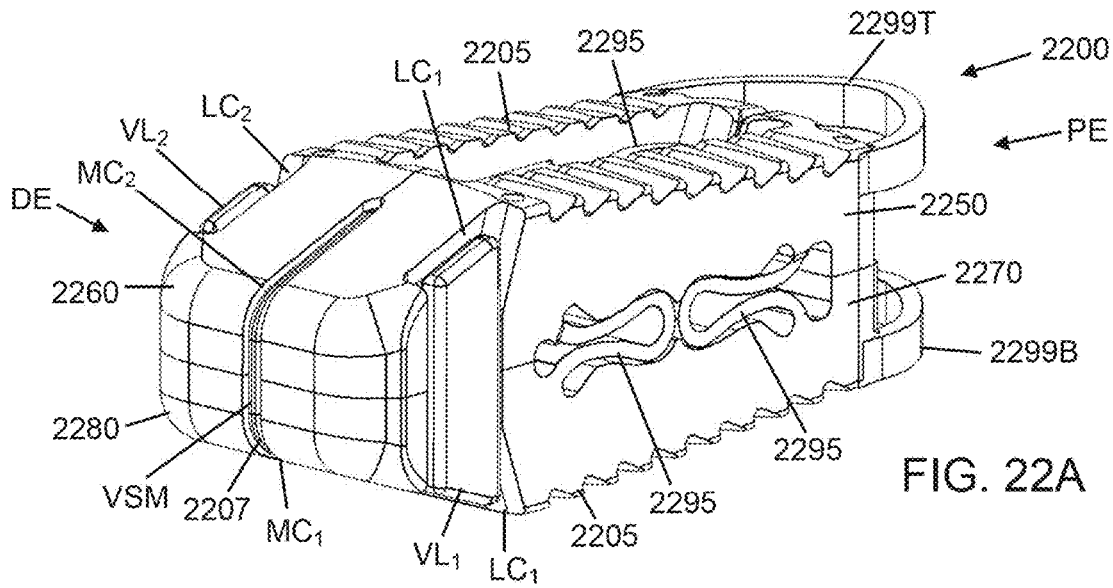
FIGS. 22A-22C illustrate components of a system having a cage with a combination of a stabilizer and a tensioner, and a central beam configured for expanding the cage, according to some embodiments.
Figure 22B:
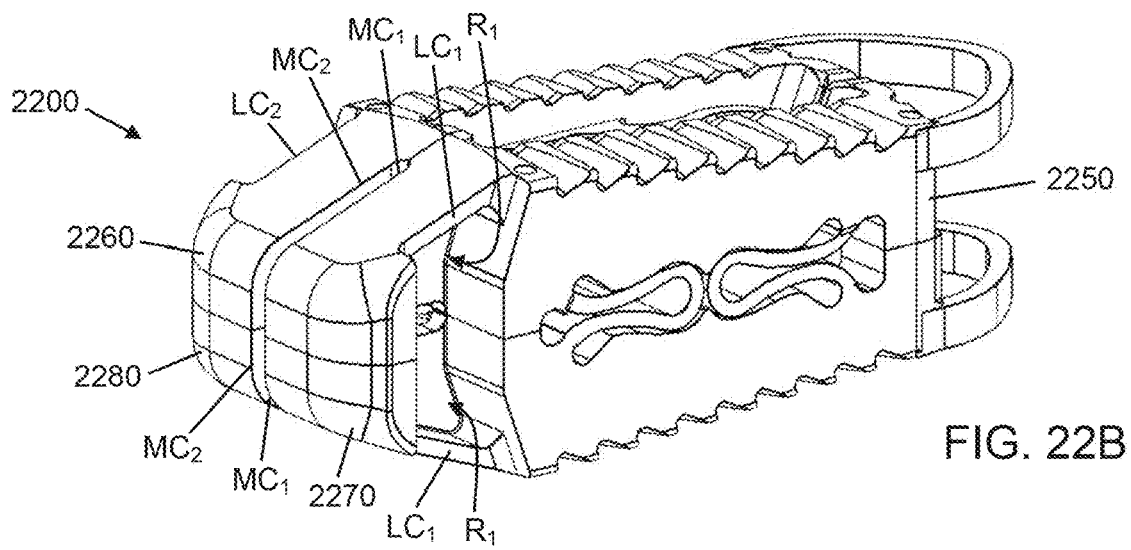
Figure 22C:
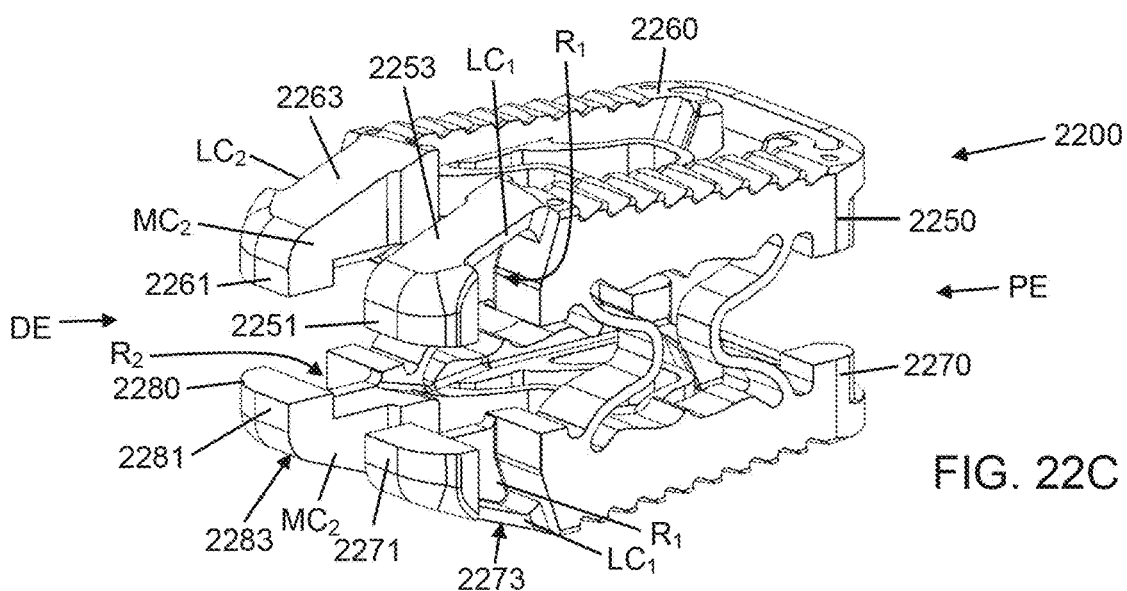

FIGS. 22A-22C illustrate components of a system having a cage 2200 with a tensioner, a central beam or shim (not shown) configured for expanding the cage, and a stabilizer 2207, according to some embodiments. FIGS. 22A-22B show the cage in a collapsed state without a shim to illustrate features of a cage, FIG. 22C shows the cage in an expanded state without the shim or stabilizer. The stabilizer can have any configuration that performs the functions set-forth herein for such a stabilizer. By way of example only, the stabilizer 2207 of the instant example has an H-configuration including a first vertical leg $VL_1$, a second vertical leg $VL_2$, a vertical support member VSM, and a cross-member (not shown) that connects the first vertical leg $VL_1$ at least substantially parallel to the second vertical leg $VL_2$. In addition, although not specifically shown in the instant example, the stabilizer 2207 may include any of the features of the various stabilizers discussed throughout this disclosure, including but not limited to an instrument engagement feature, locking feature, and/or a fortified leading end. FIG.

22A provides a perspective view of a collapsed cage 2200 that may be used in such a system. The cage may be any of the cages described above, and it should be understood that any feature described herein with respect to any cage may be included on cage 2200. By way of example, the cage 2200 has a proximal end PE, a distal end DE, a first top beam 2250, a first bottom beam 2270, a second top beam 2260, and a second bottom beam 2280, the beams being interconnected by flexible struts 2295 that allow for bilateral expansion and collapse of the cage 2200. In some embodiments, the cage 2200 includes one or more tensioners such as, for example, tension straps 2299T, 2299B. Moreover, the beams 2250, 2260, 2270, 2280 can have cleats 2205 to help avoid backout of the cage 2200 from the intervertebral space.

The distal end DE of each beam includes a leading face and a generally planar surface extending between the leading face and the cleats. More specifically, the first top beam 2250 includes a leading face 2251 and a generally planar surface 2253 extending between the leading face 2251 and the cleats 2205, the second top beam 2260 includes a leading face 2261 and a generally planar surface 2263 extending between the leading face 2261 and the cleats 2205, the first bottom beam 2270 includes a leading face 2271 and a generally planar surface 2273 extending between the leading face 2271 and the cleats 2205, and the second bottom beam 2280 includes a leading face 2281 and a generally planar surface 2283 extending between the leading face 2281 and the cleats 2205. In the instant example, each of the generally planar surfaces 2253, 2263, 2273, 2283 is tapered in the distal direction due to the difference in height dimensions between the main portion of the cage 2200 and the distal end of the cage 2200. It should be understood that the angle of the taper may vary according to the type of cage 2200 chosen for the particular procedure. The generally planar surfaces 2253, 2263, 2273, 2283 include medial edge cutouts $MC_1$, $MC_2$, and lateral edge cutouts $LC_1$, $LC_2$, for receiving at least a portion of the vertical legs $VL_1$, $VL_2$, or the vertical support member VSM therein when the cage 2200 is in a collapsed state. More specifically, the medial edge cutouts $MC_1$, $MC_2$ are configured to receive at least a portion of the vertical support member VSM therein, and the lateral edge cutouts $LC_1$, $LC_2$ are configured to receive portions of the vertical legs $VL_1$, $VL_2$. The beams 2250, 2260, 2270, 2280 further include lateral recesses $R_1$, $R_2$ in which the vertical legs $VL_1$, $VL_2$ can travel during the lateral expansion of the beams 2250, 2260, 2270, 2280 of the expandable cage 2200. The cage 2200 is expanded in such a way that the top and bottom edges of the vertical legs $VL_1$, $VL_2$ do not experience interference with the lateral edge cutouts $LC_1$, $LC_2$ during expansion of the cage 2200, during which the vertical legs $VL_1$, $VL_2$ travel into the lateral recesses $R_1$, $R_2$.

Figure 23A:
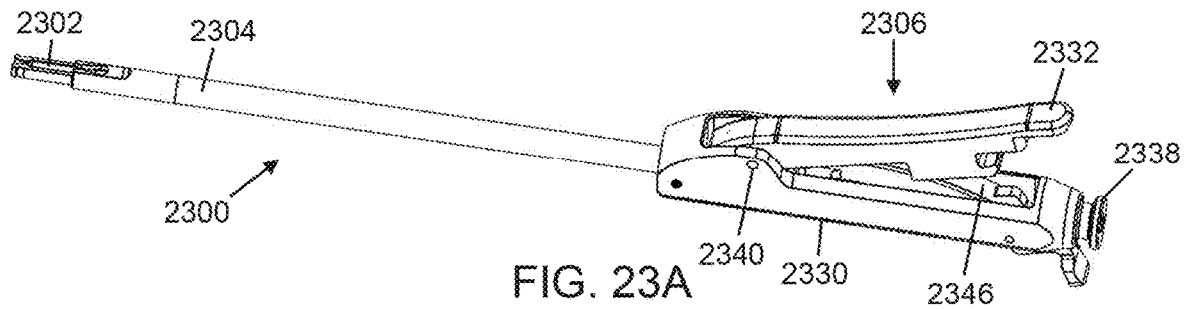
FIGS. 23A-23D illustrate components of a central beam removal tool, according to some embodiments.
Figure 23B:
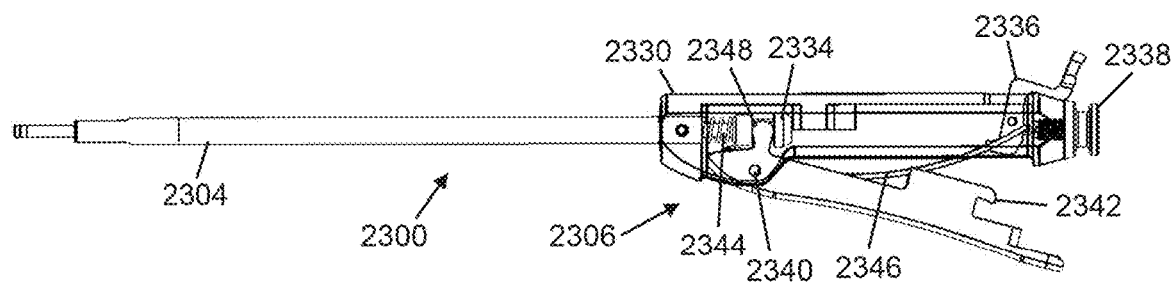
Figure 23C:
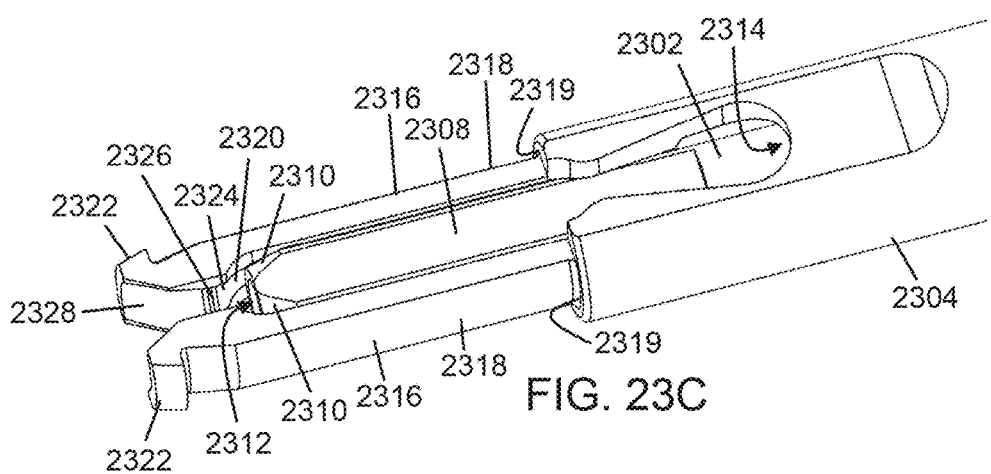
Figure 23D:
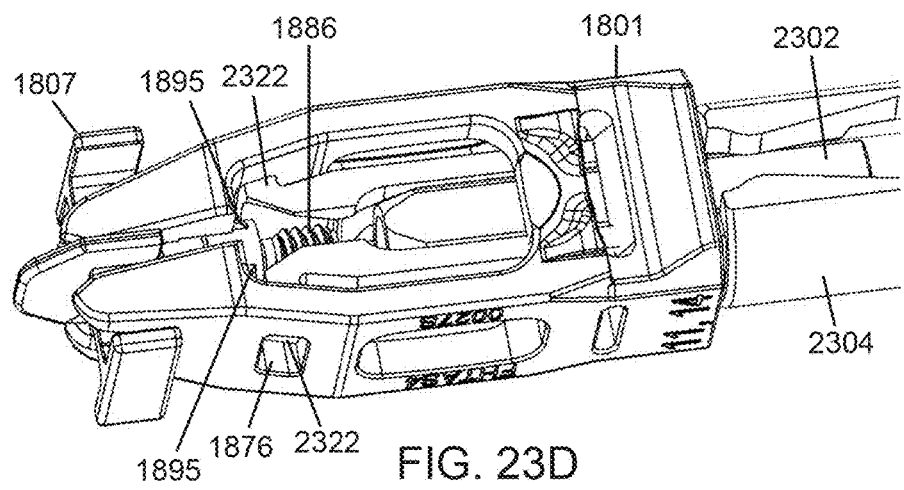

FIGS. 23A-23D illustrate an example of a shim removal tool 2300 suitable for use with the shim 1801 and locking stabilizer 1807 described above. FIG. 23A is a perspective view of the shim removal tool, FIG. 23B is a side plan view of the shim removal tool with the handle made transparent to enable viewing of certain interior elements, FIG. 23C is an enlarged view of the distal end of the shim removal tool, and FIG. 23D is an enlarged view of the distal end of the shim removal tool positioned within a shim. Generally, the shim removal tool 2300 facilitates disengagement, or unlocking, of the shim 1801 and the locking stabilizer 1807, which then enables the surgeon to remove the shim 1801 from the target site without also removing the shell and stabilizer. The removal tool 2300 accomplishes this by forcibly spreading the distal end of the shim 1801 apart until the shoulder on the shim is able to clear the locking barbs 1895 on the stabilizer 1807 (see FIGS. 18A-18I and associated description above).

By way of example, the shim removal tool 2300 includes an inner shaft 2302, an outer shaft 2304, and a handle assembly 2306. The inner shaft 2302 comprises a generally cylindrical elongated element having proximal and distal ends. The distal end includes one or more generally planar cutout sections 2308 distally tapered surfaces 2310 at the tip, and an axial aperture 2312 formed along the longitudinal axis of the inner shaft 2302. The generally planar cutout sections 2308 function to reduce the profile of the inner shaft 2302 at the distal end, for example to allow insertion into the shim 1801. The distally tapered surfaces 2310 may be generally planar or may have a convex curvature, and facilitate engagement with the proximal ramped surfaces 2324 and shoulders 2326 of the distal prongs 2316 of the outer shaft 2304 as the inner shaft 2302 is distally advanced, as described below. The axial aperture 2312 is sized and configured to receive (but not engage) the post 1886 of the stabilizer 1807, enabling the engagement point between the inserter and shim to be as distal as possible on the shim 1807. As will be explained below, the proximal end engages with the handle assembly 2306.

The outer shaft 2304 comprises a generally cylindrical hollow tube having a proximal end, a distal end, and an interior lumen 2314 extending longitudinally through the outer shaft 2304. The interior lumen 2314 is sized and configured to receive the inner shaft 2302 therein and further enable translation of the inner shaft 2302 within the outer shaft 2304. The proximal end is attached to the handle assembly 2306. The distal end includes a pair of prongs 2316 that are sized and shaped for entry into the shim 1801. Since the prongs 2316 are not as thick as the outer shaft 2304 (e.g. to enable flexing of the prongs during use), and the inner surfaces of the prongs are an extension of the inner lumen of the outer shaft 2304, a distal facing shelf 2319 is formed where the prongs 2316 extend away from the outer shaft 2304. By way of example, the prongs 2316 each have an outer surface 2318 having a convex curvature, an inner surface 2320 having a concave curvature, and a lateral flange 2322 configured for engagement with the removal slots 1876 on the shim 1801. The inner surface 2320 of each of the prongs 2316 has, at the distal end, a proximal concave ramp 2324, a shoulder 2326, and a distal concave ramp 2328. The proximal concave ramp 2324 provides a smooth surface to interact with the distal end of the inner shaft 2302 as the inner shaft 2302 is advanced through the outer shaft 2304. This interaction causes the prongs 2316 to be forced apart laterally until the inner shaft 2302 is fully inserted between the shoulders 2326. As the distal tip of the inner shaft 2302 is traversing the proximal ramps 2324, the lateral flanges 2322 are received within the removal slots 1876 of the shim 1801, and continued advancement of the inner shaft 2302 causes the prongs 2316 to exert outward force on the shim 1801. The vertical slots 1824, 1826 extending completely through the shim 1801 as described above enable the distal end of the shim 1801 to be spread apart enough to allow the shoulder 1834 of the shim 1801 to pass the locking barbs 1895 of the locking stabilizer 1807 in a proximal direction, thus "unlocking" the shim 1801. The distal ramp 2328 is configured to engage (or at least provide clearance for) the post 1886 of the locking stabilizer 1807.

The handle assembly 2306 comprises a handle 2330, lever 2332, inner shaft adapter 2334, lock hook 2336, and a tool engagement feature 2338. The lever 2332 is pivotably connected to the handle by a pair of pivot pins 2340, and further includes a lock flange 2342 near the proximal end. The proximal end of the inner shaft 2302 is connected to the inner shaft adapter 2334, which is connected to the lever 2332. A coiled spring 2344 positioned distally of the inner shaft adapter 2334 biases the removal tool 2300 in an "open" orientation. As the lever 2332 is depressed, the lever 2332 exerts a force on a leaf spring 2346, which along with a lever element 2348, cause the inner shaft adaptor 2334 to migrate in a distal direction. This migration in turn causes the inner shaft 2302 to advance distally through the outer shaft 2304, causing engagement with the shim 1801 as described above. When the lever 2332 is fully depressed (or nearly so), the lock flange 2342 will engage with the lock hook 2336, thereby locking the lever 2332 in a "closed" position. At this point, the inner shaft 2302 is fully advanced as described above, the lateral flanges 2322 are engaged with the removal slots 1876 on the shim 1801, and shim is spread apart in an "unlocked" position. The tool engagement feature 2338 may then be used to attach a secondary instrument, for example a slap hammer (not shown), to exert a sufficient proximal force on the shim 1807 to remove it from the cage.

Figure 24A:
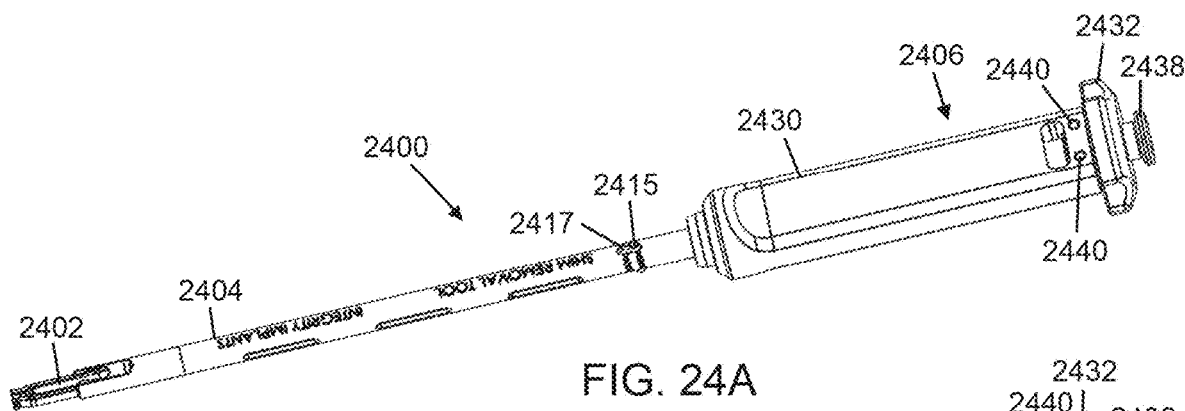
FIGS. 24A-24D illustrate components of another central beam removal tool, according to some embodiments.
Figure 24B:
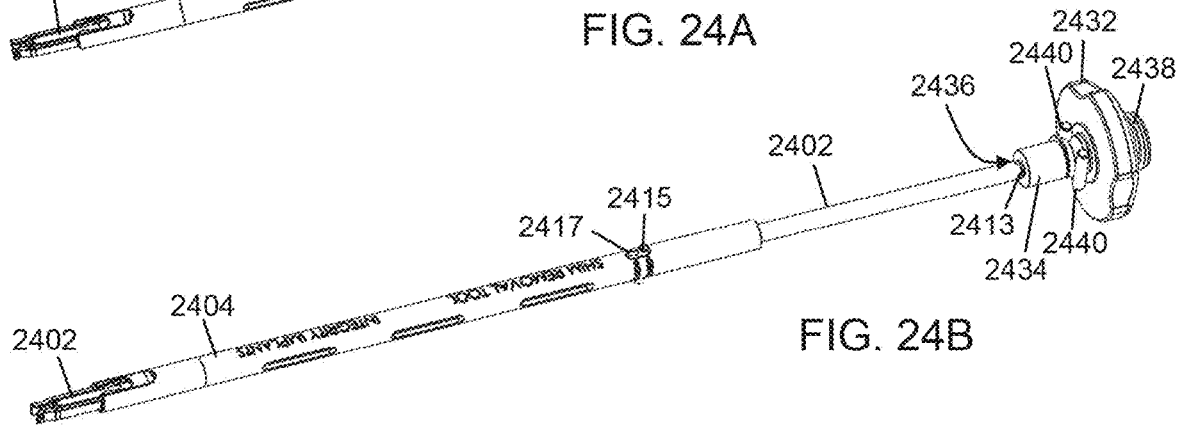
Figure 24C:
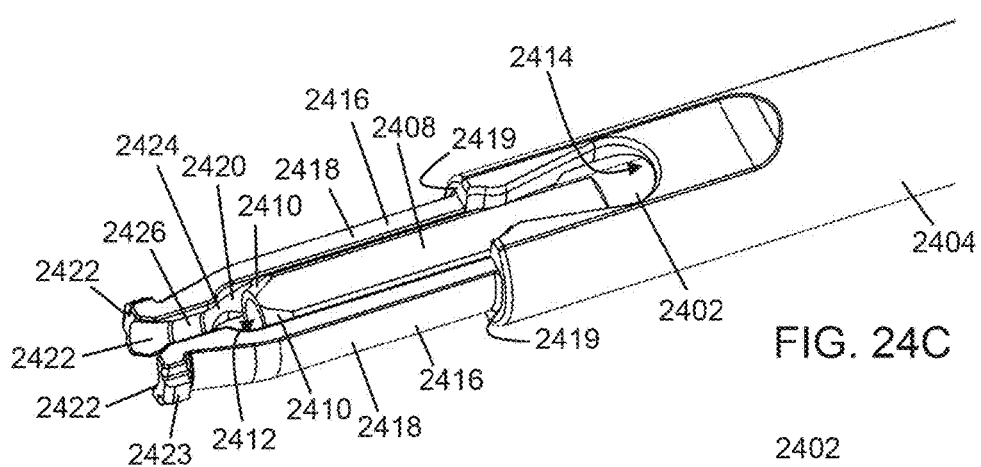
Figure 24D:
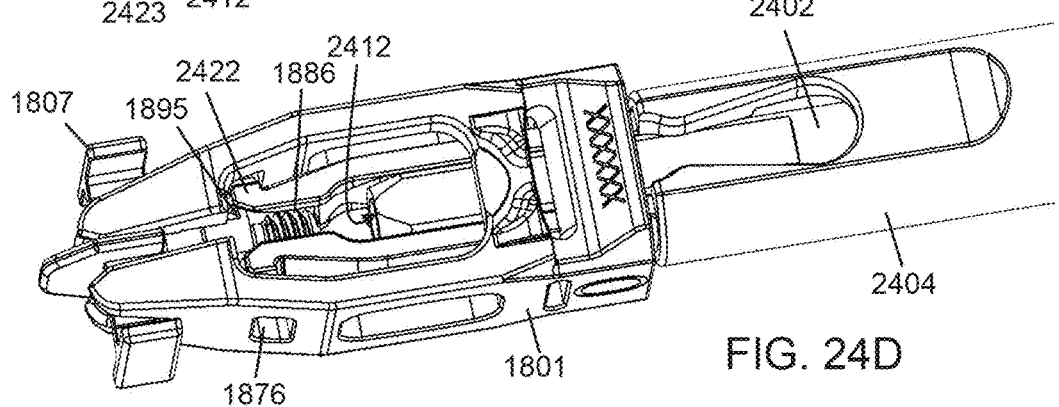

FIGS. 24A-24D illustrate another example of a shim removal tool 2400 suitable for use with the shim 1801 and locking stabilizer 1807 described above. FIG. 24A is a perspective view of the shim removal tool, FIG. 24B is a perspective view of the shim removal tool with the handle removed to enable viewing of certain interior elements, FIG. 24C is an enlarged view of the distal end of the shim removal tool, and FIG. 24D is an enlarged view of the distal end of the shim removal tool positioned within a shim. Generally, the shim removal tool 2400 facilitates disengagement, or unlocking, of the shim 1801 and the locking stabilizer 1807, which then enables the surgeon to remove the shim 1801 from the target site without also removing the shell and stabilizer. The removal tool 2400 accomplishes this by forcibly spreading the distal end of the shim 1801 apart until the shoulder on the shim is able to clear the locking barbs 1895 on the stabilizer 1807 (see FIGS. 18A-18I and associated description above).

By way of example, the shim removal tool 2400 includes an inner shaft 2402, an outer shaft 2404, and a handle assembly 2406. The inner shaft 2402 comprises a generally cylindrical elongated element having proximal and distal ends. The distal end includes one or more generally planar cutout sections 2408 distally tapered surfaces 2410 at the tip, and an axial aperture 2412 formed along the longitudinal axis of the inner shaft 2402. The generally planar cutout sections 2408 function to reduce the profile of the inner shaft 2402 at the distal end, for example to allow insertion into the shim 1801. The distally tapered surfaces 2410 may be generally planar or may have a convex curvature, and facilitate engagement with the proximal ramped surfaces 2424 and shoulders 2426 of the distal prongs 2416 of the outer shaft 2404 as the inner shaft 2402 is distally advanced, as described below. The axial aperture 2412 is sized and configured to receive (but not engage) the post 1886 of the stabilizer 1807, enabling the engagement point between the inserter and shim to be as distal as possible on the shim 1807. The proximal end includes threads 2413 that engage with the handle assembly 2406 and facilitate advancement of the inner shaft 2402, as will be explained below. In some embodiments, the inner shaft 2402 includes an indicator pin 2415 attached to and positioned near the middle of the inner shaft, the indicator pin 2415 interacting with a marked slot 2417 on the outer shaft 2404 to provide a visual indication to the user as to the status of the shim (e.g. "locked" or "unlocked"). By way of example, in an initial state the indicator pin 2415 is at the proximal end of the marked slot 2417, near markings on the outer shaft 2404 that indicate the shim 1801 is "locked". When the inner shaft 2402 is fully advanced (described below), the indicator pin 2415 is at the distal end of the marked slot 2417, near markings on the outer shaft 2404 that indicate the shim 1801 is "unlocked" and therefore ready to be removed by the user. The markings may be any markings suitable to communicate to the user the status of the shim, including but not limited to words (e.g. "locked", "unlocked"), pictures or icons (e.g. locked padlock, unlocked padlock, etc.), and the like.

The outer shaft 2404 comprises a generally cylindrical hollow tube having a proximal end, a distal end, and an interior lumen 2414 extending longitudinally through the outer shaft 2404. The interior lumen 2414 is sized and configured to receive the inner shaft 2402 therein and further enable translation of the inner shaft 2402 within the outer shaft 2404. The proximal end of the outer shaft 2404 is attached to the handle assembly 2406. The distal end includes a pair of prongs 2416 that are sized and shaped for entry into the shim 1801. Since the prongs 2416 are not as thick as the outer shaft 2404 (e.g. to enable flexing of the prongs during use), and the inner surfaces of the prongs are an extension of the inner lumen of the outer shaft 2404, a distal facing shelf 2419 is formed where the prongs 2416 extend away from the outer shaft 2404. By way of example, the prongs 2416 each have an outer surface 2418 having a convex curvature, an inner surface 2420 having a concave curvature, and a lateral flange 2422 configured for engagement with the removal slots 1876 on the shim 1801. The lateral flanges 2422 each include a flange extension 2423 configured to increase the material engaging the removal slots 1876. The inner surface 2420 of each of the prongs 2416 has, at the distal end, a proximal concave ramp 2424, a shoulder 2426, and a distal concave ramp 2428. The proximal concave ramp 2424 provides a smooth surface to interact with the distal end of the inner shaft 2402 as the inner shaft 2402 is advanced through the outer shaft 2404. This interaction causes the prongs 2416 to be forced apart laterally until the inner shaft 2402 is fully inserted between the shoulders 2426. As the distal tip of the inner shaft 2402 is traversing the proximal ramps 2424, the lateral flanges 2422 are received within the removal slots 1876 of the shim 1801, and continued advancement of the inner shaft 2402 causes the prongs 2416 to exert outward force on the shim 1801. The vertical slots 1824, 1826 extending completely through the shim 1801 as described above enable the distal end of the shim 1801 to be spread apart enough to allow the shoulder 1834 of the shim 1801 to pass the locking barbs 1895 of the locking stabilizer 1807 in a proximal direction, thus "unlocking" the shim 1801. The distal ramp 2428 is configured to engage (or at least provide clearance for) the post 1886 of the locking stabilizer 1807.

The handle assembly 2406 comprises a handle 2430 and a knob 2432. The knob 2432 includes a distal extension 2434 having a threaded axial lumen 2436 and a circumferential recess 2437, and a tool engagement feature 2438. The threaded axial lumen 2436 includes threads that are complementary to the threads 2413 of the inner shaft 2402. Thus, the knob 2432 is rotatably associated with the inner shaft 2402 through this threaded interaction. The knob 2432 is attached to the handle 2430 by a pair of retention pins 2440. The retention pins 2440 engage the knob 2432 in the circumferential recess 2437, which allows the knob 2432 to rotate while staying in the same position relative to the handle 2430. Thus, as the knob 2432 turns, the threaded interaction between the knob 2432 and the inner shaft 2402 causes the inner shaft 2402 to translate distally or proximally, depending on the direction of the rotation. By way of example, the threads are left hand threads, and as such the inner shaft 2402 will translate distally when the knob 2432 is rotated in a clockwise direction. As described above, the distal translation of the inner shaft 2402 causes engagement with the shim 1801. As previously noted, when the inner shaft 2402 is fully advanced as described above, the lateral flanges 2422 are engaged with the removal slots 1876 on the shim 1801, and shim is spread apart in an "unlocked" position. The indicator pin 2415 is at the distal end of the marked slot 2417, near markings on the outer shaft 2404 that indicate the shim 1801 is "unlocked" and therefore ready to be removed by the user. The tool engagement feature 2438 may then be used to attach a secondary instrument, for example a slap hammer (not shown), to exert a sufficient proximal force on the shim 1807 to remove it from the cage.

Figure 25A:
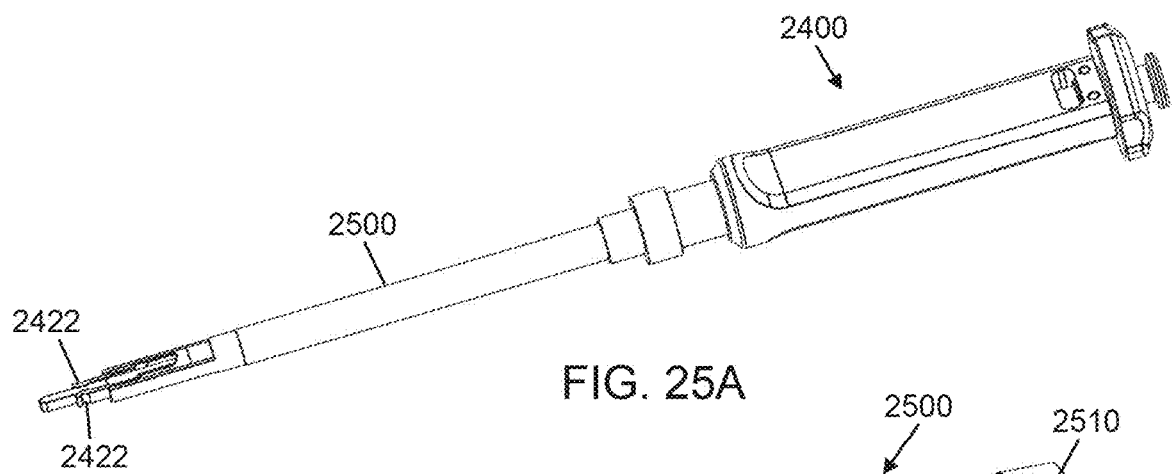
FIGS. 25A-25D illustrate components of another central beam removal tool including a depth stop/gauge, according to some embodiments.
Figure 25B:
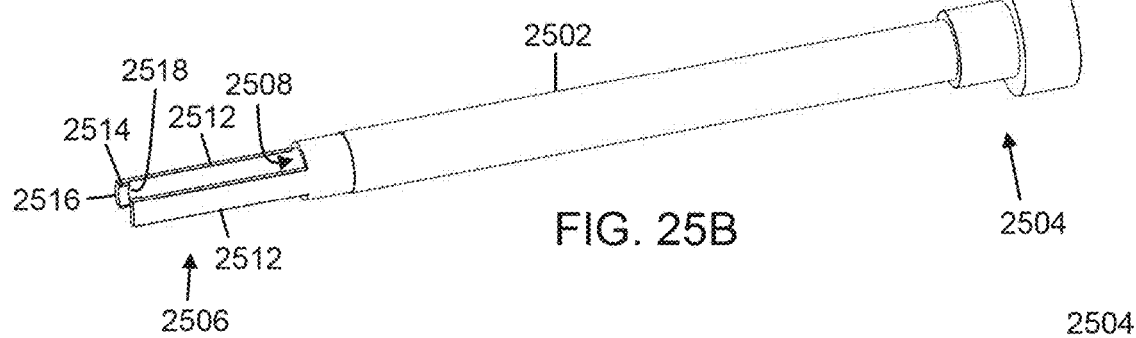
Figure 25C:
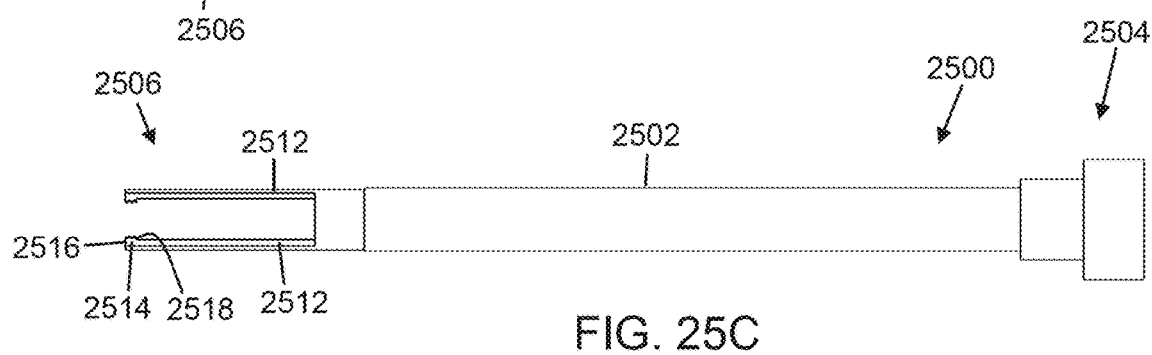
Figure 25D:
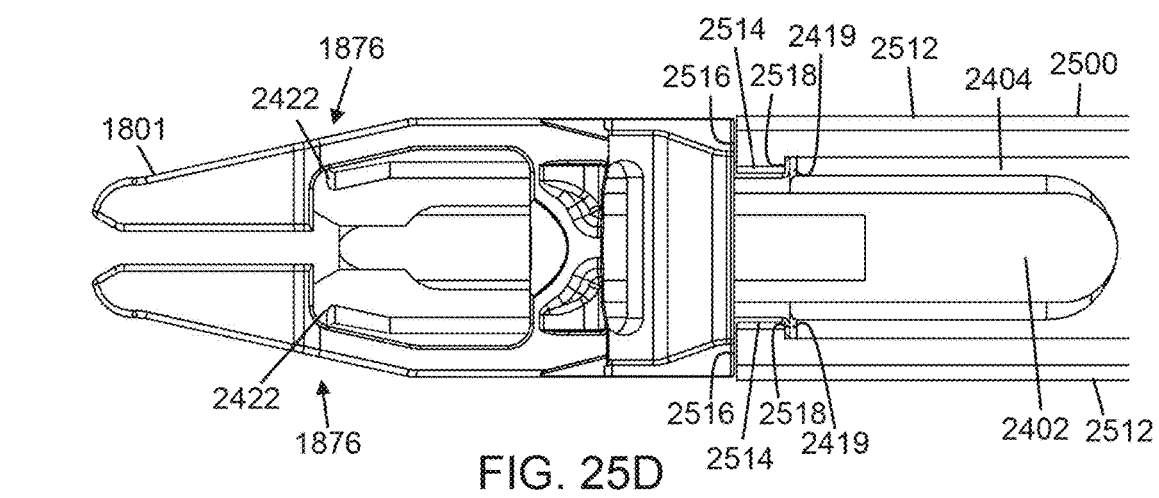

FIGS. 25A-25D illustrate the shim removal tool 2400 described above in use with an example depth stop/gauge 2500. FIG. 25A is a perspective view of the shim removal tool 2400 coupled with a depth stop/gauge 2500, according to some embodiments. FIG. 25B is a perspective view of the depth stop/gauge 2500, FIG. 25C is a side plan view of the depth stop/gauge 2500, and FIG. 25D is a perspective view of the distal end of the shim removal tool 2400 with depth stop/gauge 2500 in use with a shim 1801 of the type described above. As will be seen, the depth stop/gauge 2500 provides another way of efficiently determining how far the shim removal tool 2400 must be inserted to achieve proper positioning within the shim 1801. The depth stop/gauge 2500 attachment described herein accomplishes this by providing a physical barrier to advancement of the outer shaft 2404, ensuring that the lateral prongs 2422 are aligned with the removal slots 1876 of the shim 1801.

By way of example, the depth stop/gauge 2500 comprises a generally tubular hollow shaft 2502 having a proximal end 2504 and a distal end 2506. The tubular hollow shaft 2502 includes a lumen 2508 extending the length of the depth stop/gauge 2500, the lumen 2508 sized and configured to receive the outer shaft 2404 of the shim removal tool 2400 therethrough. The proximal end includes a fitting 2510 to facilitate engagement between the depth stop/gauge 2500 and shim removal tool 2400. In some embodiments, the fitting 2510 covers the indicator pin 2415 and marked slot 2417. In some embodiments, the fitting 2510 does not cover the indicator pin 2415 and marked slot 2417, for example by including a cutout window or transparent material. The distal end 2506 includes a pair of prongs 2512 extending distally from the end of the shaft 2502. The prongs 2512 each have a shoulder 2514 protruding medially at the distal tip. The shoulder 2514 provides the physical barrier to advancement of the outer shaft 2404, and includes a distal facing contact surface 2516 and a proximal facing contact surface 2518. The distal facing contact surface 2516 is configured to abut the proximal face of the shim 1801 during use. The proximal facing contact surface 2518 is configured to abut the distal facing shelf 2419 of the shim removal tool 2400 (or the distal facing shelf 2319 of the shim removal tool 2300) to prevent further advancement of the outer shaft 2404.

Figure 26A:
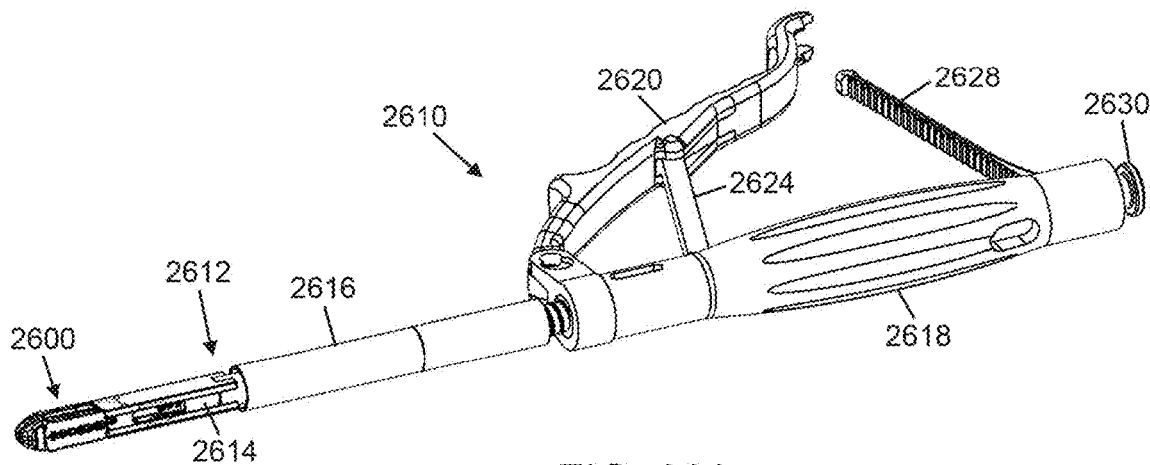
FIGS. 26A-26C illustrate components of an insertion tool for use with a system having a cage with a stabilizer and central beam configured for expanding the cage, the insertion tool including a cage retention sleeve, according to some embodiments.
Figure 26B:
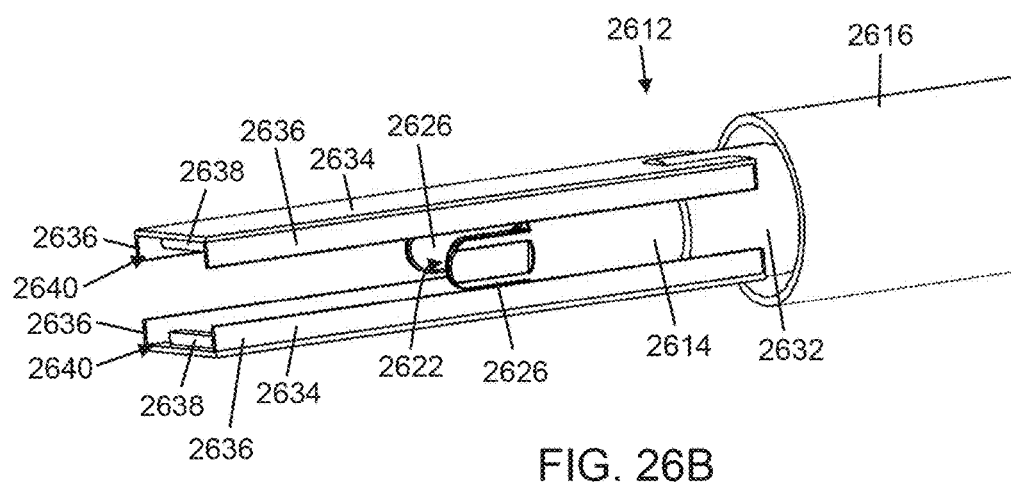
Figure 26C:
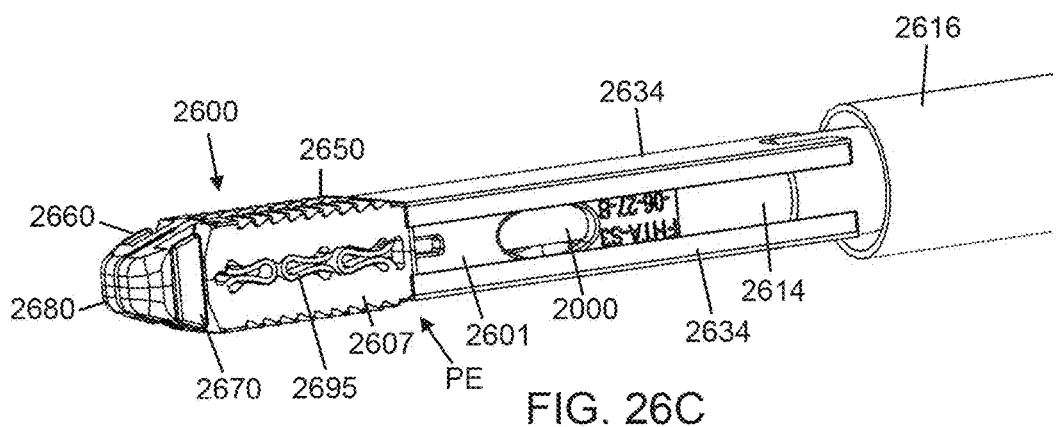

FIGS. 26A-26C illustrate an example of an insertion tool 2610 with a retention sleeve 2612 configured for use with components of an implant system having a cage 2600, a shim 2601 configured for expanding the cage, and a stabilizer 2607, according to some embodiments, including but not limited to any implant system described herein above. FIG. 26A illustrates the inserter with retention sleeve engaged with an implant system, FIG. 26B illustrates an enlarged view of the distal end of the inserter with the retention sleeve, and FIG. 26C illustrates an enlarged view of the distal end of the inserter with retention sleeve coupled with an implant system. By way of example only, the cage 2600 shown in FIGS. 26A-26C includes a proximal end PE, a first top beam 2650, a first bottom beam 2670, a second top beam 2660, and a second bottom beam 2680, the beams interconnected by flexible struts 2695 that allow for bilateral expansion and collapse of the cage 2600. The shim 2601 may include any feature of any of the shims described herein, and the stabilizer 2607 may include any feature of any of the stabilizers described herein.

The insertion tool 2610 may be any insertion tool configured to insert any of the implant systems described herein. For the purpose of illustration, the insertion tool 2600 includes an inner cannula 2614, an outer sleeve 2616, handle 2618, and lever 2620. By way of example, the inner cannula 2614 has an interior lumen 2622 extending the length of the inner cannula 2614, the interior lumen 2622 is sized and configured to receive a guide pin 2000 (see, e.g., FIGS. 20A-20C) therein. The proximal end of the inner cannula 2614 is operably associated with the lever 2620 via a link bar 2624, which operates such that, when the lever is actuated, the inner cannula 2614 is advanced in a distal direction. The distal end of the inner cannula 2614 includes prongs 2626 extending distally therefrom. The prongs 2626 are sized and configured to engage the shim 2607, for example by insertion into an axial aperture formed in the shim (not shown, but see axial aperture 1842 of shim 1807 in FIG. 18G). Thus, when the lever is actuated the inner cannula 2614 through its engagement with the shim 2601 advances the shim 2601 into the expandable cage 2600. The insertion tool 2610 further includes a ratchet bar 2628 configured to interact with the distal end of the lever 2620, and a tool engagement feature 2630 configured to provide an attachment point for additional instruments, for example including but not limited to a slap hammer.

The retention sleeve 2612 includes a collar 2632 and a pair of elongated panels 2634 extending from the distal end of the collar 2632. The collar 2632 comprises a tubular element configured to engage the outer surface of the inner cannula 2614 to couple the retention sleeve 2612 to the inner cannula 1614. Each of the elongated panels 2634 is generally planar with smooth surfaces and a rectangular shape. Each elongated panel 2634 includes a pair of sidewalls 2636 extending perpendicularly inward (e.g. toward the other panel) and extending the length of the elongated panel, and a distal bumper 2638 positioned on the inner surface of the elongated panel and extending between the sidewalls 2636. The distal bumper 2638 is offset from the distal edge of the elongated panel 2634 such that the distal bumper and sidewalls form a distal pocket 2640 configured to engage and retain the proximal end of the cage 2600 during insertion into the disc space and further during initial insertion of the shim 2601 into the cage 2600, at least until the cage 2600 undergoes expansion.

Figure 27A:
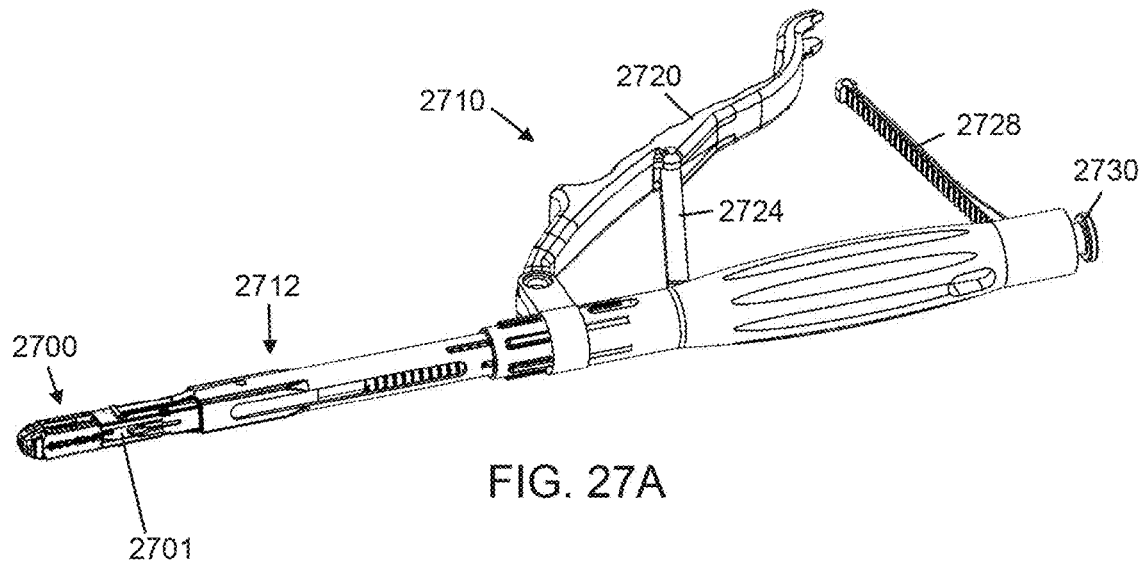
FIGS. 27A-27C illustrate components of an insertion tool for use with a system having a cage with a stabilizer and central beam configured for expanding the cage, the insertion tool including a retractable cage retention sleeve, according to some embodiments.
Figure 27B:
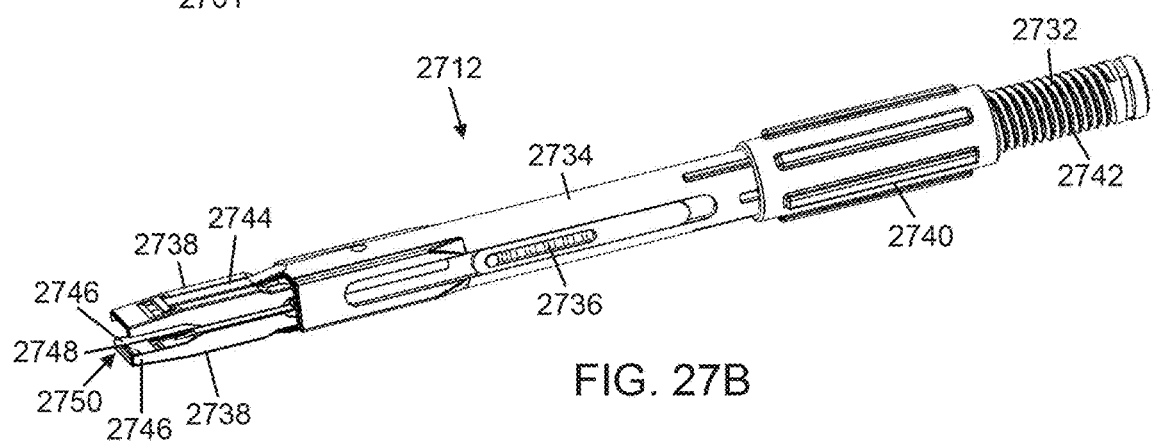
Figure 27C:
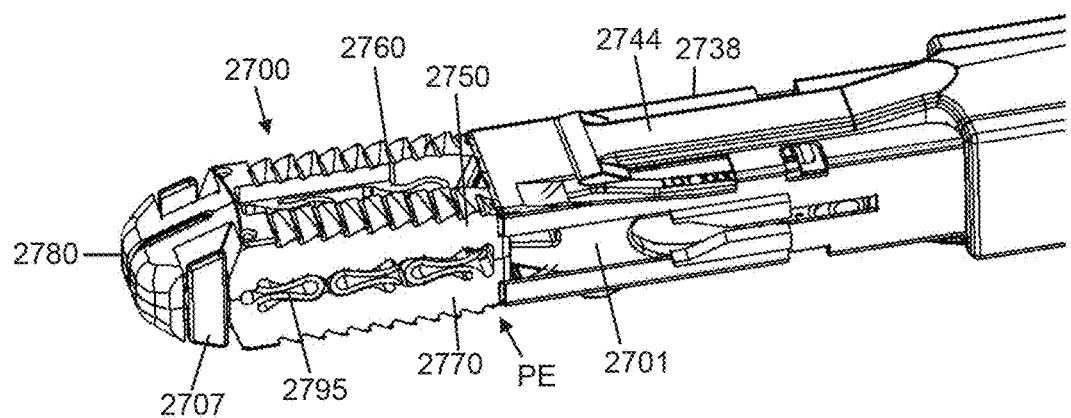

FIGS. 27A-27C illustrate an example of an insertion tool 2710 with a retractable retention sleeve 2712 configured for use with components of an implant system having a cage 2700, a shim 2701 configured for expanding the cage, and a stabilizer 2707, according to some embodiments, including but not limited to any implant system described herein above. FIG. 27A illustrates the inserter with retractable retention sleeve engaged with an implant system, FIG. 27B illustrates the retractable retention sleeve assembly, and FIG. 26C illustrates an enlarged view of the distal end of the inserter with retractable retention sleeve assembly coupled with an implant system. By way of example only, the cage 2700 shown in FIGS. 27A-27C includes a proximal end PE, a first top beam 2750, a first bottom beam 2770, a second top beam 2760, and a second bottom beam 2780, the beams interconnected by flexible struts 2795 that allow for bilateral expansion and collapse of the cage 2700. The shim 2701 may include any feature of any of the shims described herein, and the stabilizer 2707 may include any feature of any of the stabilizers described herein.

The insertion tool 2710 may be any insertion tool configured to insert any of the implant systems described herein. For the purpose of illustration, the insertion tool 2700 includes an inner cannula (not shown, but similar to inner cannula 2614 described above), handle 2718, lever 2720, ratchet bar 2728, and tool engagement feature 2730, which are identical in form and function to the inner cannula 2614, handle 2618, lever 2620, ratchet bar 2628, and tool engagement feature 2630 of the insertion tool 2600 described above. Thus, when the lever 2720 is actuated the inner cannula through its engagement with the shim 2701 advances the shim 2701 into the expandable cage 2700. With reference to FIG. 27, when the cage 2700 and shim 2701 are initially loaded onto the inserter, the retention sleeve 2712 is in a retracted position, with the knob 2740 near the proximal end of the threaded section 2742 and the panels 2738 near the proximal end of the shim 2701. The user then rotates the knob 2740, in some embodiments, which causes the knob 2740 to migrate distally along the threaded section 2742, in turn causing the prongs 2744 to urge the panels 2738 distally over the shim 2701. When the panels 2738 reach the cage 2700, distal migration of the panels 2738 is stopped by a set of pins (not shown), which distal migration of the prongs 2744 continues until the prongs 2744 pinch the panels 2738 together, with the proximal end PE of the cage 2700 within the distal pocket 2750. Rotating the knob 2740 in the opposite direction causes the panels 2738 to disengage from the cage 2700.

By way of example only, the retractable retention sleeve assembly 2712 described herein includes a base 2732, retraction element 2734, spring 2736, a pair of elongated panels 2738, and a knob 2740. The base 2732 includes an engagement element (not shown) for facilitating engagement with the insertion tool 2710 and an external threaded section 2742 for threaded engagement with the knob 2740. The retraction element 2734 comprises an elongated member that is rotatably coupled with the knob 2740, in that the knob 2740 is able to rotate about the proximal end of the retraction element 2734 while the retraction element 2734 does not itself rotate. The distal end of the retraction element 2734 includes a pair of engagement prongs 2744 that are coupled with the elongated panels 2738. The spring 2736 is positioned between the base 2732 and the elongated panels 2738, and functions to impart a distal bias on the elongated panels 2738. Each of the elongated panels 2738 is generally planar with smooth surfaces and a rectangular shape. Each elongated panel 2738 includes a pair of sidewalls 2746 extending perpendicularly inward (e.g. toward the other panel) and extending the length of the elongated panel, and a distal bumper 2748 positioned on the inner surface of the elongated panel and extending between the sidewalls 2746. The distal bumper 2748 is offset from the distal edge of the elongated panel 2738 such that the distal bumper and sidewalls form a distal pocket 2750 configured to engage and retain the proximal end of the cage 2700 during insertion into the disc space and further during initial insertion of the shim 2701 into the cage 2700, at least until the cage 2700 undergoes expansion. Rotation of the knob 2740 in a clockwise direction causes the knob 2740 to migrate proximally along the threaded section 2742, which pulls or retracts the elongated panels 2738 away from the cage 2700.

Figure 28A:
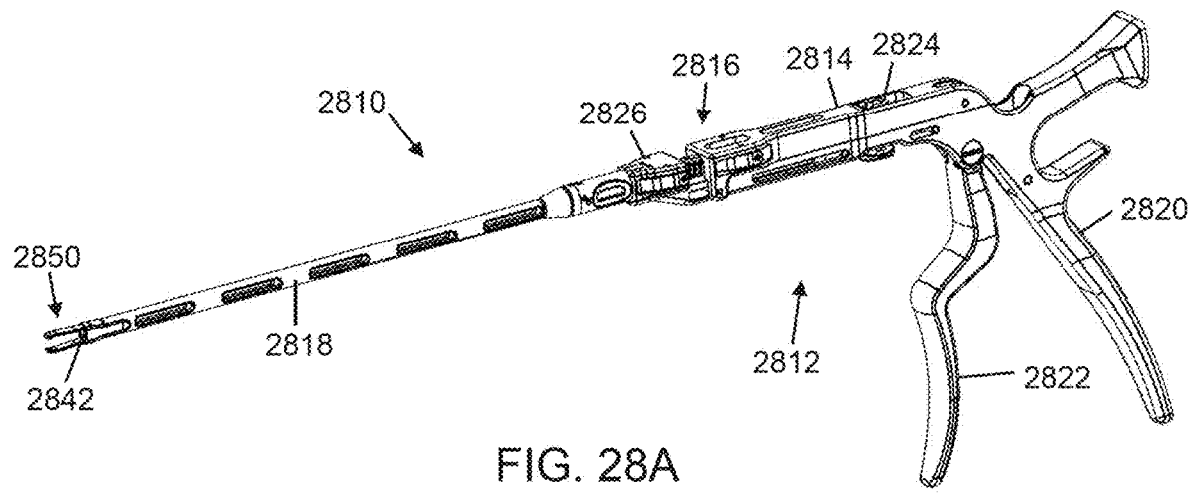
FIGS. 28A-28C illustrate components of an insertion tool for use with a system having a cage with a stabilizer and central beam configured for expanding the cage, according to some embodiments.
Figure 28B:
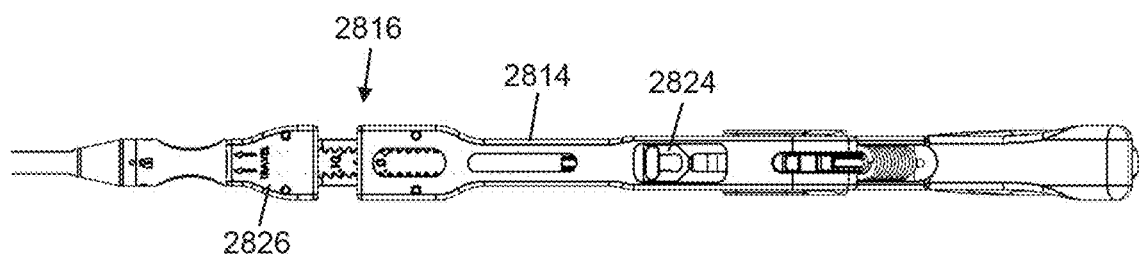
Figure 28C:
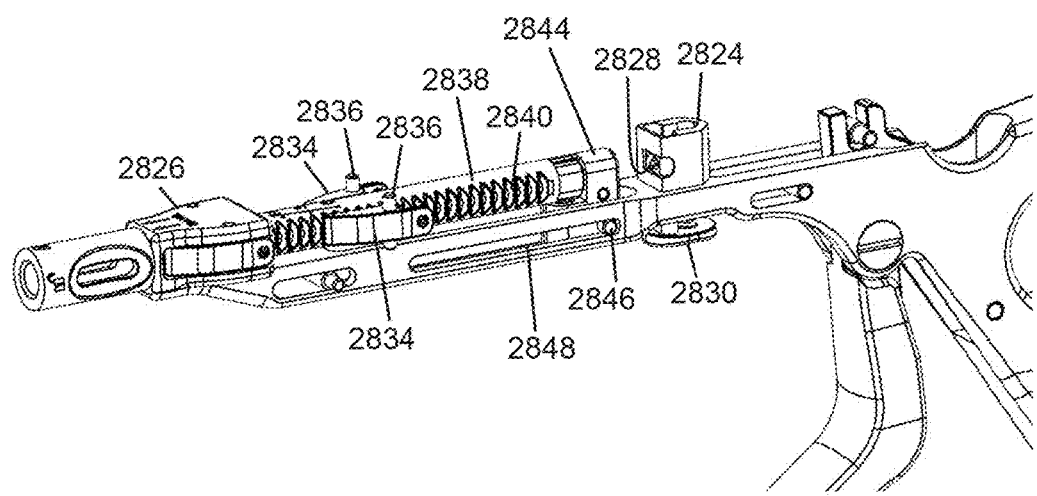

FIGS. 28A-28C illustrate an example of an insertion tool 2810 configured for use with components of an implant system having a cage, a shim configured for expanding the cage, and a stabilizer, according to some embodiments, including but not limited to any implant system described herein above (see, e.g FIGS. 18A-18I). FIG. 28A illustrates a perspective view of the insertion tool 2810, FIG. 28B is a top plan view of the proximal portion of the insertion tool, and FIG. 28C is a perspective view of the insertion tool 2810 without the elongated shaft and with a top translation element removed to show various inner components of the insertion tool 2810. By way of example, the insertion tool 2810 includes a base 2812, translation element 2814, ratchet assembly 2816, and elongated shaft 2818. Although not pictured, the insertion tool 2810 is configured for use with a guide pin, for example the guide pin 2000 described above with reference to FIGS. 20A-20C. By way of example, the stabilizer is coupled with the guide pin 2000 as shown in FIG. 20A. The cage may also be associated with the stabilizer at this point. Generally, the guide pin may be inserted into the elongated shaft 2818. The distal end of the elongated shaft 2818 is configured to engage a shim (e.g. shim 1901 in FIGS. 20A-20C). During implantation, once the collapsed cage is in position in the disc space, the user actuates the lever, which causes the elongated shaft 2818 (and engaged shim) to advance distally toward and/or into the cage.

By way of example, the base 2812 comprises a handle 2820, a lever 2822, a guide pin holder 2824, and a distal ratchet element 2826. The guide pin holder 2824 includes a spring-loaded capture element comprising an aperture 2828 for receiving the proximal end of a guide pin and a release button 2830, which when depressed enables the guide pin to be disengaged from the capture element. The distal ratchet element 2826 may be fixed to the base 2812 and, as will be explained below, operates in concert with the proximal ratchet element 3832 to give the user more control over the insertion process.

The translation element 2814 is coupled with the lever 2822 and includes a proximal ratchet element 2832 that functions to advance the elongated shaft 2818 in a distal direction. The proximal ratchet element 2832 includes a pair of ratchet levers 2834, each pivotally connected to the translation element 2814 by a pin 2836.

The ratchet assembly 2816 includes a ratchet tube 2838 connected to and positioned about the proximal end of the elongated shaft 2818. The ratchet tube 2838 includes a plurality of ratchet indents 2840 having steep distal faces and tapered proximal faces. Thus, when the lever 2822 is actuated, the translation element 2814 moves in a distal direction. The proximal ratchet element 2832, being part of the translation element 2814, also moves in a distal direction. The ratchet levers 2834 are not able to overcome the steep distal faces of the ratchet indents 2840, and therefore the ratchet tube 2838 is pushed in a distal direction as well. When the lever 2822 is released, the tapered proximal faces of the ratchet indents 2840 allow the ratchet levers 2834 to pass, allowing the translation element 2814 to return to its initial state. The ratchet tube 2838 is held in place, however by the distal ratchet element 2826, which is stationary to the base 2812, so the distance of distal translation gained by the ratchet tube 2838 is not lost when the lever 2822 is released.

The elongated shaft 2818 has a proximal end, a distal end, and a generally cylindrical lumen 2842 extending the length of the elongated shaft 2818. The lumen 2842 is sized and configured to receive the guide pin (not shown) therein. The proximal end of the elongated shaft 2818 is secured by a shaft holder 2844. The shaft holder is translatably associated with the base 2812 by virtue of a pair of pins 2846 extending laterally from either side of the shaft holder 2844 into horizontal slots 2848 formed in the base 2812. The distal end of the elongated shaft includes a shim engagement feature 2850, which in the instant example is a pair of prongs configured to engage a portion of a shim (e.g., axial aperture). As previously mentioned, the ratchet tube 2838 is connected to the proximal end of the elongated shaft 2818 or alternatively the ratchet tube 2838 is connected to the shaft holder 2844. In either case, translation of the ratchet tube 2838 results in translation of the elongated shaft 2818, which in turn advances the attached shim distally into the cage (e.g. as described above). In some embodiments the elongated shaft 2818, or at least a portion thereof, is rotatable by ninety degrees between a "locked" position (e.g. in which the shim engagement feature is secured to the shim) and an "unlocked" position (e.g. in which the shim engagement feature 2850 is not secured to the shim). In some embodiments, an upper facing surface of the ratchet tube 2838 may include markings to visually indicate to the user the actual distance that the elongated shaft 2818, and therefore the attached shim, has been translated.

Figure 29A:
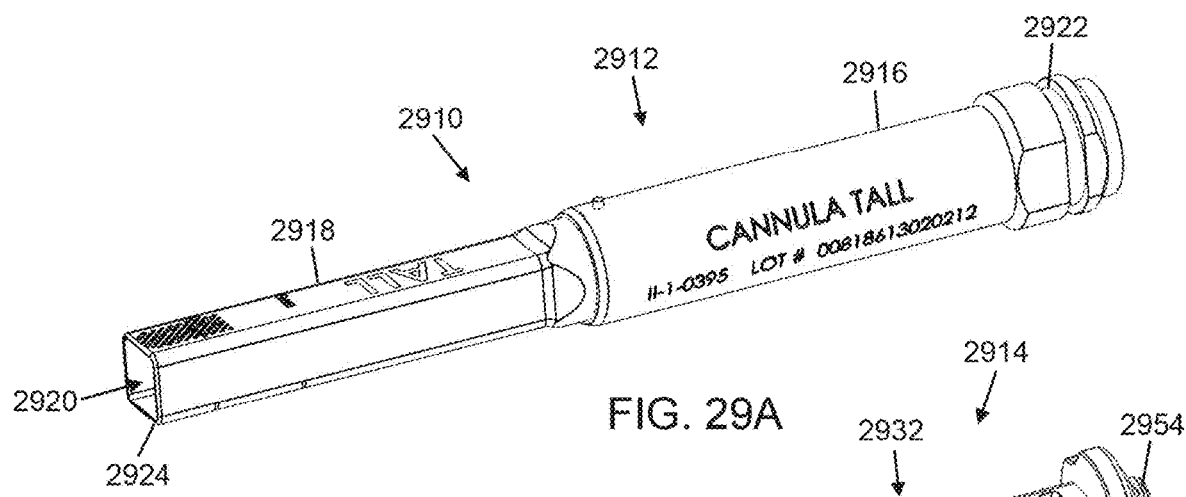
FIGS. 29A-29D illustrate components of a system having a cannula and an expandable obturator, according to some embodiments.
Figure 29B:
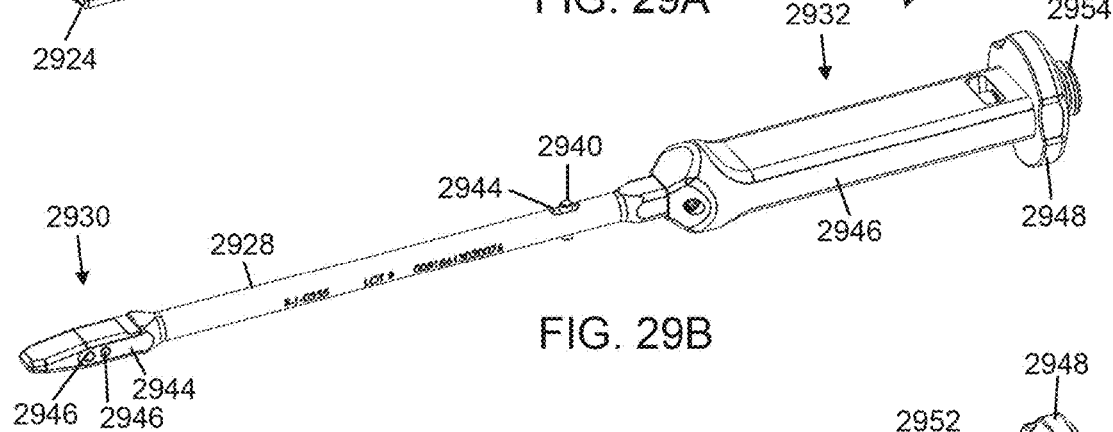
Figure 29C:
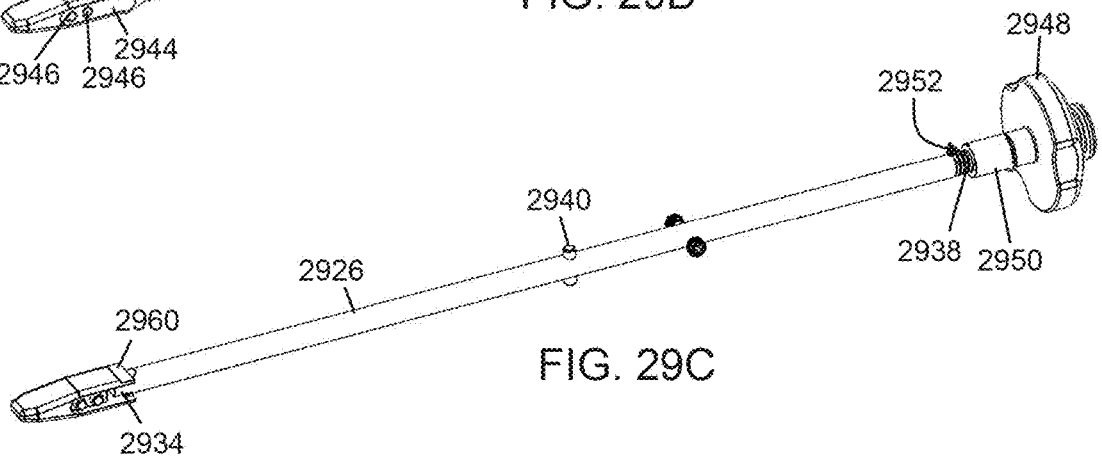
Figure 29D:
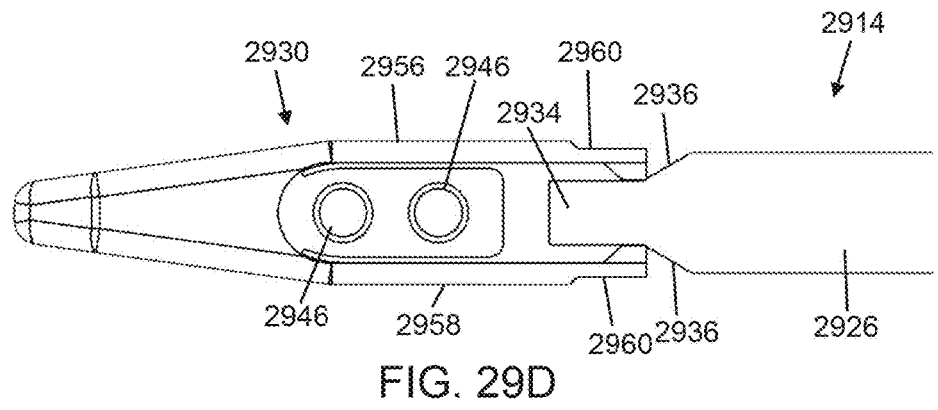

FIGS. 29A-29D illustrate an example of a cannula assembly 2910, according to some embodiments. The cannula assembly 2910 enables a user to deliver or insert the distal end of the cannula to a surgical target site without exposing the surgical target site or body tissue surrounding the operative corridor to trauma potentially caused by the distal edge of the cannula during insertion. The cannula assembly 2910 includes a cannula 2912 and an obturator 2914. FIG. 29A illustrates an example of a cannula 2912, FIG. 29B illustrates an example of an obturator 2914, FIG. 29C illustrates the obturator 2914 with the handle and outer shaft removed to expose interior structure, and FIG. 29D illustrates an enlarged view of the distal end of the obturator 2914 with the outer shaft removed.

By way of example, the cannula 2912 has a generally cylindrical proximal portion 2916, a generally square-shaped distal portion 2918, and an axial lumen 2920 extending longitudinally through the cannula 2912. The proximal portion 2916 includes a circumferential recess 2922 configured to facilitate engagement with additional instruments (not shown). The distal portion 2918 includes a distal edge 2924 surrounding the opening of the lumen 2920.

By way of example, the obturator 2914 includes an inner shaft 2926, an outer shaft 2928, an expandable wedge member 2930, and a handle assembly 2932. The inner shaft 2926 comprises a generally cylindrical elongated element having proximal and distal ends. The distal end includes a block-shaped tip 2934 and a pair of ramped surfaces 2936 at the tip. The block-shaped tip 2934 functions as a wedge element to increase the height of the top and bottom faces of the wedge member 2930. The ramped surfaces 2936 may be generally planar or may have a convex or concave curvature, and facilitate expansion of the expandable wedge member 2930 as the inner shaft 2926 is distally advanced, as described below. The proximal end includes threads 2938 that engage with the handle assembly 2932 and facilitate advancement of the inner shaft 2926, as will be explained below. In some embodiments, the inner shaft 2926 includes an indicator pin 2940 attached to and positioned near the middle of the inner shaft, the indicator pin 2940 interacting with a slot 2942 on the outer shaft 2928 to provide a visual indication to the user as to the status of the wedge member 2930 (e.g. "expanded" or "collapsed"). By way of example, in an initial state the indicator pin 2940 is at the proximal end of the slot 2942. When the inner shaft 2926 is fully advanced (described below), the indicator pin 2940 is at the distal end of the slot 2942.

The outer shaft 2928 comprises a generally cylindrical hollow tube having a proximal end, a distal end, and an interior lumen extending longitudinally through the outer shaft 2928. The interior lumen is sized and configured to receive the inner shaft 2926 therein and further enable translation of the inner shaft 2926 within the outer shaft 2928. The proximal end of the outer shaft 2928 is attached to the handle assembly 2932. The distal end of the outer shaft 2928 includes a pair of prongs 2944 that couple the outer shaft 2928 to the wedge member 2930 by way of pins 2946.

The handle assembly 2932 comprises a handle 2946 and a knob 2948. The knob 2948 includes a distal extension 2950 having a threaded axial lumen 2952, and a tool engagement feature 2954. The threaded axial lumen 2952 includes threads that are complementary to the threads 2938 of the inner shaft 2926. Thus, the knob 2948 is rotatably associated with the inner shaft 2926 through this threaded interaction. As the knob 2948 turns, the threaded interaction between the knob 2948 and the inner shaft 2926 causes the inner shaft 2926 to translate distally or proximally, depending on the direction of the rotation. In some embodiments, the threads are left hand threads, and as such the inner shaft 2926 will translate distally when the knob 2948 is rotated in a clockwise direction. The distal translation of the inner shaft 2926 causes the block-shaped tip 2934 to advance into the wedge member 2930, causing the top panel 2956 and bottom panel 2958 to pivot away from the midline of the instrument. The proximal end of the expandable wedge member 2930 is expanded to a height in which the distal edge 2924 of the cannula 2912 is flushly associated with proximal recesses 2960 formed in the top and bottom panels 2956, 2958. This creates a seamless smooth transition between the cannula 2912 and expandable wedge member 2930 of the obturator 2914. This combination can then be advanced to a surgical target site, with the smooth wedge of the obturator gently displacing tissue. When the leading edge of the cannula has been delivered to the desired position (e.g. an intervertebral space), the wedge member 2930 may be collapsed by rotating the knob 2948 in a counterclockwise direction. The obturator 2914 may then be removed from the target site through the cannula 2912, which is left in place for further use.

FIGS. 30A-30E illustrate another example of an insertion tool 3010 configured for use with components of an implant system having a cage 3000, a shim 3001 configured for expanding the cage, and a stabilizer 3007, according to some embodiments, including but not limited to any implant system described herein above (see, e.g. FIGS. 18A-18I). FIG. 30A illustrates a perspective view of the insertion tool 3010 with shim 3001 and cage 3000, FIG. 30B illustrates a perspective view of the insertion tool 3010, FIG. 30C is a perspective view of the handle assembly of the insertion tool with the housing removed, FIG. 30D is a perspective view of the distal end of the insertion tool 3010, and FIG. 30E is a perspective view of the translation element 3060. The insertion tool 3010 is configured for use with a guide pin (not pictured) coupled to the stabilizer, for example the guide pin 2000 described above with reference to FIGS. 20A-20C. By way of example, the insertion tool 3010 includes a housing 3012, guide pin holder 3014, shim holder 3016, and translation assembly 3018.

By way of example, the housing 3012 is a generally rectangular box-shaped unit having an external surface 3020 including friction elements 3022, a distal aperture 3024, proximal aperture 3026, and a pair of lateral slots 3028. The friction elements 3022 may be any element enhancing the grip of a user, including but not limited to a plurality of slots (as shown), ridges, bumps, and/or frictional material. The distal aperture 3024 provides an egress window for the elongated shaft 3038 of the shim holder 3016. The proximal aperture 3026 provides an egress window for the drive shaft 3058. The slots 3028 are configured to translationally receive the control tabs 3056 of the coupler 3042, as will be explained below.

As previously mentioned, the insertion tool 3010 is configured for use with a guide pin (not pictured) coupled to the stabilizer, for example the guide pin 2000 described above with reference to FIGS. 20A-20C. The guide pin is 2000 inserted through the elongated shaft 3038 of the shim holder 3016. The guide pin holder 3014 includes a spring-loaded capture element 3030 pivotally anchored to the housing 3012 comprising an aperture 3032 for receiving the proximal end of a guide pin 2000 and a release button 3034, which when depressed enables the guide pin 2000 to be disengaged from the capture element 3030. A spring 3036 exerts a force on the capture element 3030 to bias the capture element 3030 in a "locked" position. In pressing the release button 3034, the user overcomes this force to temporarily move the capture element 3030 to an "unlocked" position, in which the guide pin 2000 may be disengaged from the guide pin holder 3014.

The shim holder 3016 includes an elongated shaft 3038, a distal engagement feature 3040, and a coupler 3042. The elongated shaft 3038 has a proximal end, a distal end, and a generally cylindrical lumen 3044 extending the length of the elongated shaft 3038. The lumen 3044 is sized and configured to receive the guide pin (not shown) therein. The proximal end of the elongated shaft 3038 is secured to a first side of the coupler 3042. The distal engagement feature 3040 is positioned at the distal end of the elongated shaft 3038 and includes a distal aperture 3046 providing access to the lumen 3044 of the elongated shaft 3038, a pair of prongs 3048 configured to engage a portion of the shim 3001 (e.g., axial aperture), and an engagement surface 3050 configured to interface with the shim 3001 to enable the shim holder 3016 to push the shim 3001 in a distal direction. By way of example may be similar to shim 1801 of FIGS. 18A-18I, shim 1901 of FIGS. 20A-20C, or any other suitable shim element. The coupler 3042 includes a first portion 3052 connected with the elongated shaft 3038 and a second portion 3054 affixed to the translation element 3060 (described below). The first and second portions 3052, 3054 each include a control tab 3056 extending laterally away from the coupler, each control tab configured to be slideably received within one of the lateral slots 3028 of the housing 3012. The control tabs 3056 help prevent rotation of the translation element and/or coupler during use.

The translation assembly 3018 includes a drive shaft 3058, translation element 3060, and a handle element 3062. The drive shaft 3058 has a proximal portion 3064 and a distal portion 3066. The proximal portion 3064 protrudes from the housing 3012 and includes a shaped end 3068 and a circumferential groove 3070, which act in concert to facilitate attachment of the handle element 3062. The shaped end 3068 may have any shape that allows a handle element 3062 to apply torque on the drive shaft 3058, and the circumferential groove 3066 is configured to receive an attachment element of the handle element 3062. In the instant example, the handle element 3062 is a detachable T-handle, however any handle element that allows the user to apply torque to the drive shaft 3058 through the handle element 3062 may be used. The distal portion 3066 of the drive shaft 3058 includes threads 3072.

The translation element 3060 is a generally cylindrical member having a threaded lumen 3074, outer surface 3076, and coupling aperture 3078. The threaded lumen 3074 includes threads that are complementary to the threads 3072 on the drive shaft 3058. The outer surface 3076 engage with the coupler 3042, and the coupling aperture 3078 is configured to receive a locking element (e.g. screw, pin, tack, and the like) that securely mates the translation element 360 and the coupler 3042. Since the drive shaft 3058 is rotatable but translationally stationary, as the drive shaft 3058 rotates the threaded association between the drive shaft 3058 and the translation element 3060 causes the translation element 3060 to translate along the threads 3072 of the drive shaft 3058. For example turning the drive shaft 3058 in a clockwise direction (e.g. via handle element 3062) causes the translation element 3060 to migrate distally along the threads 3072. Since the coupler 3042 is statically attached to the translation element 3060, the coupler 3042 also advances in a distal direction. Furthermore, since the shim holder 3016 is statically attached to the coupler 3042, the shim holder 3016—and attached shim 3001—also advances in a distal direction. Thus, by rotating attached handle element 3062 in a clockwise direction, a user can advance the shim 3001 into the cage 3000.

One of skill will appreciate that the teachings provided herein are directed to basic concepts that can extend beyond any particular embodiment, embodiments, figure, or figures. It should be appreciated that any examples are for purposes of illustration and are not to be construed as otherwise limiting to the teachings. For example, it should be appreciated that the devices provided herein can also be used as implants in other areas of the body. The devices provided herein can be used, for example, in intravertebral body procedures to support or distract vertebral bodies in the repair of, for example, collapsed, damaged or unstable vertebral bodies suffering from disease or injury.

We claim:

1. An intervertebral scaffolding system, comprising:
    a laterovertically-expanding frame configured to create an intervertebral scaffolding system in vivo, the frame having a collapsed state and an expanded state, the expanded state operably contacting the intervertebral space;
    a stabilizer that slideably engages with the distal region of the frame, and is configured for retaining the frame from lateral movement that exceeds the expanded state; and
    an expansion member configured for in vivo introduction into the frame when the frame is in a collapsed state and thereafter expanding the frame to an expanded state;
    wherein the stabilizer includes a locking element that engages with the expansion member to lock the expansion member to the stabilizer when the expansion member is fully inserted into the frame;
    wherein the stabilizer is in an H-configuration having a first vertical leg, a second vertical leg, a cross-member that connects the first vertical leg at least substantially parallel to the second vertical leg, the cross-member having a vertical support member extending at least substantially parallel to the first vertical leg and second vertical leg, and the expansion member includes a vertical slot extending completely through a distal end thereof and dividing the distal end of the expansion member into a first portion and a second portion, the first portion being separated from the second portion by the vertical slot, the vertical slot configured complimentary to the vertical support member; and,
    wherein the first portion and second portion are laterally displaceable relative to one another.

2. The intervertebral scaffolding system of claim 1, wherein laterally displacing the first portion and second portion relative to one another disengages the expansion member from the locking element.

3. An intervertebral scaffolding system, comprising:
    a laterovertically-expanding frame configured to create an intervertebral scaffolding system in vivo, the frame having
        a collapsed state and an expanded state, the expanded state operably contacting the intervertebral space;
        a proximal portion having an end, a distal portion having an end, and a central frame axis of the expanded state;
        a first top beam including a proximal portion having an end and a distal portion having an end, the central axis of the first top beam at least substantially on (i) a top plane containing the central axis of the first top beam and a central axis of a second top beam and (ii) a first side plane containing the central axis of the first top beam and a central axis of a first bottom beam;
        the second top beam including a proximal portion having an end and a distal portion having an end, the central axis of the second top beam at least substantially on (i) the top plane and (ii) a second side plane containing the central axis of the second top beam and a central axis of a second bottom beam;
        the first bottom beam including a proximal portion having an end and a distal portion having an end, the central axis of the first bottom beam at least substantially on (i) a bottom plane containing the central axis of the first bottom beam and the central axis of the second top beam and (ii) the first side plane;
        the second bottom beam including a proximal portion having an end and a distal region having an end, the central axis of the second bottom beam being at least substantially on (i) the bottom plane and (ii) a second side plane containing the central axis of the second bottom beam and the central axis of the second top beam;
        a plurality of top connector elements configured to expandably connect the first top beam to the second top beam, the expanding consisting of a flexing at least substantially on the top plane;
        a plurality of bottom connector elements configured to expandably connect the first bottom beam to the second bottom beam, the expanding consisting of a flexing at least substantially on the bottom plane;
        a plurality of first side connector elements configured to expandably connect the first top beam to the first bottom beam, the expanding consisting of a flexing at least substantially on the first side plane;
        a plurality of second side connector elements configured to expandably connect the second top beam to the second bottom beam, the expanding consisting of a flexing at least substantially on the second side plane;

an expansion member configured for in vivo introduction into the frame when the frame is in a collapsed state and thereafter expanding the frame to an expanded state; and a stabilizer that slidably engages with the distal region of the first top beam, the first bottom beam, the second top beam, the second bottom beam, or a combination thereof, and is configured for retaining the first top beam, the first bottom beam, the second top beam, the second bottom beam, or the combination thereof, from a lateral movement that exceeds the expanded state;

wherein the stabilizer includes a locking element that engages with the expansion member to lock the expansion member to the stabilizer when the expansion member is fully inserted into the frame;

wherein the stabilizer is in an H-configuration having a first vertical leg, a second vertical leg, a cross-member that connects the first vertical leg at least substantially parallel to the second vertical leg, the first vertical leg including a retaining surface for engaging with the first top beam and the first bottom beam, the second vertical leg including a retaining surface for engaging with the second top beam and the second bottom beam, and the cross-member providing a tensile force for resisting the first top beam, the first bottom beam, the second top beam, and the second bottom beam from the lateral movement that exceeds the expanded state;

wherein, the cross-member further comprises a vertical support member, the expansion member having vertical slot extending completely through a distal end thereof and dividing the distal end of the expansion member into a first portion and a second portion, the first portion being separated from the second portion by the vertical slot, the vertical slot configured complimentary to the vertical support member, and the vertical slot of the expansion member slidably connects with the vertical support member in the expanded state; and, wherein, the first portion and second portion are laterally displaceable relative to one another, and laterally displacing the first portion and second portion relative to one another disengages the expansion member from the locking element.

4. An intervertebral scaffolding system, comprising:
a laterovertically-expanding frame configured to create an intervertebral scaffolding system in vivo, the frame having a collapsed state and an expanded state, the expanded state operably contacting the intervertebral space;

a stabilizer that slideably engages with the distal region of the frame, and is configured for retaining the frame from lateral movement that exceeds the expanded state; and an expansion member configured for in vivo introduction into the frame when the frame is in a collapsed state and thereafter expanding the frame to an expanded state;

wherein,
the stabilizer includes a locking element that engages with the expansion member to lock the expansion member to the stabilizer when the expansion member is fully inserted into the frame;
the expansion member includes a vertical slot extending completely through a distal end thereof and dividing the distal end of the expansion member into a first portion and a second portion, the first portion being separated from the second portion by the vertical slot, the vertical slot configured complimentary to the vertical support member; and, the first portion and second portion are laterally displaceable relative to one another.

5. The intervertebral scaffolding system of claim 4, wherein the stabilizer is in an H-configuration having a first vertical leg, a second vertical leg, a cross-member that connects the first vertical leg at least substantially parallel to the second vertical leg, the cross-member having a vertical support member extending at least substantially parallel to the first vertical leg and second vertical leg.

6. An intervertebral scaffolding system, comprising:
a laterovertically-expanding frame configured to create an intervertebral scaffolding system in vivo, the frame having
a collapsed state and an expanded state, the expanded state operably contacting the intervertebral space;
a first top beam, a first bottom beam, a second top beam, and a second top beam;
an expansion member configured for in vivo introduction into the frame when the frame is in a collapsed state and thereafter expanding the frame to an expanded state; and, a stabilizer that slidably engages with the distal region of the first top beam, the first bottom beam, the second top beam, the second bottom beam, or a combination thereof, and is configured for retaining the first top beam, the first bottom beam, the second top beam, the second bottom beam, or the combination thereof, from a lateral movement that exceeds the expanded state;

wherein,
the expansion member includes a vertical slot extending completely through a distal end thereof and dividing the distal end of the expansion member into a first portion and a second portion, the first portion being separated from the second portion by the vertical slot, the vertical slot configured complimentary to the vertical support member; and, the first portion and second portion are laterally displaceable relative to one another.

7. The scaffolding system of claim 6, wherein the stabilizer is in an H-configuration having a first vertical leg, a second vertical leg, and a cross-member that connects the first vertical leg at least substantially parallel to the second vertical leg, the first vertical leg including a retaining surface for engaging with the first top beam and the first bottom beam, the second vertical leg including a retaining surface for engaging with the second top beam and the second bottom beam, and the cross-member providing a tensile force for resisting the first top beam, the first bottom beam, the second top beam, and the second bottom beam from the lateral movement that exceeds the expanded state.

8. The scaffolding system of claim 6, wherein the stabilizer is in an H-configuration having a first vertical leg, a second vertical leg, and a cross-member that connects the first vertical leg at least substantially parallel to the second vertical leg, the first vertical leg including a retaining surface for engaging with the first top beam and the first bottom beam, the second vertical leg including a retaining surface for engaging with the second top beam and the second bottom beam, and the cross-member providing a tensile force for resisting the first top beam, the first bottom beam, the second top beam, and the second bottom beam from the lateral movement that exceeds the expanded state;

wherein, the expansion member further includes a horizontal groove configured complementary to the cross-member of the stabilizer, and the horizontal groove of the expansion member slidably connects with the cross-member in the expanded state.

9. The scaffolding system of claim 6, wherein the stabilizer is in an H-configuration having a first vertical leg, a second vertical leg, a cross-member that connects the first vertical leg at least substantially parallel to the second vertical leg, the first vertical leg including a retaining surface for engaging with the first top beam and the first bottom beam, the second vertical leg including a retaining surface for engaging with the second top beam and the second bottom beam, and the cross-member providing a tensile force for resisting the first top beam, the first bottom beam, the second top beam, and the second bottom beam from the lateral movement that exceeds the expanded state;
wherein, the cross-member further comprises a vertical support member, and the vertical slot of the expansion member is configured complimentary to the vertical support member, and the vertical slot of the expansion member slidably connects with the vertical support member in the expanded state.

10. The scaffolding system of claim 9, wherein the expansion member further includes a horizontal groove configured complementary to the cross-member of the stabilizer, and the horizontal groove of the expansion member slidably connects with the cross-member in the expanded state.

11. The scaffolding system of claim 6, wherein the stabilizer is in an H-configuration having a first vertical leg, a second vertical leg, a cross-member that connects the first vertical leg at least substantially parallel to the second vertical leg, the first vertical leg including a retaining surface for engaging with the first top beam and the first bottom beam, the second vertical leg including a retaining surface for engaging with the second top beam and the second bottom beam, and the cross-member providing a tensile force for resisting the first top beam, the first bottom beam, the second top beam, and the second bottom beam from the lateral movement that exceeds the expanded state;
wherein, the stabilizer further comprises a point of attachment for releasably attaching a guidewire adapted for guiding the expansion member into the laterovertically expanding frame.

12. The scaffolding system of claim 6, wherein the stabilizer is in an H-configuration having a first vertical leg, a second vertical leg, a cross-member that connects the first vertical leg at least substantially parallel to the second vertical leg, the first vertical leg including a retaining surface for engaging with the first top beam and the first bottom beam, the second vertical leg including a retaining surface for engaging with the second top beam and the second bottom beam, and the cross-member providing a tensile force for resisting the first top beam, the first bottom beam, the second top beam, and the second bottom beam from the lateral movement that exceeds the expanded state;
wherein, the cross-member includes a first pillar and a second pillar that operably connect at a hub that has a point of attachment for releasably attaching a guidewire for guiding the expansion member into the laterovertically expanding frame.

13. The scaffolding system of claim 6, further comprising a grafting port.

14. The scaffolding system of claim 6, wherein the system further includes a top tensioner operably attaching the first top beam to the second top beam and a bottom tensioner operably attaching the first bottom beam to the second bottom beam, wherein each plurality connector elements are struts; and wherein,
the top struts are configured monolithically integral to the first top beam and the second top beam;
the bottom struts are configured monolithically integral to the first bottom beam and the second bottom beam;
the top tensioner is configured monolithically integral to the first top beam and the second top beam; and,
the bottom tensioner is configured monolithically integral to the first bottom beam and the second bottom beam;
wherein, the top struts and bottom struts of the laterovertically-expanding frame are each configured to open a graft distribution window upon expansion, expanding from the first top beam to the second top beam, the first top beam to the first bottom beam, the second top beam to the second bottom beam, or the first bottom beam to the second bottom beam.

15. The scaffolding system of claim 6, wherein the system further includes a top tensioner operably attaching the first top beam to the second top beam and a bottom tensioner operably attaching the first bottom beam to the second bottom beam, and wherein,
the top connector struts are configured monolithically integral to the first top beam and the second top beam; and,
the bottom struts are configured monolithically integral to the first bottom beam and the second bottom beam;
the first side struts are configured monolithically integral to the first top beam and the first bottom beam;
the second side struts are configured monolithically integral to the second top beam and the second bottom beam;
the top tensioner is configured monolithically integral to the first top beam and the second top beam; and,
the bottom tensioner is configured monolithically integral to the first bottom beam and the second bottom beam;
wherein, the top, bottom, first side, and second side of the laterovertically-expanding frame form a monolithically integral frame.

16. A method of fusing an intervertebral space using the scaffolding system of claim 6, the method comprising:
creating a point of entry into an intervertebral disc, the intervertebral disc having a nucleus pulposus surrounded by an annulus fibrosis;
removing the nucleus pulposus from within the intervertebral disc through the point of entry, leaving the intervertebral space for expansion of the scaffolding system of claim 6 within the annulus fibrosis, the intervertebral space having a top vertebral plate and a bottom vertebral plate;
inserting the laterovertically expanding frame in the collapsed state through the point of entry into the intervertebral space;
expanding the laterovertically expanding frame to form the scaffolding system;
and,
adding a grafting material to the intervertebral space.

17. The method of claim 16, wherein the creating the point of entry comprises creating a lateral dimension of the point of entry ranging from about 5 mm to about 15 mm, and the amount of lateral expansion is selected to exceed the lateral dimension of the point of entry.

18. The method of claim 16, wherein the expanding includes
expanding the laterovertically expanding frame laterally to a width that exceeds the width of the point of entry; and,
expanding the laterovertically expanding frame vertically to support the intervertebral space in the expanded state.

19. A kit, comprising:
the scaffolding system of claim 6;
a cannula for inserting the scaffolding system into the intervertebral space; and,
a guidewire adapted for guiding the expansion member into the laterovertically expanding frame.

* * * * *